(12) United States Patent
Ranalletta et al.

(10) Patent No.: US 8,864,725 B2
(45) Date of Patent: Oct. 21, 2014

(54) HAZARDOUS DRUG HANDLING SYSTEM, APPARATUS AND METHOD

(75) Inventors: Joseph V. Ranalletta, Englewood, CO (US); Randy Kent Hall, Parker, CO (US); Brian William Ward, Littleton, CO (US); Caryl Lyn Wojcik, Littleton, CO (US)

(73) Assignee: Baxter Corporation Englewood, Englewood, CO (US)

( * ) Notice: Subject to any disclaimer, the term of this patent is extended or adjusted under 35 U.S.C. 154(b) by 0 days.

(21) Appl. No.: 12/405,935

(22) Filed: Mar. 17, 2009

(65) Prior Publication Data

US 2010/0241088 A1 Sep. 23, 2010

(51) Int. Cl.
| | |
|---|---|
| *A61M 5/00* | (2006.01) |
| *A61M 39/10* | (2006.01) |
| *A61J 1/20* | (2006.01) |
| *A61M 39/26* | (2006.01) |
| *A61J 1/10* | (2006.01) |
| *A61M 39/00* | (2006.01) |
| *A61J 1/14* | (2006.01) |

(52) U.S. Cl.
CPC .......... *A61M 39/1011* (2013.01); *A61J 1/2096* (2013.01); *A61J 2001/2055* (2013.01); *A61J 2001/2051* (2013.01); *A61J 2001/201* (2013.01); *A61J 1/2089* (2013.01); *A61J 1/10* (2013.01); *A61M 39/26* (2013.01); *A61M 2039/0009* (2013.01); *A61J 1/1475* (2013.01)
USPC ........... 604/249; 604/533; 604/537; 604/539; 604/284

(58) Field of Classification Search
CPC ............. A61M 2039/1083; A61M 2039/1088; A61M 39/10
USPC .......................... 604/533, 537, 539, 284, 249
See application file for complete search history.

(56) References Cited

U.S. PATENT DOCUMENTS

| 811,811 A | 2/1906 | Allison |
|---|---|---|
| 1,105,959 A | 8/1914 | Bruss |

(Continued)

FOREIGN PATENT DOCUMENTS

| CA | 2518617 A1 | 7/2004 |
|---|---|---|
| EP | 0309771 | 4/1989 |

(Continued)

OTHER PUBLICATIONS

BAXA Corporation, "PhaSeal, The Only Documented, Closed System for Hazardous Drug Handling", Brochure, 2003, 6 Pages.

*Primary Examiner* — Edelmira Bosques
(74) *Attorney, Agent, or Firm* — Marsh Fischmann & Breyfogle LLP

(57) ABSTRACT

A system is provided for use and handling a medical liquid (e.g. hazardous drugs) that includes a transfer adapter having a port rotatably interconnectable to a male luer fitting of a needleless syringe or infusion tubing line port, and a patient connector having a port rotatable interconnectable to a female luer fitting of an intravascular catheter access port. Ports of the transfer adapter and patient connector are interconnectable to automatically define a closed fluid passageway. A vial adapter and/or a reservoir adapter may be provided for selective interconnection to the transfer adapter wherein a second closed fluid passageway and/or a third closed fluid passageway are automatically defined upon interconnection with the transfer adapter. The features may be included with restrict disconnection of the transfer adapter from the male luer fitting after initial connection therewith which restricts disconnection of a vial adapter after initial interconnection therewith and/or which restricts disconnection of a reservoir adapter from a fluid reservoir after initial connection therewith. Various methods are provided which utilize one or more of the noted components.

42 Claims, 36 Drawing Sheets

(56) References Cited

U.S. PATENT DOCUMENTS

| | | | |
|---|---|---|---|
| 1,180,665 | A | 4/1916 | McElroy |
| 2,579,724 | A | 12/1951 | Breakstone |
| 2,999,499 | A | 7/1958 | Willet |
| 3,171,412 | A | 3/1965 | Braun |
| 3,241,663 | A | 3/1966 | Kaepernik |
| 3,352,531 | A | 11/1967 | Kilmarx |
| 3,399,677 | A | 9/1968 | Gould et al. |
| 3,502,097 | A | 3/1970 | Muller |
| 3,570,484 | A | 3/1971 | Steer |
| 3,805,986 | A | 4/1974 | Gaudin |
| 3,822,700 | A | 7/1974 | Pennington |
| 3,837,381 | A | 9/1974 | Arroyo |
| 3,941,126 | A | 3/1976 | Dietrich et al. |
| 3,976,073 | A | 8/1976 | Quick et al. |
| 3,986,508 | A | 10/1976 | Barrington |
| 3,993,068 | A | 11/1976 | Forberg |
| 3,994,293 | A | 11/1976 | Ferro |
| 4,000,739 | A | 1/1977 | Stevens |
| 4,016,081 | A | 4/1977 | Martinez et al. |
| 4,063,555 | A | 12/1977 | Ulinder |
| 4,080,965 | A | 3/1978 | Phillips |
| 4,133,314 | A | 1/1979 | Bloom et al. |
| 4,161,178 | A | 7/1979 | Genese |
| 4,174,731 | A | 11/1979 | Sturgis et al. |
| 4,187,846 | A | 2/1980 | Lolachi et al. |
| 4,197,848 | A | 4/1980 | Garrett et al. |
| 4,201,208 | A | 5/1980 | Cambio, Jr. |
| 4,234,239 | A | 11/1980 | Wilmes et al. |
| 4,240,411 | A | 12/1980 | Hosono |
| 4,324,239 | A | 4/1982 | Gordon et al. |
| 4,328,802 | A | 5/1982 | Curley et al. |
| 4,334,551 | A | 6/1982 | Pfister |
| 4,338,933 | A | 7/1982 | Bayard et al. |
| 4,362,156 | A | 12/1982 | Feller, Jr. et al. |
| 4,397,091 | A | 8/1983 | Gustavsson et al. |
| 4,410,321 | A | 10/1983 | Pearson et al. |
| 4,411,662 | A | 10/1983 | Pearson |
| 4,421,123 | A | 12/1983 | Percarpio |
| 4,432,755 | A | 2/1984 | Pearson |
| 4,449,693 | A | 5/1984 | Gereg |
| 4,457,749 | A | 7/1984 | Bellotti et al. |
| 4,458,733 | A | 7/1984 | Lyons |
| 4,475,548 | A | 10/1984 | Muto |
| 4,496,348 | A | 1/1985 | Genese et al. |
| 4,511,359 | A | 4/1985 | Vaillancourt |
| 4,512,766 | A | 4/1985 | Vailancourt |
| 4,563,176 | A | 1/1986 | Gustavsson et al. |
| 4,564,054 | A | 1/1986 | Gustavsson |
| 4,576,594 | A | 3/1986 | Greenland |
| 4,581,019 | A | 4/1986 | Curelaru et al. |
| 4,607,671 | A | 8/1986 | Aalto et al. |
| 4,617,012 | A | 10/1986 | Vaillancourt |
| 4,655,752 | A | 4/1987 | Honkanen et al. |
| 4,673,404 | A | 6/1987 | Gustavsson |
| 4,704,105 | A | 11/1987 | Adorjan et al. |
| 4,713,060 | A | 12/1987 | Riuli |
| 4,725,267 | A | 2/1988 | Vaillancourt |
| 4,745,950 | A | 5/1988 | Mathieu |
| 4,752,287 | A | 6/1988 | Kurtz et al. |
| 4,752,292 | A | 6/1988 | Lopez et al. |
| 4,759,756 | A | 7/1988 | Forman et al. |
| 4,768,568 | A | 9/1988 | Fournier et al. |
| 4,781,702 | A | 11/1988 | Herrli |
| 4,785,858 | A | 11/1988 | Valentini et al. |
| 4,785,859 | A | 11/1988 | Gustavsson et al. |
| 4,809,679 | A | 3/1989 | Shimonaka et al. |
| 4,834,149 | A | 5/1989 | Fournier et al. |
| 4,857,068 | A | 8/1989 | Kahn |
| 4,863,201 | A | 9/1989 | Carstens |
| 4,872,494 | A | 10/1989 | Coccia |
| 4,874,377 | A | 10/1989 | Newgard et al. |
| 4,893,636 | A | 1/1990 | Cook et al. |
| 4,898,209 | A | 2/1990 | Zbed |
| 4,908,018 | A | 3/1990 | Thomsen |
| 4,909,290 | A | 3/1990 | Coccia |
| 4,920,976 | A | 5/1990 | Calzi et al. |
| 4,932,937 | A | 6/1990 | Gustavsson et al. |
| 4,935,009 | A * | 6/1990 | Caldwell et al. ............... 604/507 |
| 4,951,512 | A | 8/1990 | Mazza et al. |
| 4,959,053 | A | 9/1990 | Jang |
| 4,997,430 | A | 3/1991 | Van Der Heiden et al. |
| 4,998,713 | A | 3/1991 | Vaillancourt |
| 4,998,927 | A | 3/1991 | Vaillancourt |
| 5,000,349 | A | 3/1991 | Rautsola et al. |
| 5,006,114 | A | 4/1991 | Rogers et al. |
| 5,037,382 | A | 8/1991 | Kvorning et al. |
| 5,041,106 | A | 8/1991 | Noji et al. |
| 5,064,416 | A | 11/1991 | Newgard et al. |
| 5,065,783 | A | 11/1991 | Ogle, II |
| 5,092,840 | A | 3/1992 | Healy |
| 5,108,380 | A | 4/1992 | Herlitze et al. |
| 5,122,123 | A | 6/1992 | Vaillancourt |
| 5,127,904 | A | 7/1992 | Loo et al. |
| 5,130,254 | A | 7/1992 | Collier et al. |
| 5,132,088 | A | 7/1992 | Wakatake |
| 5,154,703 | A | 10/1992 | Bonaldo |
| 5,188,620 | A | 2/1993 | Jepson et al. |
| 5,199,947 | A | 4/1993 | Lopez et al. |
| 5,269,771 | A | 12/1993 | Thomas et al. |
| 5,279,605 | A | 1/1994 | Karrasch et al. |
| 5,281,206 | A | 1/1994 | Lopez |
| 5,289,858 | A | 3/1994 | Grabenkort |
| 5,290,254 | A | 3/1994 | Vaillancourt |
| 5,303,751 | A | 4/1994 | Slater et al. |
| 5,328,474 | A | 7/1994 | Raines |
| 5,330,450 | A | 7/1994 | Lopez |
| 5,344,414 | A | 9/1994 | Lopez et al. |
| 5,352,210 | A | 10/1994 | Marrucchi |
| 5,360,413 | A | 11/1994 | Leason et al. |
| 5,380,306 | A | 1/1995 | Brinon |
| 5,423,753 | A | 6/1995 | Fowles et al. |
| 5,466,220 | A | 11/1995 | Brenneman |
| 5,492,147 | A | 2/1996 | Challender et al. |
| 5,498,253 | A | 3/1996 | Aswad et al. |
| 5,520,666 | A | 5/1996 | Choudhury et al. |
| 5,533,647 | A | 7/1996 | Long-Hsiung |
| 5,535,771 | A | 7/1996 | Purdy et al. |
| 5,549,577 | A | 8/1996 | Siegel et al. |
| 5,558,838 | A | 9/1996 | Uffenheimer |
| 5,620,433 | A | 4/1997 | Aswad et al. |
| 5,658,260 | A | 8/1997 | Desecki et al. |
| 5,676,346 | A | 10/1997 | Leinsing |
| 5,685,866 | A | 11/1997 | Lopez |
| 5,688,254 | A | 11/1997 | Lopez et al. |
| 5,694,686 | A | 12/1997 | Lopez |
| 5,695,466 | A | 12/1997 | Lopez et al. |
| RE35,841 | E | 7/1998 | Frank et al. |
| 5,776,116 | A | 7/1998 | Lopez et al. |
| 5,776,125 | A | 7/1998 | Dudar et al. |
| 5,783,094 | A | 7/1998 | Kraus et al. |
| 5,833,213 | A | 11/1998 | Ryan |
| 5,839,715 | A | 11/1998 | Leinsing |
| 5,873,862 | A | 2/1999 | Lopez |
| 5,891,129 | A | 4/1999 | Daubert et al. |
| 5,893,397 | A | 4/1999 | Peterson et al. |
| 5,895,575 | A | 4/1999 | Kraus et al. |
| 5,901,942 | A | 5/1999 | Lopez |
| 5,902,281 | A | 5/1999 | Kraus et al. |
| 5,924,584 | A | 7/1999 | Hellstrom et al. |
| 5,928,204 | A | 7/1999 | Lopez |
| 5,954,104 | A | 9/1999 | Daubert et al. |
| 5,954,708 | A | 9/1999 | Lopez et al. |
| 5,971,950 | A | 10/1999 | Lopez et al. |
| 5,988,456 | A | 11/1999 | Laible |
| 6,006,388 | A | 12/1999 | Young |
| 6,050,978 | A | 4/2000 | Orr et al. |
| 6,063,068 | A | 5/2000 | Fowles et al. |
| 6,090,091 | A | 7/2000 | Fowles et al. |
| 6,113,068 | A | 9/2000 | Ryan |
| 6,113,583 | A | 9/2000 | Fowles et al. |
| 6,117,107 | A | 9/2000 | Chen |
| 6,117,112 | A | 9/2000 | Mahurkar |
| 6,132,403 | A | 10/2000 | Lopez |
| 6,139,534 | A | 10/2000 | Niedospial, Jr. et al. |

(56) References Cited

U.S. PATENT DOCUMENTS

| | | | |
|---|---|---|---|
| 6,142,345 A | 11/2000 | Laible | |
| 6,146,362 A * | 11/2000 | Turnbull et al. | 604/256 |
| 6,168,581 B1 | 1/2001 | Buchler | |
| 6,189,580 B1 | 2/2001 | Thibault et al. | |
| 6,190,363 B1 | 2/2001 | Gabbard et al. | |
| 6,193,675 B1 | 2/2001 | Kraus et al. | |
| 6,209,738 B1 | 4/2001 | Jansen et al. | |
| 6,258,068 B1 | 7/2001 | Kirchhofer et al. | |
| 6,273,152 B1 | 8/2001 | Buchler et al. | |
| 6,290,206 B1 | 9/2001 | Doyle | |
| 6,290,688 B1 | 9/2001 | Lopez et al. | |
| 6,341,802 B1 | 1/2002 | Matkovich | |
| 6,343,629 B1 | 2/2002 | Wessman et al. | |
| 6,344,033 B1 | 2/2002 | Jepson et al. | |
| 6,378,576 B2 | 4/2002 | Thibault et al. | |
| 6,378,714 B1 | 4/2002 | Jansen et al. | |
| 6,382,442 B1 | 5/2002 | Thibault et al. | |
| 6,398,763 B1 | 6/2002 | Richardson et al. | |
| 6,409,708 B1 | 6/2002 | Wessman | |
| 6,453,949 B1 | 9/2002 | Chau | |
| 6,481,600 B2 | 11/2002 | Buchler | |
| 6,497,684 B2 | 12/2002 | Witowski | |
| 6,503,240 B1 | 1/2003 | Niedospial, Jr. et al. | |
| 6,524,295 B2 | 2/2003 | Daubert et al. | |
| 6,541,802 B2 | 4/2003 | Doyle | |
| 6,544,246 B1 | 4/2003 | Niedospial, Jr. | |
| 6,565,543 B1 | 5/2003 | Buehler | |
| 6,571,837 B2 | 6/2003 | Jansen et al. | |
| 6,572,592 B1 | 6/2003 | Lopez | |
| 6,582,415 B1 | 6/2003 | Fowles et al. | |
| 6,585,691 B1 | 7/2003 | Vitello | |
| 6,585,700 B1 | 7/2003 | Trocki et al. | |
| 6,602,239 B2 | 8/2003 | Ronneklev | |
| 6,610,040 B1 | 8/2003 | Fowles et al. | |
| 6,610,041 B2 | 8/2003 | Daubert et al. | |
| 6,626,309 B1 | 9/2003 | Jansen et al. | |
| 6,629,613 B1 | 10/2003 | Kraus et al. | |
| 6,632,201 B1 | 10/2003 | Mathias et al. | |
| 6,635,043 B2 | 10/2003 | Daubert et al. | |
| 6,648,835 B1 | 11/2003 | Shemesh | |
| 6,669,673 B2 | 12/2003 | Lopez | |
| 6,669,681 B2 | 12/2003 | Jepson et al. | |
| 6,673,045 B1 | 1/2004 | Kraus | |
| 6,681,946 B1 | 1/2004 | Jansen et al. | |
| 6,682,509 B2 | 1/2004 | Lopez | |
| 6,692,479 B2 | 2/2004 | Kraus et al. | |
| 6,695,829 B2 | 2/2004 | Hellstrom et al. | |
| 6,706,022 B1 | 3/2004 | Leinsing et al. | |
| 6,706,031 B2 | 3/2004 | Manera | |
| 6,715,520 B2 | 4/2004 | Andreasson et al. | |
| 6,745,998 B2 | 6/2004 | Doyle | |
| 6,758,833 B2 | 7/2004 | Lopez | |
| 6,767,466 B2 | 7/2004 | Kraus et al. | |
| 6,800,066 B2 | 10/2004 | Targell | |
| 6,809,804 B1 | 10/2004 | Yount et al. | |
| 6,813,868 B2 | 11/2004 | Baldwin et al. | |
| 6,821,267 B2 | 11/2004 | Veillon, Jr. et al. | |
| 6,840,501 B2 | 1/2005 | Doyle | |
| 6,846,302 B2 | 1/2005 | Shemesh et al. | |
| 6,852,103 B2 | 2/2005 | Fowles et al. | |
| 6,871,838 B2 * | 3/2005 | Raines et al. | 251/149.4 |
| 6,875,203 B1 | 4/2005 | Fowles et al. | |
| 6,890,328 B2 | 5/2005 | Fowles et al. | |
| 6,904,662 B2 | 6/2005 | Thibault et al. | |
| 6,913,056 B2 | 7/2005 | Landherr et al. | |
| 6,929,751 B2 | 8/2005 | Bowman, Jr. et al. | |
| 6,939,111 B2 | 9/2005 | Huitt et al. | |
| 6,942,638 B1 | 9/2005 | Quinn | |
| 6,945,417 B2 | 9/2005 | Jansen et al. | |
| 6,948,522 B2 | 9/2005 | Newbrough et al. | |
| 6,953,450 B2 | 10/2005 | Baldwin et al. | |
| 6,957,745 B2 | 10/2005 | Thibault et al. | |
| 6,964,406 B2 | 11/2005 | Doyle | |
| 6,975,924 B2 | 12/2005 | Kircher et al. | |
| 6,994,315 B2 | 2/2006 | Ryan et al. | |
| 7,021,148 B2 | 4/2006 | Kuhn et al. | |
| 7,025,389 B2 | 4/2006 | Cuschieri et al. | |
| 7,081,109 B2 | 7/2006 | Tighe et al. | |
| 7,101,352 B2 | 9/2006 | Duchon et al. | |
| 7,104,970 B2 | 9/2006 | Chen | |
| 7,147,621 B2 | 12/2006 | Kiehne | |
| 7,163,525 B2 | 1/2007 | Franer | |
| 7,187,971 B2 | 3/2007 | Sommer et al. | |
| 7,214,209 B2 | 5/2007 | Mazzoni | |
| 7,294,122 B2 | 11/2007 | Kubo et al. | |
| 7,316,669 B2 | 1/2008 | Ranalletta | |
| D571,912 S | 6/2008 | Ranalletta et al. | |
| 7,392,638 B2 | 7/2008 | Baldwin et al. | |
| 7,396,051 B2 | 7/2008 | Baldwin et al. | |
| D579,542 S | 10/2008 | Ranalletta et al. | |
| 7,470,265 B2 | 12/2008 | Brugger et al. | |
| 7,510,547 B2 | 3/2009 | Fangrow | |
| 7,513,895 B2 | 4/2009 | Fangrow | |
| 7,534,238 B2 | 5/2009 | Fangrow | |
| 7,547,300 B2 | 6/2009 | Fangrow | |
| 7,569,043 B2 | 8/2009 | Fangrow | |
| 7,588,684 B2 | 9/2009 | Brugger et al. | |
| 7,611,502 B2 | 11/2009 | Daly | |
| 7,637,889 B2 | 12/2009 | Glynn | |
| 7,645,271 B2 | 1/2010 | Fangrow | |
| 7,654,995 B2 | 2/2010 | Warren et al. | |
| 7,658,733 B2 | 2/2010 | Fangrow | |
| 2001/0025167 A1 | 9/2001 | Kraus et al. | |
| 2002/0099354 A1 | 7/2002 | Ronneklev | |
| 2002/0115981 A1 | 8/2002 | Wessman | |
| 2002/0147429 A1 | 10/2002 | Cowan et al. | |
| 2002/0183699 A1 | 12/2002 | Targell | |
| 2003/0032940 A1 | 2/2003 | Doyle | |
| 2003/0036735 A1 | 2/2003 | Jepson et al. | |
| 2003/0107628 A1 | 6/2003 | Fowles et al. | |
| 2003/0148030 A1 | 8/2003 | Vernon, Jr. et al. | |
| 2003/0187420 A1 | 10/2003 | Akerlund et al. | |
| 2003/0189003 A1 | 10/2003 | Kraus et al. | |
| 2003/0191445 A1 | 10/2003 | Wallen et al. | |
| 2003/0199846 A1 | 10/2003 | Fowles et al. | |
| 2003/0199847 A1 | 10/2003 | Akerlund et al. | |
| 2003/0208151 A1 | 11/2003 | Kraus et al. | |
| 2004/0002684 A1 | 1/2004 | Lopez | |
| 2004/0039341 A1 | 2/2004 | Ranalletta | |
| 2004/0055949 A1 | 3/2004 | Kraus et al. | |
| 2004/0073174 A1 | 4/2004 | Lopez | |
| 2004/0127857 A1 | 7/2004 | Shemesh et al. | |
| 2004/0201216 A1 * | 10/2004 | Segal et al. | 285/401 |
| 2004/0215147 A1 | 10/2004 | Wessman et al. | |
| 2004/0243070 A1 | 12/2004 | Lopez | |
| 2004/0249352 A1 | 12/2004 | Swick | |
| 2005/0182383 A1 | 8/2005 | Wallen | |
| 2005/0211373 A1 | 9/2005 | Tomasetti et al. | |
| 2005/0215976 A1 | 9/2005 | Wallen | |
| 2006/0157971 A1 | 7/2006 | Baldwin et al. | |
| 2006/0229568 A1 | 10/2006 | Koopman | |
| 2006/0259013 A1 | 11/2006 | Ranalletta et al. | |
| 2007/0060898 A1 * | 3/2007 | Shaughnessy et al. | 604/284 |
| 2007/0088282 A1 | 4/2007 | Ranalletta et al. | |
| 2007/0215235 A1 | 9/2007 | Ranalletta et al. | |
| 2008/0009789 A1 | 1/2008 | Zinger et al. | |
| 2009/0030396 A1 | 1/2009 | Ferris | |

FOREIGN PATENT DOCUMENTS

| | | |
|---|---|---|
| WO | 9105581 A1 | 5/1991 |
| WO | WO93/11828 | 6/1993 |
| WO | WO96/26681 A1 | 9/1996 |
| WO | WO 96/29104 A1 | 9/1996 |
| WO | WO 96/32178 A1 | 10/1996 |
| WO | WO 97/45714 A1 | 12/1997 |
| WO | WO 98/46291 A1 | 10/1998 |
| WO | WO00/35517 | 6/2000 |
| WO | WO 00/49939 A1 | 8/2000 |
| WO | WO 01/41844 A1 | 6/2001 |

(56) References Cited

FOREIGN PATENT DOCUMENTS

| WO | WO 01/58507 A2 | 8/2001 |
| WO | WO 03/086577 A1 | 10/2003 |
| WO | WO 2004/058338 A1 | 7/2004 |
| WO | WO2004/664903 | 8/2004 |
| WO | WO 2005/041846 A1 | 5/2005 |
| WO | 2005041846 A2 | 12/2005 |

* cited by examiner

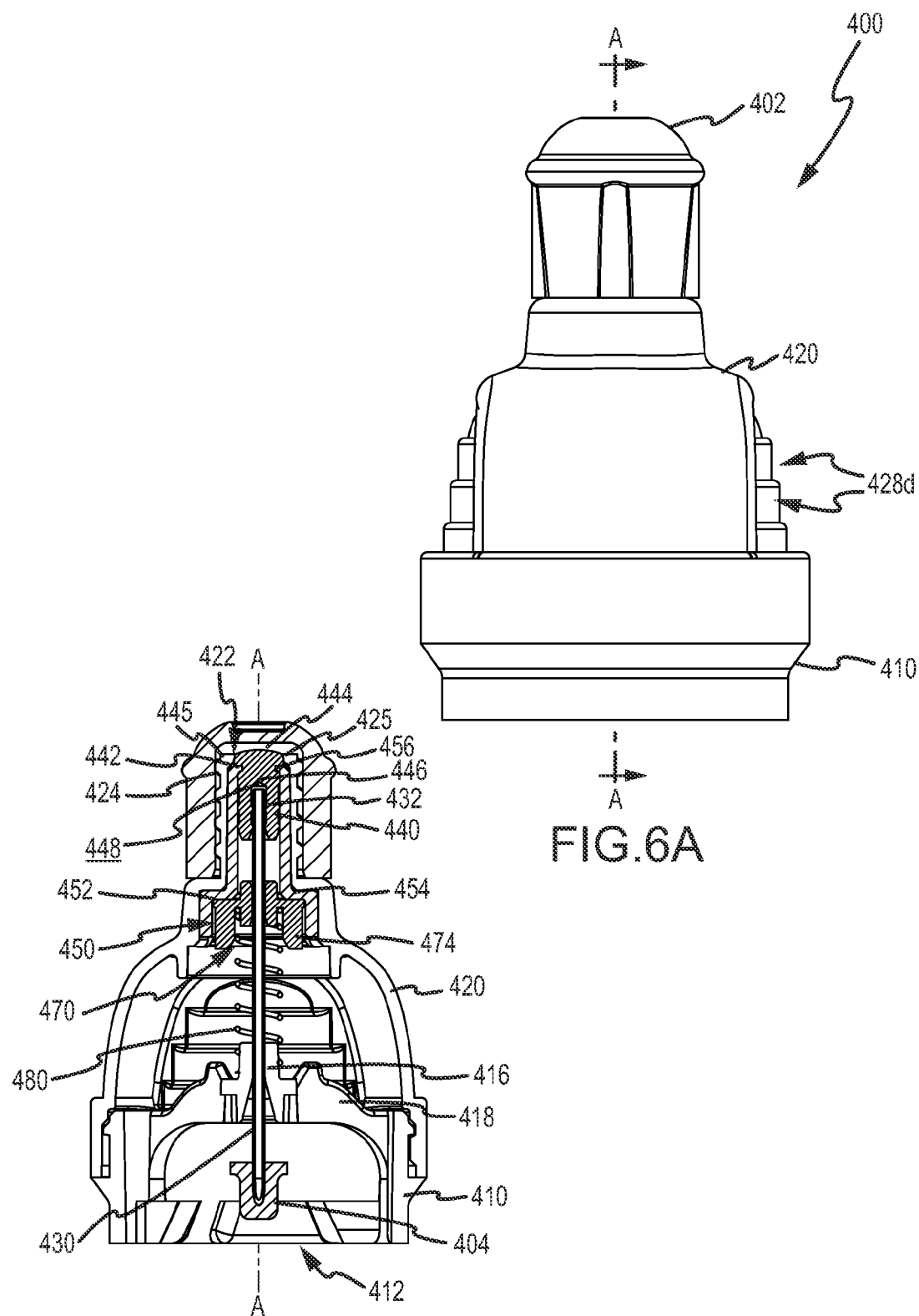

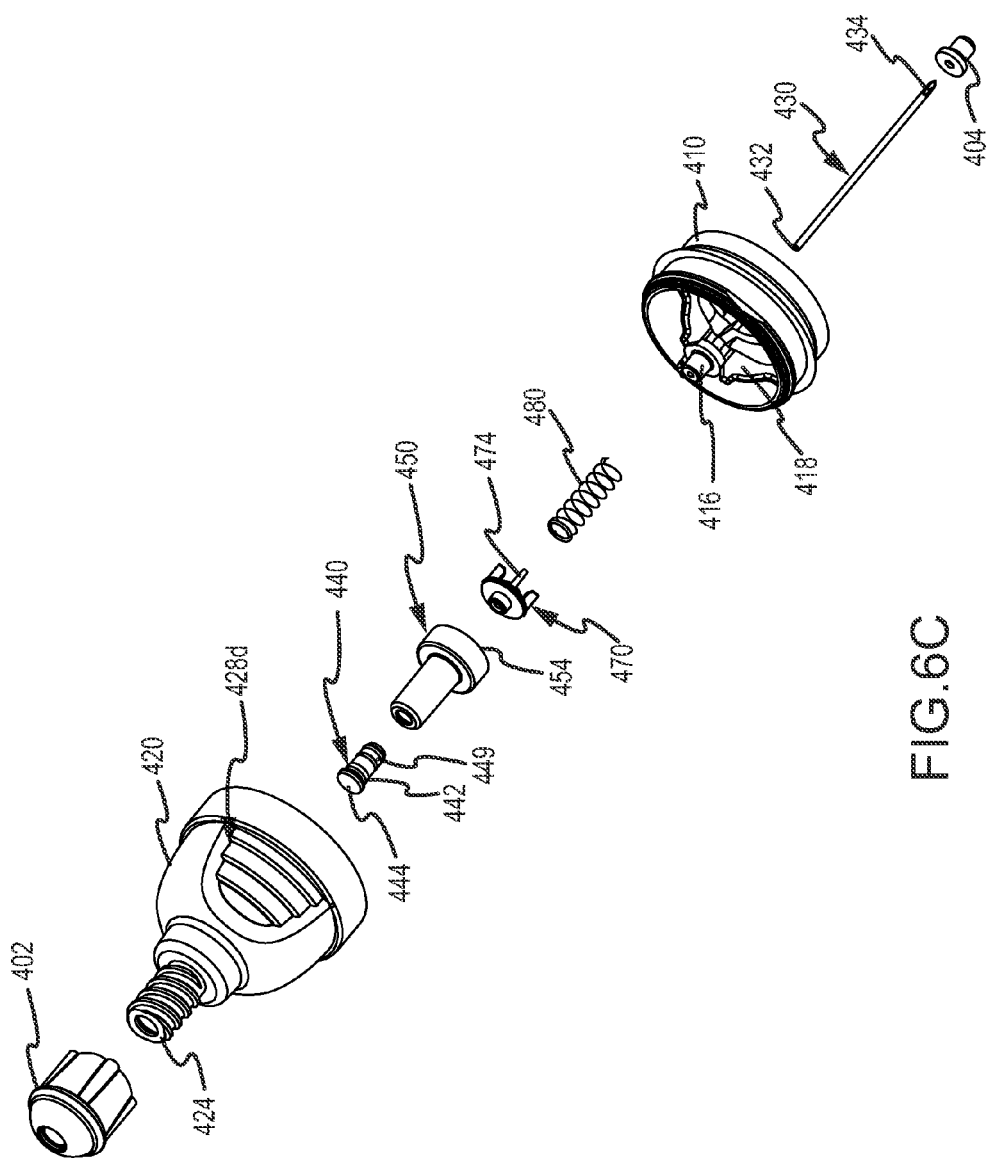

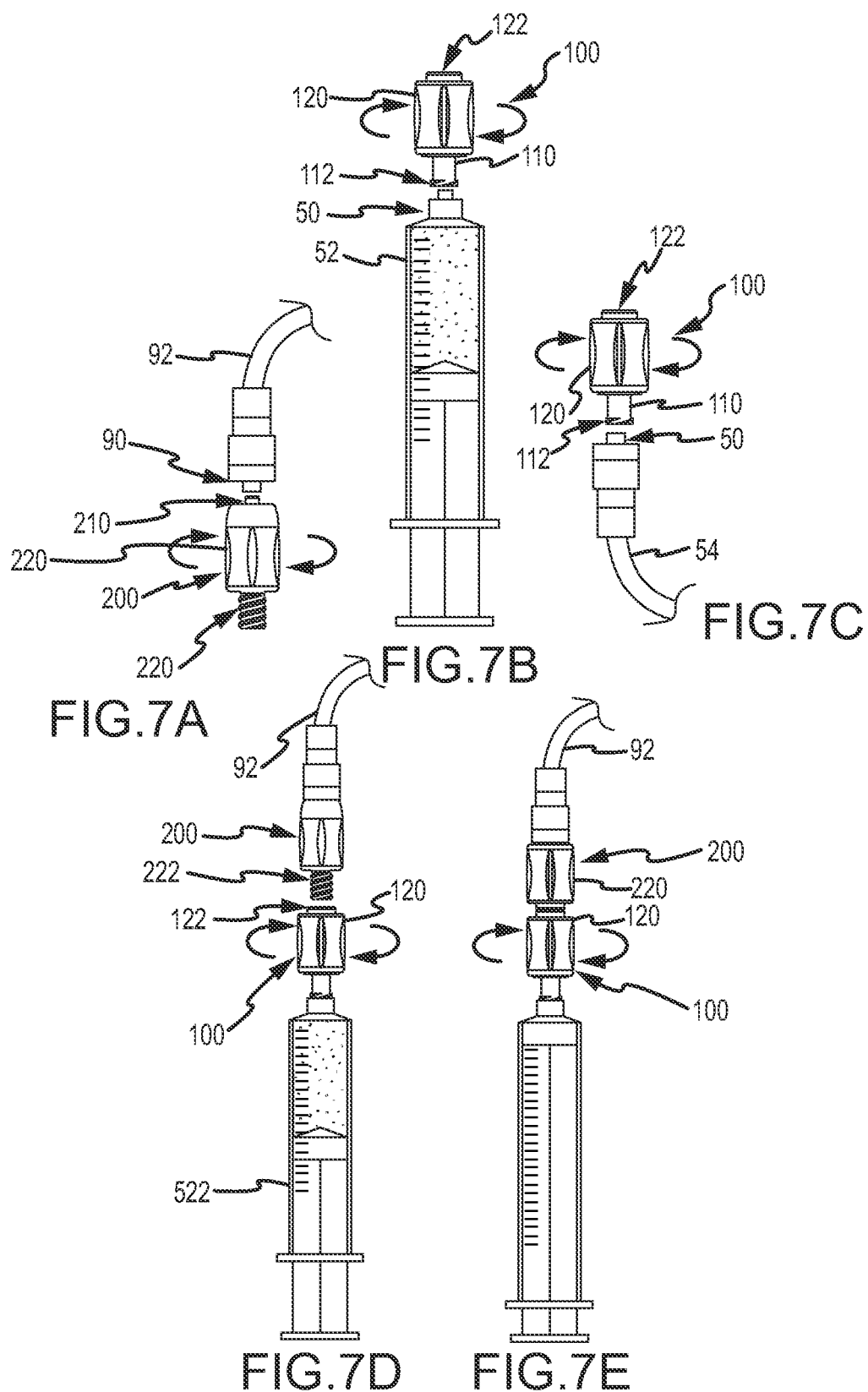

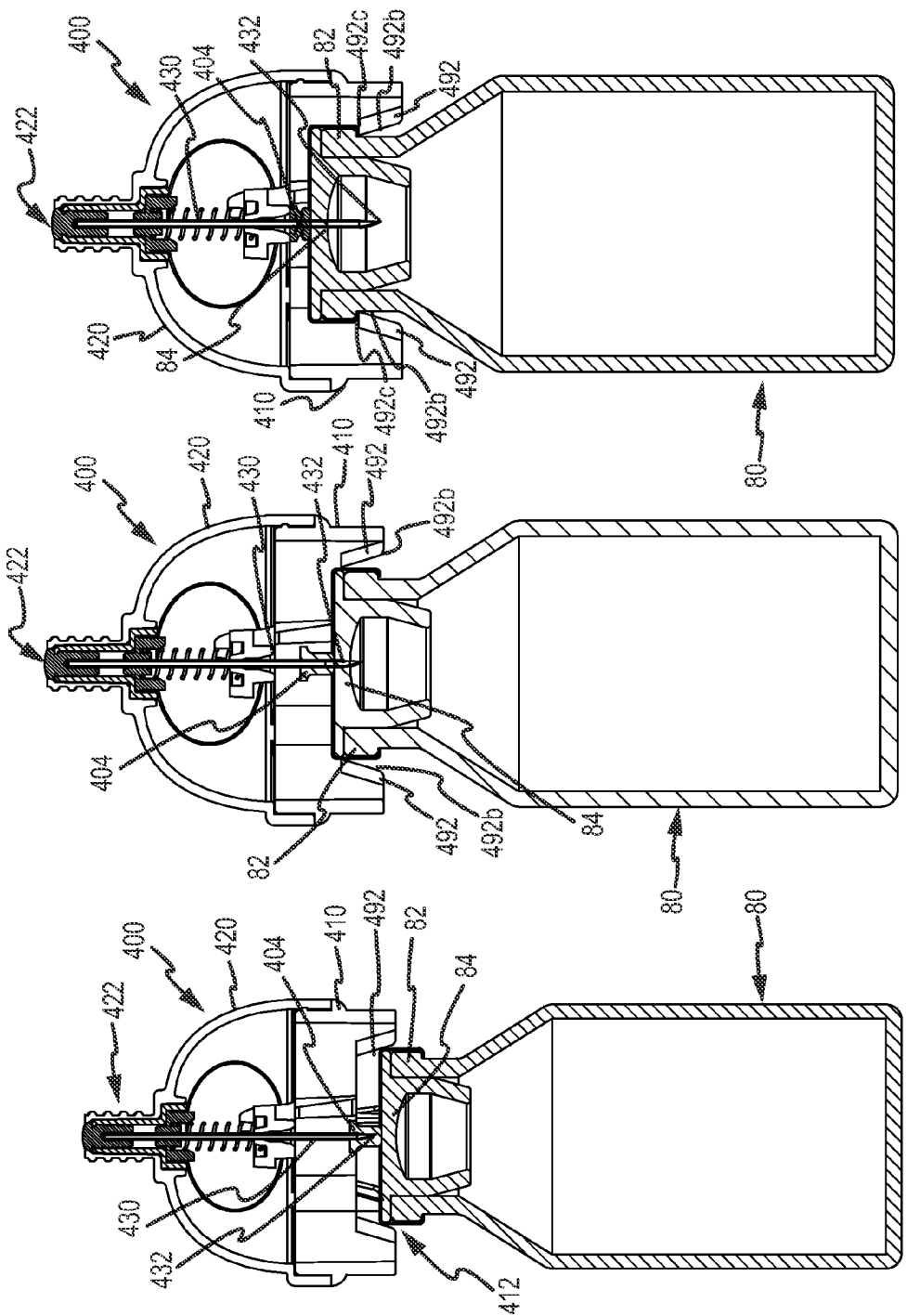

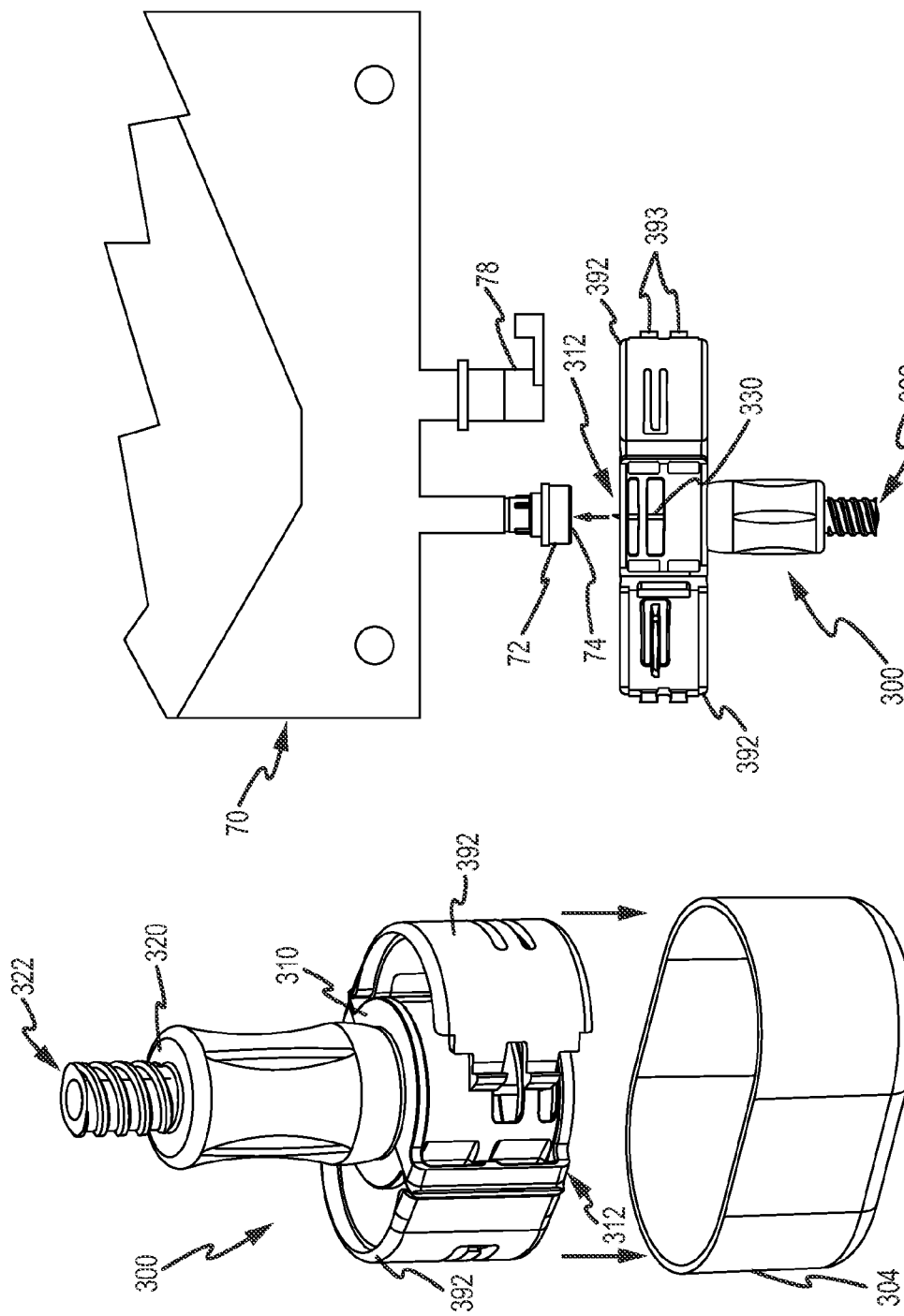

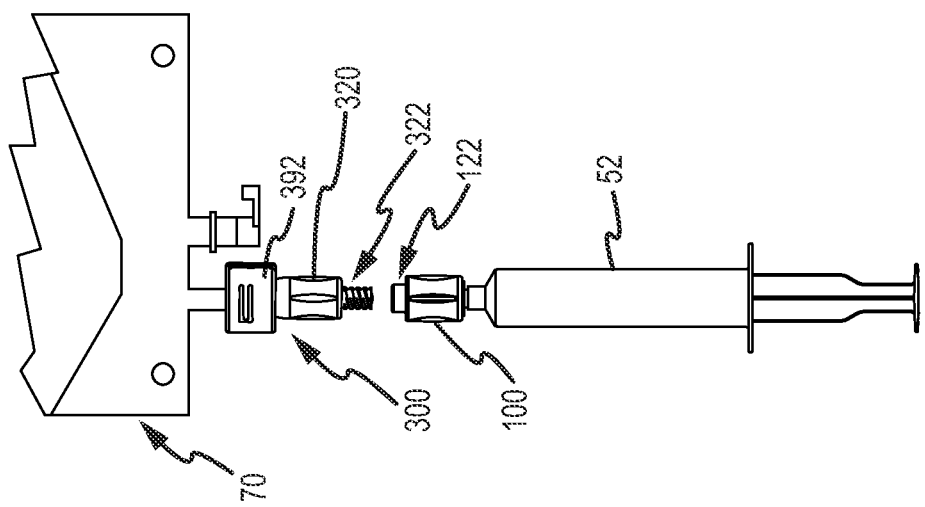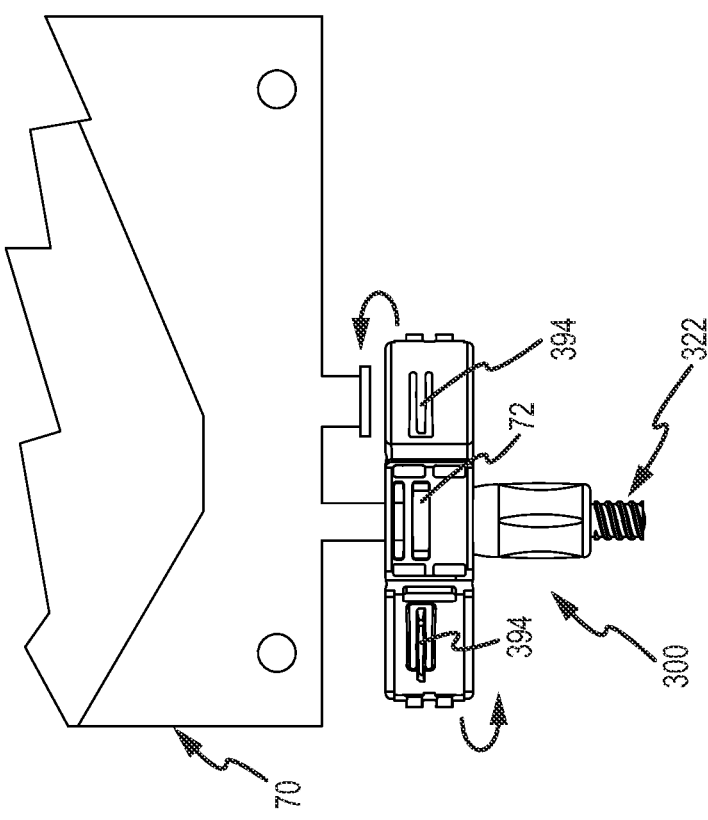

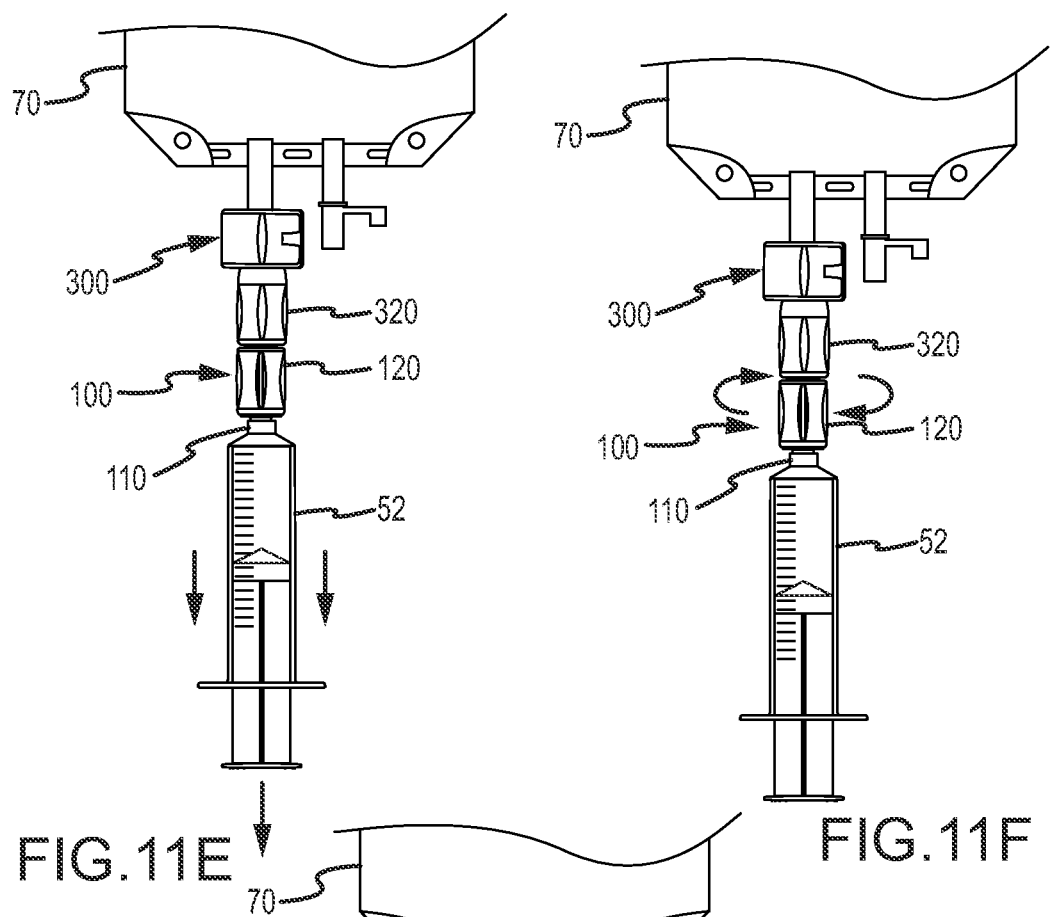
FIG.11E
FIG.11F
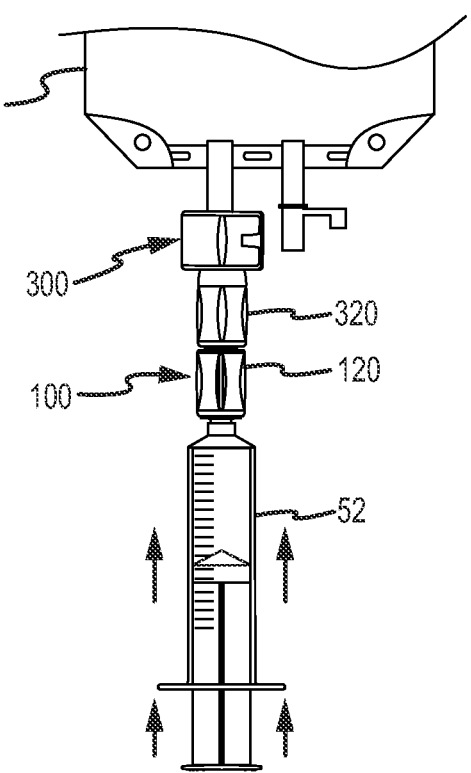
FIG.11G

HAZARDOUS DRUG HANDLING SYSTEM, APPARATUS AND METHOD

FIELD OF THE INVENTION

The present invention relates to systems, apparatus and methods for handling medical liquids, and is particularly apt for handling hazardous drugs in a liquid form (i.e. liquid drugs).

BACKGROUND OF THE INVENTION

Increasingly, it has been recognized that various drugs utilized in conjunction with the treatment of illnesses and injuries may have undesirable side affects to medical personnel who handle such drugs. In this regard, given the hazardous nature of certain drugs, exposure to even a small amount of such drugs may be harmful.

By way of example, antineoplastic, cytotoxic, biologic, antiviral and immunosuppressive agents have been recognized as potentially hazardous drugs. At the same time, the employment of such drugs is increasing in relation to the treatment of numerous human diseases and conditions as well as in veterinary applications. In particular, hazardous drugs are now widely employed in conjunction with the treatment of cancer and HIV infection.

Exposure to hazardous drugs most typically occurs upon contact and/or inhalation in conjunction with the reconstitution and/or dilution of hazardous drugs that are provided in a powder or concentrated liquid form, or in connection with the administration of such hazardous drugs to patients. In the later regard, hazardous drugs are often administered in a liquid form via intravascular catheter ports.

SUMMARY OF THE INVENTION

In view of the foregoing, a primary objective of the present invention is to provide systems, apparatus and methods for handling medical liquids, and in particular, hazardous liquid drugs, with reduced risk of exposure to such drugs by medical personnel.

Another objective of the present invention is to provide improved systems, apparatus and methods for handling liquid drugs in a manner that is user friendly.

Yet another objective of the present invention is to provide improved systems, apparatus and methods for handling liquid drugs in a manner that entails relatively simple componentry.

One or more of the above-noted objectives and additional advantages may be realized by an inventive system for use in handling a medical liquid, e.g. a hazardous liquid drug, comprising a transfer adapter having a first connection port rotatably interconnectable to a male luer fitting of at least one of a needleless syringe and an infusion tubing line port, and a patient connector having a first connection port rotatably interconnectable to a female luer fitting of an intravascular catheter access port. The transfer adapter and patient connector may each further include a second connection port, wherein the second connection port of the transfer adapter may be selectively interconnectable to and disconnectable from the second connection port of the patient connector. As may be appreciated, such an arrangement facilitates the selective passage of a medical liquid from a needleless syringe or infusion tubing line through an interconnected transfer adapter and a patient connector interconnected thereto into a vascular catheter access port (e.g., interconnected to a patient).

The system may further include a vial adapter having a first connection port selectively interconnectable to a vial containing a drug and/or a reservoir adapter having a first connection port selectively interconnectable to a fluid reservoir containing a medical liquid. In turn, the vial adapter may include a second connection port selectively interconnectable to the second connection port of the transfer adapter and/or the reservoir adapter may include a second connection port selectively interconnectable to the second connection port of the transfer adapter. In short, the system may include a patient connector, a vial adapter and/or a reservoir adapter, each having a second connection port selectively and alternately interconnectable to and disconnectable from the second connection port of the transfer adapter.

By virtue of the noted interconnection features, the inventive system may be utilized to facilitate an arrangement in which the first connection port of the transfer adapter may be interconnected to a needleless syringe and in which a second connection port of the transfer adapter may be interconnected to a second connection port of a vial adapter and/or a second connection port of a reservoir adapter, wherein a medical liquid may be passed between the needleless syringe and an interconnected vial and/or an interconnected fluid reservoir, respectively. Further, in some embodiments the second connection port of the patient connector, vial adapter and/or reservoir adapter may be sized for direct interconnection to and disconnection from a male luer fitting (e.g. of a conventional needleless syringe or a conventional infusion tubing line port).

In one aspect, the second connection port of the transfer adapter and the second connection port of the patient connector may be provided so that a first closed fluid passageway through the patient connector and the transfer adapter is automatically defined upon interconnection of the second connection ports thereof. Further, the vial adapter and/or reservoir adapter may be provided so that a closed fluid passageway through the vial adapter and the transfer adapter and/or through the reservoir adapter and the transfer adapter may be automatically defined upon interconnection of the second connection ports thereof.

In certain applications, a liquid drug may be contained within a needleless syringe interconnected to the first connection port of a transfer adapter, wherein at least a portion of the liquid drug may be passed from the needleless syringe into a vascular catheter access port via the transfer adapter and the patient connector interconnected thereto. In other applications, a liquid drug may be contained within a needleless syringe interconnected to the first connection port of the transfer adapter, wherein at least a portion of the liquid drug may be passed from the needleless syringe into a fluid reservoir via the interconnected transfer adapter and a reservoir adapter interconnected thereto. In turn the fluid reservoir may be interconnected via an interconnected infusion tubing line set having a male luer fitting at an end port thereof that may be interconnected to another transfer adapter that may be interconnected to a patient connector that may be interconnected to a vascular catheter port.

The patient connector, and a vial adapter and/or a reservoir adapter may each be provided with a second connection port of a common configuration. In one approach, the second connection port of the transfer adapter may be rotatably interconnectable to and rotatably disconnectable from the second connection port of a patient connector, a second connection port of a vial adapter and/or a second connection port of a reservoir adapter. In certain embodiments, the second connection port of a transfer adapter may comprise an internally-threaded surface, and the second connection port of a patient connector, a second connection port of a vial adapter and/or a second connection port of a reservoir adapter may each comprise an externally-threaded surface, complimentary to the internally-threaded surface of the second connection port of the transfer adapter. In other embodiments, the second connection port of a transfer adapter may comprise an externally-threaded surface, and the second connection port of a patient connector, a second connection port of a vial adapter and/or a second connection port of a reservoir adapter may each comprise an internally-threaded surface, complimentary to the externally-threaded surface of the second port of the transfer adapter.

In another aspect, in addition to a transfer adapter and a patient connector, the system may include a vial adapter and/or a reservoir adapter that includes a second connection port interconnectable to a second connection port of the transfer adapter, a tubular member, and a seal member. The vial adapter and/or reservoir adapter may be provided so that a first end of the tubular member thereof advances through the seal member thereof upon interconnection of the second connection port thereof with the second connection port of the transfer adapter. Further, the transfer adapter may be provided to include a tubular member and a seal member, wherein a first end of the tubular member of the vial adapter and/or the reservoir adapter advances through the seal member of the transfer adapter upon interconnection of the second connection port of the transfer adapter and the second connection port of the vial adapter and/or reservoir adapter, and wherein the first ends of the respective tubular members may be automatically, fluidly interconnected. In this regard, the tubular members of the transfer adapter and the at least one of a vial adapter and reservoir adapter may each define a portion of a closed fluid passageway that extends from the first connection port of the transfer adapter to the first connection port of the vial adapter and/or reservoir adapter upon interconnection of the respective second connection ports.

In further relation to this aspect, the seal member of the vial adapter and/or reservoir adapter may sealably enclose the above-noted first end of the corresponding tubular member when the second connection port thereof is in a disconnected state. Similarly, the seal member of the transfer adapter may sealably enclose the first end of the tubular member thereof when the second connection port thereof is in a disconnected state. Such automatic sealably facilitates multiple connection/disconnection usage of the second connection port(s), e.g. while maintaining an interconnection between the transfer adapter and male luer fitting of a needleless syringe or of a port of an infusing tubing line set, or an interconnection between a vial adapter and a vial and/or an interconnection between a reservoir adapter and a fluid reservoir. Further, such automatic sealably facilitates ready post-use disposal of an interconnected transfer adapter and needleless syringe or infusion tubing line set, an interconnected vial adapter and vial, and/or an interconnected reservoir adapter and fluid reservoir.

In certain embodiments, a tubular member and seal member of the transfer adapter may be biased to a recessed position relative to the second connection port thereof when the second connection port is in a disconnected state. Relatedly, when biased to the recessed position, amend face of the seal member may be located internally inward relative to a distal end portion of internal threads provided at the second connection port of the transfer adapter for rotatable interconnection with complimentary threads provided at the second connection port of the patient connector reservoir adapter and/or vial adapter.

In some implementations, a seal member of the patient connector, vial adapter and/or the reservoir adapter may be axially moveable relative to and biased toward the second connection port thereof. In this regard, a seal member of the patient connector, vial adapter and/or reservoir adapter may be automatically disposed (e.g. vi a spring-loaded carriage) substantially flush with or outwardly beyond the corresponding second connection port when the second connection port is in a disconnected state.

In another aspect, a system may be provided that includes a patient connector having a first interconnection port rotatably interconnectable to a female luer fitting of an intravascular access port, and a second connection port. The system may further include a transfer adapter having a first member manipulable to rotatably interconnect a first connection port thereof to and non-manipulable to rotatably disconnect the first connection port thereof from a male luer fitting (e.g. a conventional male luer fitting of a needless syringe or infusion tubing line port), wherein a second connection port of the transfer adapter is selectively interconnectable to and disconnectable from the second connection port of the patient connector.

In one embodiment, the first member of the transfer adapter may include the second connection port of the transfer adapter. Additionally, the transfer adapter may include a second member that defines the first connection port of the transfer adapter, wherein the first member and the second member of the transfer adapter are interconnected and axially-fixed relative to one another. In one embodiment, the first member may be disposed to co-rotate with the second member upon rotation of the first member in a first direction and to rotate independent from the second member upon rotation of the first member in a second direction that is opposite to the first direction.

In one implementation, the second connection port of the transfer adapter may be provided to be rotatably interconnectable to and disconnectable from the second connection port of the patient connector. In this regard, the second connection ports of the transfer adapter and patient connector may comprise complimentary, internally and externally threaded surfaces, respectively.

In conjunction with the described system adapter, the patient connector and transfer adapter may each include corresponding tubular members which may be automatically, fluidly interconnected to define at least a portion of a closed fluid passageway upon interconnection of the patient connector and transfer adapter. As described hereinabove, the patient connector and transfer adapter may each further include corresponding seal members that sealably enclose ends of the corresponding tubular members thereof when the second connection ports thereof are in a disconnected state. Further, the patient connector may be provided so that the end of the tubular member thereof extends through a front face of the patient connector seal member and through a front face of the transfer adapter seal member upon selective interconnection of the patient connector and transfer adapter.

In various arrangements, the patient connector seal member may be provided to close the second connection port of the patient connector in a disconnected state, wherein a front face of the patient connector seal member is one of disposed substantially flush with and disposed outwardly beyond the second connection port in a disconnected state. Further, in various arrangements, the transfer adapter may be provided so that the front face of the seal member thereof is disposed in a recessed position within the second connection port thereof when the second connection port is in a disconnected state.

In further relation to the described system aspect, a vial adapter may be included that is manipulable for selective interconnection to and non-manipulatable for disconnection from a vial, wherein a connection port of a vial adapter is selectively interconnectable to and disconnectable from the second connection portion port of the transfer adapter. Alternatively, or additionally, the system may include a reservoir adapter that is manipulatable for selective interconnecting to a non-manipulatable for disconnection from a reservoir, wherein a connection port of the reservoir adapter is selectively interconnectable to and disconnectable from the second connection port of the transfer adapter. The vial adapter and/or reservoir adapter may include a tubular member and a seal member adapted to include one or more features analogous to those described hereinabove in relation to the patient connector for analogous operative interface with the transfer adapter.

Various inventive apparatus are also contemplated by the present invention. In particular, a vial interconnection apparatus may be provided that includes a housing, a tubular member supportively interconnected to and extending though at least a portion of the housing along an axis thereof. The apparatus further includes a first connection port for receiving a top end of a vial, wherein an end of the tubular member may be located to penetrate a seal member at a top end of a vial upon positioning of the top end within the first connection port. Further in this regard, the first connection port of the apparatus may include at least one cantilevered member having a free end portion that extends inward towards and laterally about the axis, wherein the free end portion is elastically deflectable laterally outward and back inward relative to the housing axis upon contact with and advancement relative to a top end of a vial in the first connection port so as to provide a snap-fit engagement therewith. In some embodiments, the at least one cantilevered member may be provided so that, upon snap-fit engagement with a protruding lip at the top end of a vial (e.g. an annular lip projecting outward and away from a center axis of the vial), the vial connection apparatus is not disconnectable from the vial.

In certain arrangements, the first connection port of the vial interconnection apparatus may include a plurality of cantilevered members (e.g. spaced about the housing axis) and each having a free end portion extending inward towards and laterally about the axis, wherein the free end portions of each of the cantilevered members may be elastically deflectable to combinatively provide snap-fit engagement with a lip at a top end of a vial. In one embodiment, each of the cantilevered members may include a supported end located radially outward relative to the corresponding free end portion thereof.

Alternatively or additionally, each of the cantilevered members may be of an arcuate configuration. In this regard, each of a plurality of cantilevered members may be provided to spiral outward relative to the housing axis from the free end to the supported end thereof. In certain implementations, a free end portion of each of a plurality of cantilevered members may include a side surface portion that faces inward and is angled upward and towards the housing axis and tubular member, wherein the angled side surfaces combinatively define portions of an inverted cone configuration.

In some embodiments, a free end portion of each of a plurality of cantilevered members may include a top surface portion for engaging a lip at a port of a vial upon snap-fit engagement therewith, wherein the top surface portion may be arcuately offset relative to the corresponding supported end. The top surface portions may be provided to engage a downward facing surface portion or aspect of a protruding lip at a top end of a vial within a plane that is substantially normal to the housing axis.

As may be appreciated, the vial connection apparatus may include a second connection port for selective interconnection with a transfer adapter having one or more features described hereinabove. In this regard, the described vial connection apparatus may be provided to comprise one or more of the above-described vial adapter features for operative interface with a transfer adapter.

In a further aspect, a fluid reservoir interconnection apparatus may be provided that includes a housing, a tubular member supportively interconnected to and extending through at least a portion of the housing along an axis thereof, and a first connection port for receiving a port of a fluid reservoir therewithin, wherein an end of the tubular member may be located to penetrate a seal member of a fluid reservoir port upon positioning the reservoir port within the first connection port. Further, the fluid reservoir interconnection apparatus may include at least a first interconnection member having a first end supportably interconnected to the first connection port and a second end that is laterally advanceable toward the housing axis to restrainably engage a fluid reservoir port that is positioned within the first interconnection port.

The first end of the first interconnection member may be hingedly interconnected to the first connection port. In certain implementations, a locking member may be included wherein the first interconnection member may be selectively maintainable in a closed position relative to the first connection port. In some embodiments a locking arrangement may be provided so that upon connection of the fluid reservoir interconnection apparatus to a fluid reservoir port the apparatus is not disconnectable therefrom.

In one approach, the first interconnection member may include one of a lock member and a lock aperture for receiving the lock member, wherein the first connection port includes the other one of the lock member and the lock aperture. In turn, when the interconnection member is in the closed position the lock member and the lock aperture may operatively interface to non-releasably lock the interconnection member in the closed position (e.g. interconnected to the port of a fluid reservoir).

In certain arrangements, the first interconnection member may include a laterally extending flange member having an edge surface (e.g. a concave edge surface) for engaging a fluid reservoir port within the first connection port. Relatedly, the flange member may be elastically deflectable to apply a loading force to a fluid reservoir port that is positioned (e.g. locked) within the first connection port.

In a further related aspect, the reservoir connection apparatus may include a second interconnection member having a first end supportably connected to the first interconnection port and a second end laterally advanceable toward the housing axis to restrainably engage a fluid reservoir port positioned within the first connection port. In this regard, the first and second interconnection members may be disposed in opposing relation relative to the first connection port and may each be hingedly interconnected to the first connection port. Further, the second interconnection member and first connection port may include complimentary lock member and/or lock aperture features as described above. Further, the second interconnection member may include a flange member including one or more of the feature as described hereinabove.

As may be appreciated, the reservoir interconnection apparatus may include a second connection port for selective interconnection with a transfer adapter having one or more of the features described hereinabove. In this regard, the described fluid reservoir interconnection apparatus may be provided to comprise one or more of the above-described reservoir adapter features for operative interface with a transfer adapter.

The present invention further comprises various methods for handling a medical liquid. In one aspect, a method is provided that includes the steps of interconnecting a first connection port of a transfer adapter to a male luer fitting of a needleless syringe, and connecting a second connection port of the transfer adapter alternately (i) to a vial adapter fluidly interconnected to a vial containing a drug to automatically define a first fluid passageway, and (ii) to a reservoir adapter fluidly interconnected to a reservoir containing a medical liquid to automatically define a second fluid passageway. Of note, the connecting step may be completed while maintaining the interconnection between the first connection port of the transfer adapter and the male luer fitting of the needleless syringe. The method may further include the steps of manipulating the syringe to contain a liquid drug therewithin during the connecting step, securing a patient connector to a male luer fitting of an intravascular catheter access port, and passing at least a portion of the liquid drug into the patient connector (e.g. for delivery to a patient).

In certain embodiments, the needleless syringe may be fluidly interconnected to the vial adapter and to the reservoir adapter in the above-noted connecting step. In such embodiments, the method may further include the steps of interconnecting the second connection port of the transfer adapter to the patent connector to automatically define a third fluid passageway, while maintaining the interconnection between the first connection port of the transfer adapter and the male luer fitting of the needleless syringe. In this regard, the passing step may include flowing at least a portion of the liquid drug from the syringe though the transfer adapter to the patient connector (e.g., for administration to a patient).

In certain implementations, at least some of the liquid drug may be flowed from the syringe into the fluid reservoir during the connecting step, wherein the method may further include interconnecting a first connection port of another transfer adapter to a male luer fitting at a port fluidly interconnected by a tubing line to the fluid reservoir. Additionally, the method may include connecting a second connection port of the another transfer adapter to the patient connector, wherein the passing step includes flowing a portion of the liquid drug through the tubing line and another transfer adapter to the patient connector (e.g. for administration to a patient).

In a further aspect, the method may include attaching the vial adapter to the vial. In certain arrangements, the vial adapter may be non-detachable from the vial after attachment thereto. The vial adapter may be provided to include a tubular member, wherein the attaching thereto step includes penetrating one end of the tubular member through a seal member at a port of the vial to establish fluid interconnection between the vial adapter and the vial. Further in this respect, the transfer adapter may include a tubular member, wherein the connecting step includes fluidly interconnecting another end of the tubular member of the vial adapter and an end of the tubular member of the transfer adapter.

In conjunction with the vial attachment, the vial adapter may be linearly advanced relative to a port of the vial, wherein a snap-fit engagement is realized. In this regard, linear advancement step may entail engaging an end portion of at least one cantilevered member of a vial adapter with an outwardly protruding lip of a port of the vial, wherein the end portion elastically deflects about the lip and into snap-fit engagement with the vial.

In another aspect, the method may include attaching the reservoir adapter to a reservoir containing a medical liquid. In certain arrangements, the reservoir adapter may be non-detachable from the fluid reservoir after attachment thereto. In conjunction with reservoir adapter attachment, one end of the tubular member of the reservoir adapter may penetrate through a seal member provided at a port of the fluid reservoir to establish the fluid interconnection between the reservoir adapter and the fluid reservoir. Further in this regard, the transfer adapter may include a tubular member, wherein the connecting step comprises fluidly interconnecting another end of the tubular member of the reservoir adapter and an end of the tubular member of the transfer adapter.

In one arrangement, reservoir adapter attachment may include the steps of positioning a port of the fluid reservoir within a connection port of the reservoir adapter, and advancing at least one interconnection member of the reservoir adapter relative to the connection port thereof to retain the port of the fluid reservoir within the connection port of the reservoir adapter. In this regard, the method may further include locking the interconnection member into a fixed position in relation to the connection port of the reservoir adapter, wherein the reservoir adapter is non-detachable from the fluid reservoir port after the locking step.

In yet a further aspect, an inventive method is provided that includes the steps of interconnecting a first connection port of a transfer adapter to a male luer fitting of a needleless syringe, connecting a second connection port of the transfer adapter to a connection port of at least one of a vial adapter interconnectable to a vial and a reservoir adapter interconnectable to a fluid reservoir, wherein an end of a tubular member comprising the transfer adapter is fluidly interconnected with an end of a tubular member comprising the at least one of a vial adapter and a reservoir adapter. The method may further include the step of disconnecting the second connection port of the transfer adapter from the at least one of a vial adapter and a reservoir adapter, wherein the end of the tubular member and the transfer adapter is automatically, sealably enclosed upon such disconnection.

In one aspect, the above-noted interconnecting step may include manipulating a first member of the transfer adapter to establish the interconnection, wherein the first member is non-manipulatable to disconnect the transfer adapter from the needleless syringe after interconnection thereto. In another aspect, an end of the tubular member of the at least one of a vial adapter and a reservoir adapter may be automatically sealably enclosed upon disconnection of the second connection port of the transfer adapter therefrom.

In certain embodiments, the second connection port of the transfer adapter may be interconnected to a vial adapter in the connecting step, and the method may further include attaching a first connection port of the vial adapter to a vial, wherein the vial adapter is non-detachable from the vial after attachment thereto. In this regard, the attaching step may include linearly advancing the vial adapter relative to the vial, wherein a snap-fit attachment therebetween is achieved.

In other embodiments, the second connection port of the transfer adapter may be connected to a reservoir adapter in the connecting step, wherein the method may further include attaching a first connection port of the reservoir adapter to a port of a fluid reservoir by manipulating at least one interconnection member of the reservoir adapter, and wherein the at least one interconnection member is non-manipulatable to detach the reservoir adapter from the fluid reservoir port after attachment thereto. In this regard, the attaching step may include positioning the fluid reservoir port within the first connection port of the reservoir adapter in a first position relative thereto, and laterally advancing the at least one interconnection member towards the fluid reservoir port while maintaining the port in the first position, wherein the first interconnection member is operable to maintain the fluid reservoir port in the first relative position.

In a further related aspect, the at least one of a vial adapter and reservoir adapter may include at least one seal member for automatically sealably enclosing the end of the tubular member thereof upon disconnection from the transfer adapter, wherein the seal member is displaceable relative to and biased (e.g. spring-loaded) towards the connection port of the at least one of the vial adapter and reservoir adapter. In the later regard, the at least one seal member may automatically close the connection port of the at least one of a vial adapter and a reservoir adapter upon disconnection.

In yet a further aspect, a method for handling a medical liquid may include the steps of interconnecting a first connection port of a patient connector to an intravascular catheter access port, wherein the patient connector includes a second connection port that automatically closes in a disconnected state, and connecting a transfer adapter to the second connection port of the patient connector. The method may further include the steps of passing a first medical liquid through the transfer adapter and interconnected patient connector and interconnected vascular catheter access port, and attaching a male luer fitting of a first needleless syringe to the second connection port of the patient connector.

In one aspect, the method may further include the step of flowing a second medical liquid from the needleless syringe through the attached patient connector and interconnected intravascular catheter access port. In one embodiment, the flowing step may include flushing the intravascular catheter access port with the second medical liquid. In this regard, the flushing step may be completed at least once after the step of passing a first medical liquid through the transfer adapter and interconnected patient connector and interconnected intravascular catheter access port.

In various implementations, the method may further include the step of utilizing the needleless syringe, as attached to the intravascular catheter access port, to confirm patency of a vascular catheter interconnected to the intravascular access port and to a patient. In this regard, the utilizing step may be completed prior and/or after said first medical liquid passing step.

In a further aspect, the step of passing a first medical liquid through the transfer adapter and interconnected patient connector and intravascular catheter access port may include attaching a first connection port of the transfer adapter to a male luer fitting of one of a needleless syringe containing the first medical liquid and an infusion tubing line port fluidly interconnected to a reservoir containing the first medical liquid. Further in this regard, the connecting step may include securing a second connection port of the transfer adapter to the second connection port of the patient connector. In turn, the patient connector may include a seal member for automatic closure of the second connection port thereof, wherein the method may further include the step of disinfecting the front face of the seal member of the patient connector immediately prior to the securing step. Further, the method may include the step of disinfecting the front face of the seal member of the patient connector immediately prior to the step of attaching the first connection port of the transfer adapter to a male luer fitting of one a second needleless syringe and an infusion tubing line.

Numerous additional aspects and advantages of the present invention will be apparent to those skilled in the art upon consideration of the further description that follow.

BRIEF DESCRIPTION OF THE DRAWINGS

FIG. 6A is a side view of another embodiment of a vial adapter.

FIG. 6B is a cross sectional view of the vial adapter embodiment of FIG. 6A taken along line AA thereof.

FIG. 6C is an exploded assembly view of the vial adapter embodiment of FIGS. 6A and 6B.

FIGS. 7A, 7B, 7C, 7D and 7E illustrate a patient connector embodiment and a transfer adapter embodiment as employed in steps of method embodiments for administering a liquid drug from a needleless syringe or from a port of an infusion tubing set via an intravascular catheter access port.

FIGS. 10A, 10B and 10C are cross sectional views of a vial adapter embodiment and a vial in progressive stages of interconnection.

FIGS. 11A, 11B, 11C, 11D, 11E, 11F and 11G illustrate a reservoir adapter embodiment and a transfer adapter embodiment as employed in steps of a method embodiment for transferring a medical liquid between a fluid reservoir and a needleless syringe.

DETAILED DESCRIPTION OF THE DRAWINGS

System, apparatus and method embodiments comprising the present invention will now be described. As will become apparent to those skilled in the art, the various features of the invention are not limited to the described implementations.

Figure 1:
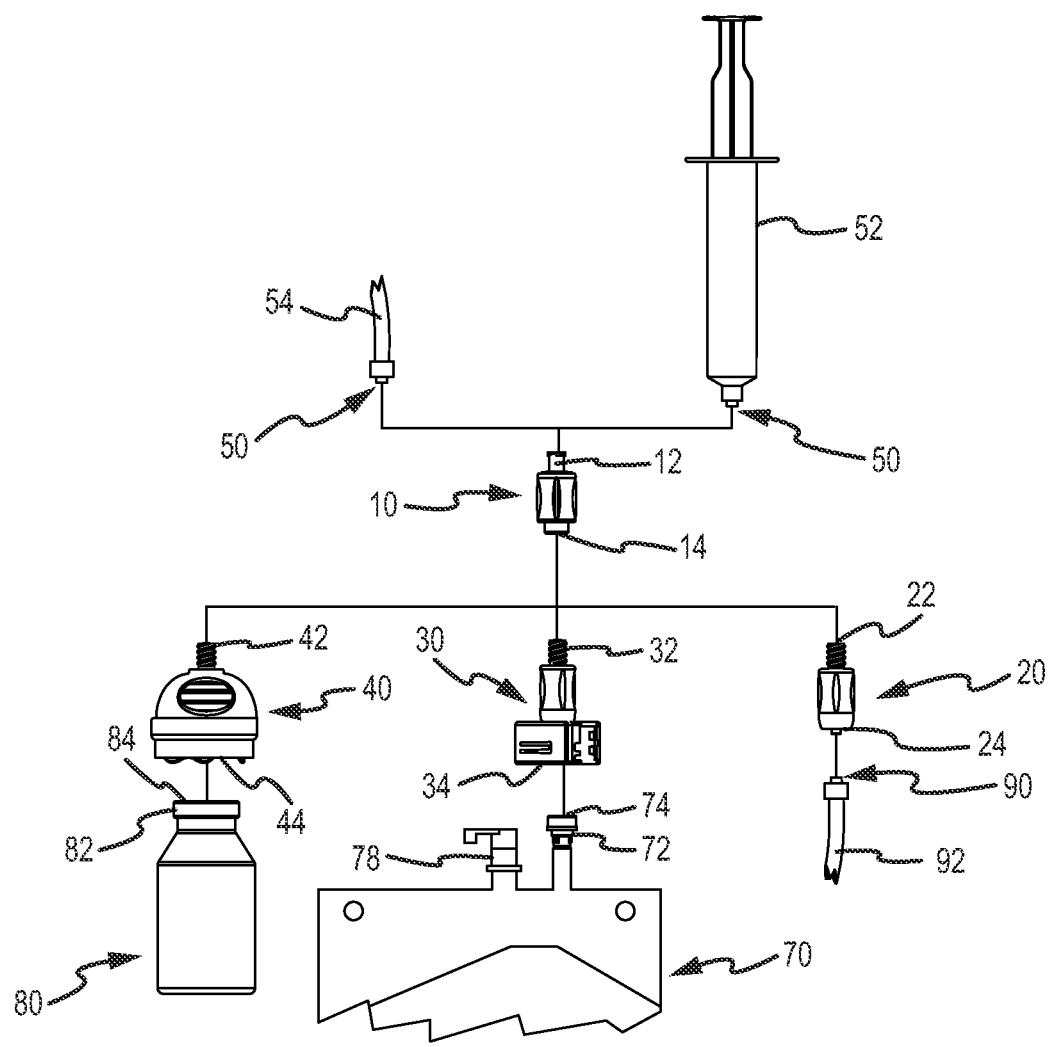
FIG. 1. is a schematic illustration of one embodiment of a liquid drug handling system.

As shown in the schematic illustration of FIG. 1, an exemplary liquid drug handling system may include at least a first transfer adapter 10, a patient interface connector 20, a reservoir adapter 30 and/or a vial adapter 40. The transfer adapter 10 may include a connection port 12 to interface with a male luer fitting 50, e.g. a conventional male luer fitting of a needleless syringe 52 or a conventional male luer fitting of a port of an infusion tubing line set 54, e.g. a tubing line set interconnected or interconnectable to a fluid reservoir containing a medical liquid). The transfer adapter 10 may also include a connection port 14 to alternately interface with any selected one of a compatible connection port 22 of the patient interface connector 20, a compatible connection port 32 of the reservoir adapter 30 or a compatible connection port 42 of the vial adapter 40.

The patient interface connector 20 may also include a connection port 24 to interface with a female luer fitting 90, e.g. a conventional female luer fitting of an intravascular catheter access port 92. Reservoir adapter 30 may further include a connection port 34 to interface with a fluid reservoir 70, e.g. via a reservoir port 72 having at least one pierceable seal member 74. By way of example, the fluid reservoir 70 may contain a saline solution, a dextrose solution or any other medical liquid employable as a diluent for, reconstitution of, or otherwise in combination with a drug.

In the later regard, the vial adapter 40 may further include a connection port to interface with a vial 80 containing a drug, e.g. via an enlarged, or lipped, top end port 82 having a pierceable seal member 84. By way of example, the vial 80 may comprise a drug in a liquid form for direct administration, in a concentrate form that may be diluted with a medical liquid prior to administration (e.g. a medical liquid contained in fluid reservoir 70), in a powder form that may be reconstituted with a medical liquid prior to administration (e.g. a medical liquid contained in fluid reservoir 70), or in a drug constituent form otherwise employable for mixture with one or more other drug constituent(s).

As may be appreciated, the transfer adapter 10, patient interface connector 20, reservoir adapter 30 and vial adapter 40 may be provided with features that are particularly apt for use in handling liquid drugs of a hazardous nature, e.g. antineoplastic, cytotoxic, biologic, antiviral and immunosuppressive agents. More particularly, the noted components may be provided for handling hazardous drugs in a closed-system manner, wherein one or more of the system components may be attachable to and non-detachable from a conventional drug containment vessel(s) and/or may otherwise be interconnectable to and sealably disconnectable from other system components.

In the former regard, the transfer adapter 10, reservoir adapter 30 and vial adapter 40 may each be provided with interconnection features that are intended to restrict disconnection of the transfer adapter 10, reservoir adapter 30 and vial adapter 40 from a standard male luer fitting 50 (e.g. of a conventional needleless syringe 52 or a port of conventional infusion tubing line set 54), a fluid reservoir 70, and a vial 80, respectively, after initial interconnection therewith. Further, the transfer adapter 10, patient interface connector 20, reservoir adapter 30 and vial adapter 40 may each be provided with features to selectively define and automatically sealably close fluid passageways therebetween. Additionally, the connection port 22 of the patient connector 20, the connection port 32 of reservoir adapter 30 and/or the connection port 42 of vial adapter 40 may be configured for interconnection with a standard male luer fitting, e.g. as employed on a conventional needless syringe and/or port of a conventional infusion tubing set.

Reference is now made to FIGS. 2A-2E which illustrate an embodiment of a transfer adapter 100. The transfer adapter 100 may include a first housing 110 defining a first connection port 112, and a second housing 120 defining a second connection port 122. A protective cap 102 may be initially provided at the second connection port 122 and removed prior to use of the transfer adapter 100.

In this embodiment, the first connection port 112 may comprise external threads 114 sized for rotatable interconnection of the port 110 with a male luer fitting, e.g. a male luer fitting of a conventional needleless syringe or a male luer fitting at a port of a conventional infusion tubing line set. Further, the second connection port 122 may include internal threads 124. As will be further described, the second connection port 122 and internal threads 124 thereof may be sized for selective and alternative interconnection with and disconnection from complimentary ports of a patient interface connector, a reservoir adapter and/or a vial adapter included within a liquid drug handling system embodiment.

The transfer adapter 110 may include a tubular member 130 that extends along a longitudinal axis AA through a portion of the second housing 120. The tubular member 130 defines a fluid passageway that extends from connection port 112 to one end 132 of the tubular member 130. In the illustrated embodiment, the tubular member 130 is integrally defined as a part of the first housing 110. In other embodiments, the tubular member 130 may be defined by a separate member fixedly interconnected to the first housing 110.

The second housing 120 and first housing 110 may be interconnected for co-rotative movement in a first direction and for relative rotative movement in a second direction. For example, the second housing 120 may be manipulated to rotate in a first direction (e.g. in a clockwise direction) and thereby co-rotate the first housing 110 (e.g. in a clockwise direction) to realize interconnection of the external threads 114 of first port 112 with internal threads of a male luer fitting, wherein after such an interconnection rotative manipulation of the second housing 120 in an opposite second direction (e.g. in a counter-clockwise direction) will not effect co-rotation/disconnection of the first housing 110 relative to/from the male luer fitting.

In this regard, the first housing 110 and second housing 120 may be operatively interfaced in a ratchet-like arrangement. For example, and as best shown in FIG. 2E, the tubular member 130 may be provided with a laterally-extending flange 140 having at least one and typically a plurality of arcuate portions 142 (e.g. four portions) each having a peripheral edge surface that spirals away from a longitudinal axis AA, wherein one and typically a plurality of a adjacent arcuate portions 142 are adjoined by one and typically a plurality of intermediate steps 144. In turn, and as shown by FIG. 2D, one and typically a corresponding plurality of cantilevered, longitudinally-extending members 150 (e.g. four members) may be interconnected to or integrally defined by the second housing 120, wherein upon assembly the cantilevered members 150 may be aligned with and spaced around longitudinal axis AA and oriented transversely to and engageable with the peripheral edge surfaces of the arcuate portions 142 of the lateral flange 140.

More particularly, the cantilevered members 150 may each include an arcuate, inward-facing surface 152 and an adjoining, stepped-edge portion 154, wherein upon rotation of the second housing 120 in a first direction (e.g. clockwise rotation) the stepped-edge portions 154 of the longitudinally-extending members 150 abuttingly engage the intermediate steps 144 of the lateral flange 140 to co-rotate the first housing 110. Further, upon rotation of the second housing 120 in an opposite second direction, (e.g. counter-clockwise rotation), e.g. after interconnection of the first connection port 112 to a male luer fitting, the arcuate surfaces 152 of the cantilevered, longitudinally-extending members 150 may slidably and successively engage the spiral-shaped, peripheral edge surfaces of the arcuate portions 142 of the laterally-extending flange 140, wherein the cantilevered, longitudinal members 150 may successively deflect away from and spring-back towards the longitudinal axis AA, and wherein such rotation of the second housing 120 does not effect co-rotation of the first housing 110.

To facilitate rotative manipulation of the second housing 120 by a user, the outside surface of the housing 120 may be contoured for finger contact. For example, a plurality of concave, or dished, surface portions 128a may be provided, with raised rib portions 128b interposed therebetween. Such raised rib portions 128b may extend in aligned relation to the axis longitudinal axis AA and may be peripherally disposed at a greater distance from the axis AA than the balance of the second housing 120, wherein such rib portions 128b restrict rolling of the transfer adapter 100 when placed on a support surface.

Figure 2A:
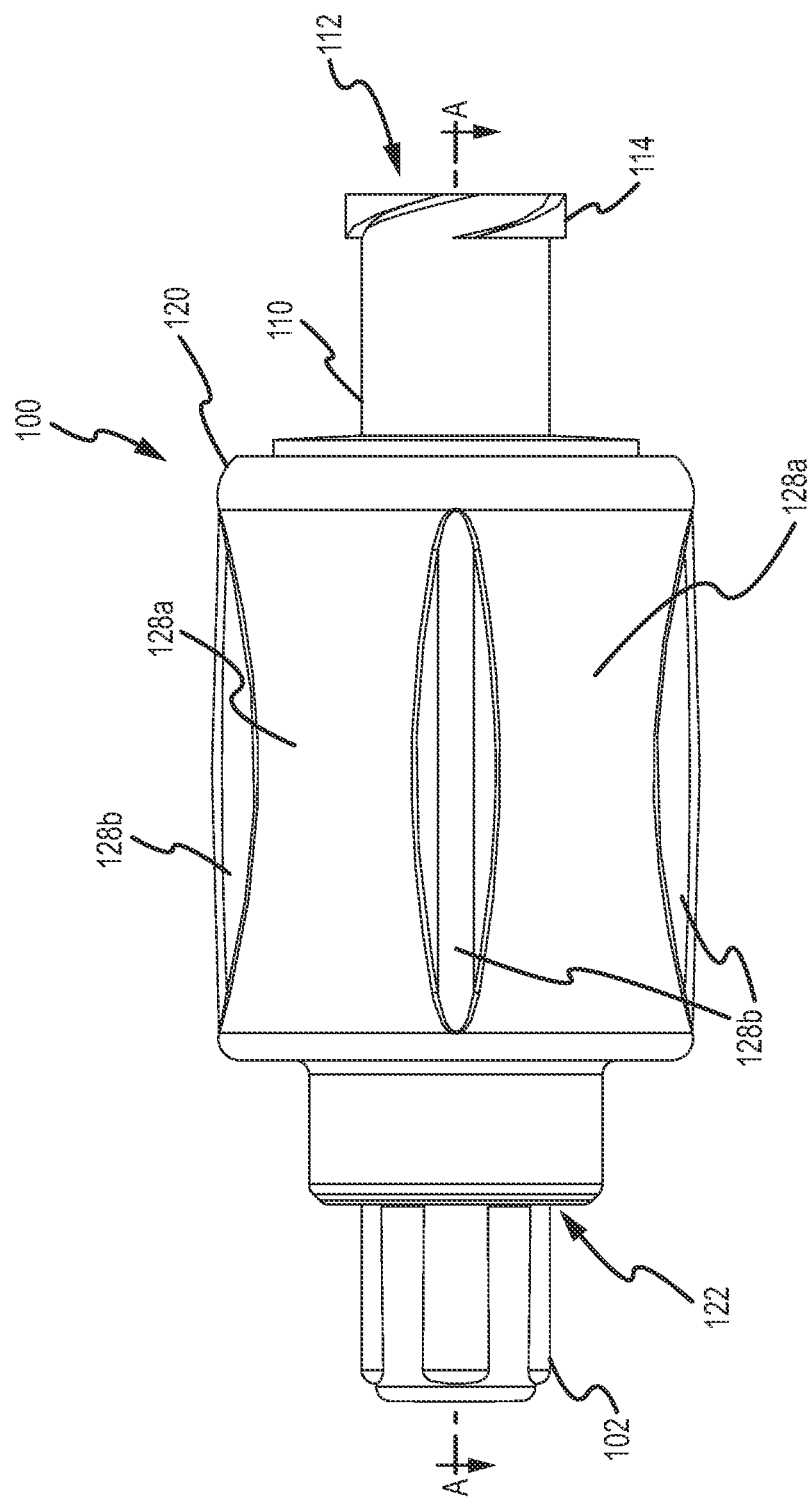
FIG. 2A is a side view of one embodiment of a transfer adapter.
Figure 2B:
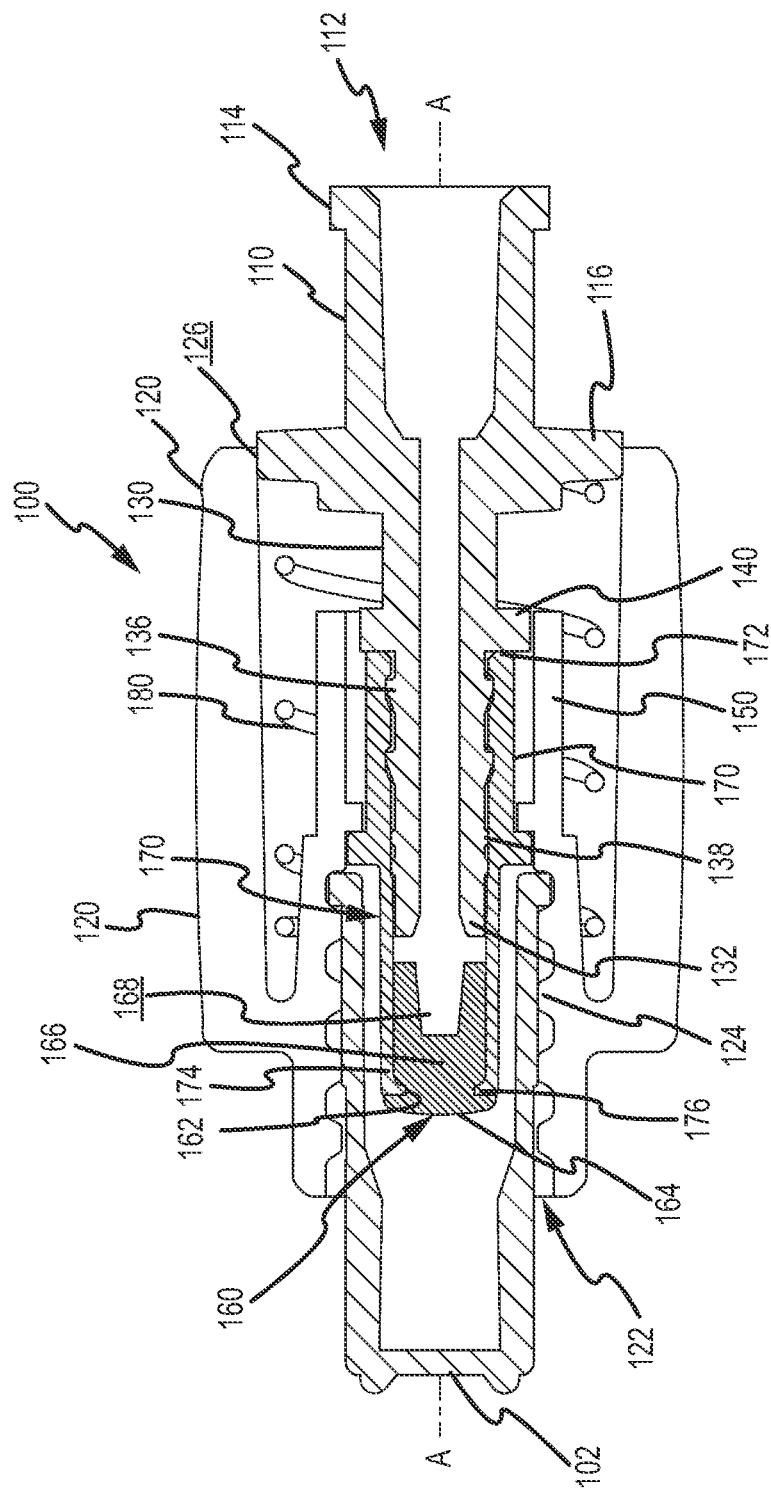
FIG. 2B is a cross sectional view of the transfer adapter embodiment of FIG. 2A taken along line AA thereof.
Figure 2C:
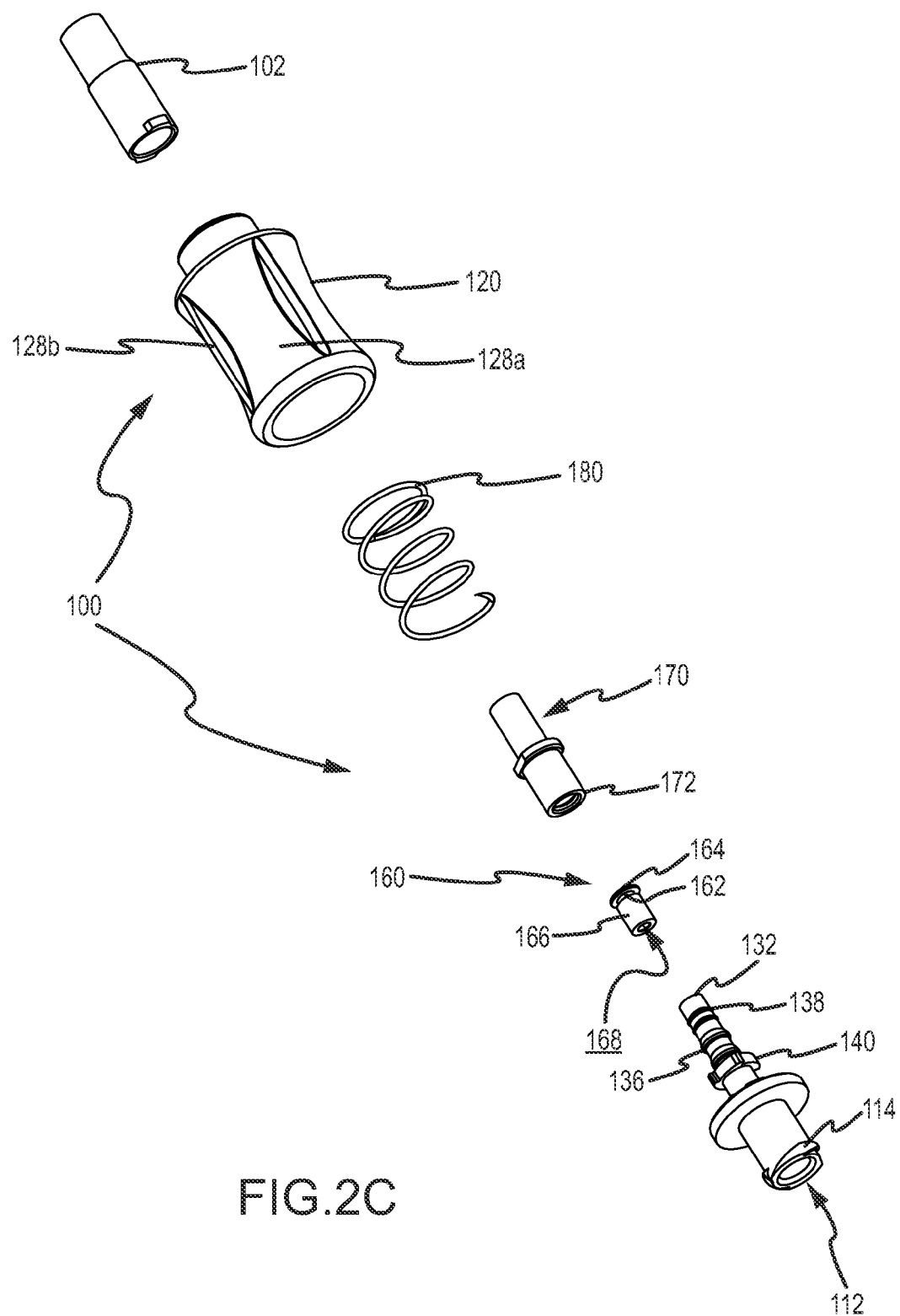
FIG. 2C is an exploded assembly view of the transfer adapter embodiment of FIGS. 2A and 2B.
Figure 2D:
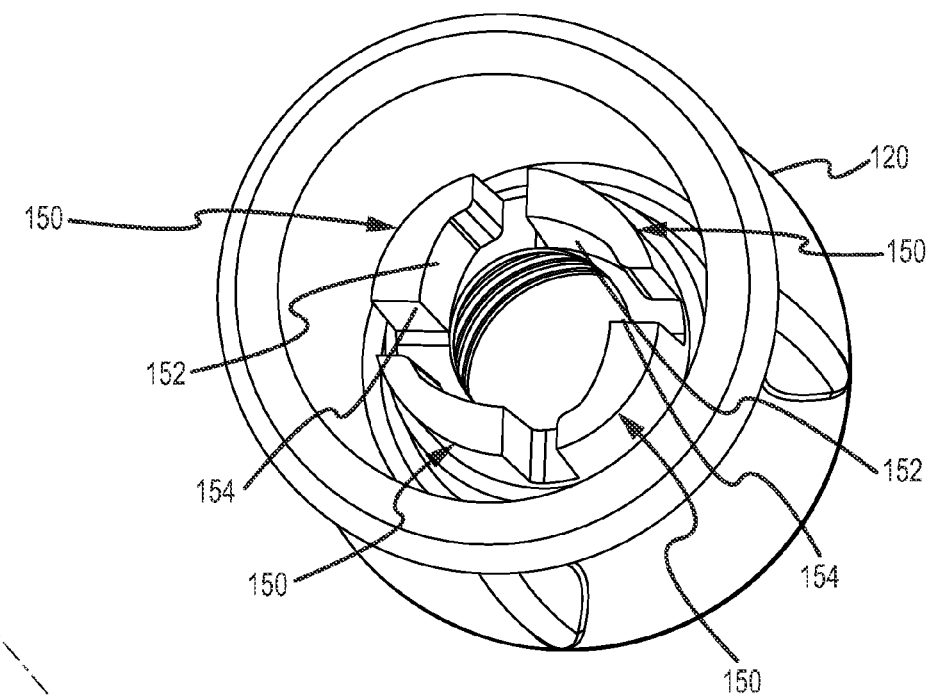
FIG. 2D is a perspective view of a housing comprising the transfer adapter embodiment of FIGS. 2A-2C.
Figure 2E:
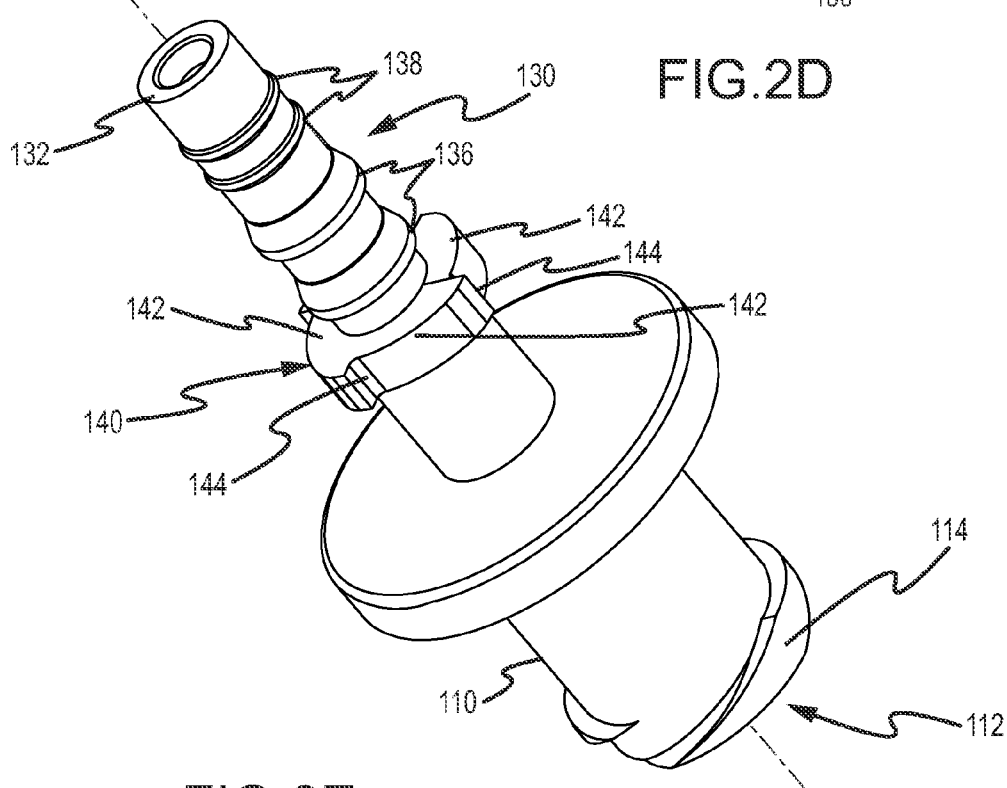
FIG. 2E is perspective view of another housing comprising the transfer adapter embodiment of FIGS. 2A-2C.

In further relation to the transfer adapter 100 embodiment shown in FIGS. 2A-2E, a seal member comprising a resilient septum 160 and tubular sleeve 170 arrangement may be provided to sealably enclose the end 132 of the tubular member 130. In this regard, and as best shown by FIG. 2B, the end 132 of and an adjoining portion of the tubular member 130 may sealably extend into the tubular sleeve 170 at one end 172 thereof. In turn, the resilient septum 160 may be retainably interconnected to and sealably engage another end 174 of the tubular sleeve 170. More particularly, the resilient septum 160 may include a peripheral, annular recess 162 for receiving an inwardly-extending, annular end flange 176 of the tubular sleeve 170, wherein a front face portion 164 of the resilient septum 160 may be disposed outside of the tubular sleeve 170 and a body portion 166 of the resilient septum may be disposed within the tubular sleeve 170.

As noted, the end 132 and adjoining portion of the tubular member 130 may be internally and sealably disposed within the end 172 of the tubular sleeve 170. In this regard, the outside surface of the internally disposed portion of the tubular member 130 and the inside surface of the tubular sleeve 170 may be sized and/or otherwise contoured to provide a seal therebetween. For example, the two components may have interfacing surfaces with external and internal diameters, respectively, established to provide a mechanical interference therebetween. Further, one or a plurality of annular, angled, or barbed, lips 136 and/or annular rings 138 may project from and entirely around the tubular member 130 to further facilitate realization of a retainable, sealed interface between the tubular member 130 and sleeve 170. In one embodiment, one or more angled lips 136 may be provided on the tubular member 130 for snap-fit assembly with and receipt within corresponding annular recesses formed on an inside surface of the tubular sleeve 170 near the end 172 thereof.

As will be further addressed hereinbelow, the resilient septum 160 may be provided to receive a tubular member of another liquid drug handling system component forcibly advanced therethrough, wherein a closed fluid passageway may be established between the received tubular member, the tubular sleeve 170 and the tubular member 130 of the transfer adapter 100. In this regard, the septum 160 may be pierceable and/or pre-pierced (e.g. pre-pierced during manufacturing utilizing a needle having a closed, trocar point), or pre-cut (e.g. pre-cut via a laser during manufacturing) to facilitate forcible passage of a tubular member therethrough, and may further include a frusto-conical cavity 168 disposed in opposing relation to the receiving end 132 of the tubular member 130.

As may be appreciated, the septum 160 may exhibit sufficient resiliency to sealably close upon withdrawal of a tubular member of another system component therefrom. By way of example, septum 160 may be integrally defined by a resilient material such as polyisoprene. Further, the body portion 166 and sleeve 170 may be sized so that the body portion 166 is in compression within sleeve 170, wherein sealable closure is facilitated.

The transfer adapter 100 may be further provided so that the first housing 110 and second housing 120 may be axially displaceable relative to one another. By way of example, the first housing 110 may be slidably displaceable to a predetermined extent within a portion of the second housing 120 towards the second connection port 122. More particularly, a flange 116 of the first housing 110 may be sized to fit within a coincidently configured aperture 126 located at an end of the second housing 120 that is opposite to the second interconnection port 122 thereof. The range of inward slidable displacement of first housing 110 may be limited by ends of the cantilevered, longitudinal members 150 comprising second housing 120. Relatedly, and as best illustrated by FIG. 2B, a spring member 180 may be internally captured between the second housing 120 and flange 116 of first housing 110 so as to bias the first housing 110 and interconnected tubular member 130 away from the second interconnection port 122.

In turn, and as shown in FIG. 2B, such biasing locates the front face portion 164 of septum 160 to a recessed position within the second connection port 122. When biased to the recessed position the front face portion 162 of septum 160 may be offset inwardly in relation to a distal end portion of the internal threads 124 provided at the second connection port 122, wherein a proximal end portion of the internal threads 124 may extend inwardly beyond the front face portion 162 of septum 160 in it's recessed position. As such, rotative interconnection between the connection port 122 and a port of another liquid drug handling system component may be advantageously initiated without encountering an opposing spring-force, as will be further addressed. Relatedly, by virtue of the biased, recessed positioning of the septum 160, the septum 160 may be beneficially internally located when penetrated by a tubular member of another system component, as noted above. Further, as a result of the noted biasing, the septum 160 may be advantageously located within the transfer adapter 100 during normal handling of the transfer adapter 100, thereby limiting user and other undesirable contact with the front face portion 164 of the septum 160. Relatedly, the protective cap 102 noted above may be initially provided to extend into the port 122 to shield the front face portion 164 of septum 160 and an outside surface portion of sleeve 170 from contamination prior to use.

Of further note, when the second port 122 is in a disconnected state, axial pressure may be applied to the first housing 110, e.g. via an interconnected needleless syringe interconnected to connection port 112, so as to overcome the spring-loading force. In turn, the front face portion 164 of septum 160 may be selectively advanced to a position flush with or beyond the port 122 and second housing 120, wherein the front face portion 162 may be selectively contacted for cleaning and/or disinfection purposes (e.g. with a swab having disinfectant thereupon).

Figure 3A:
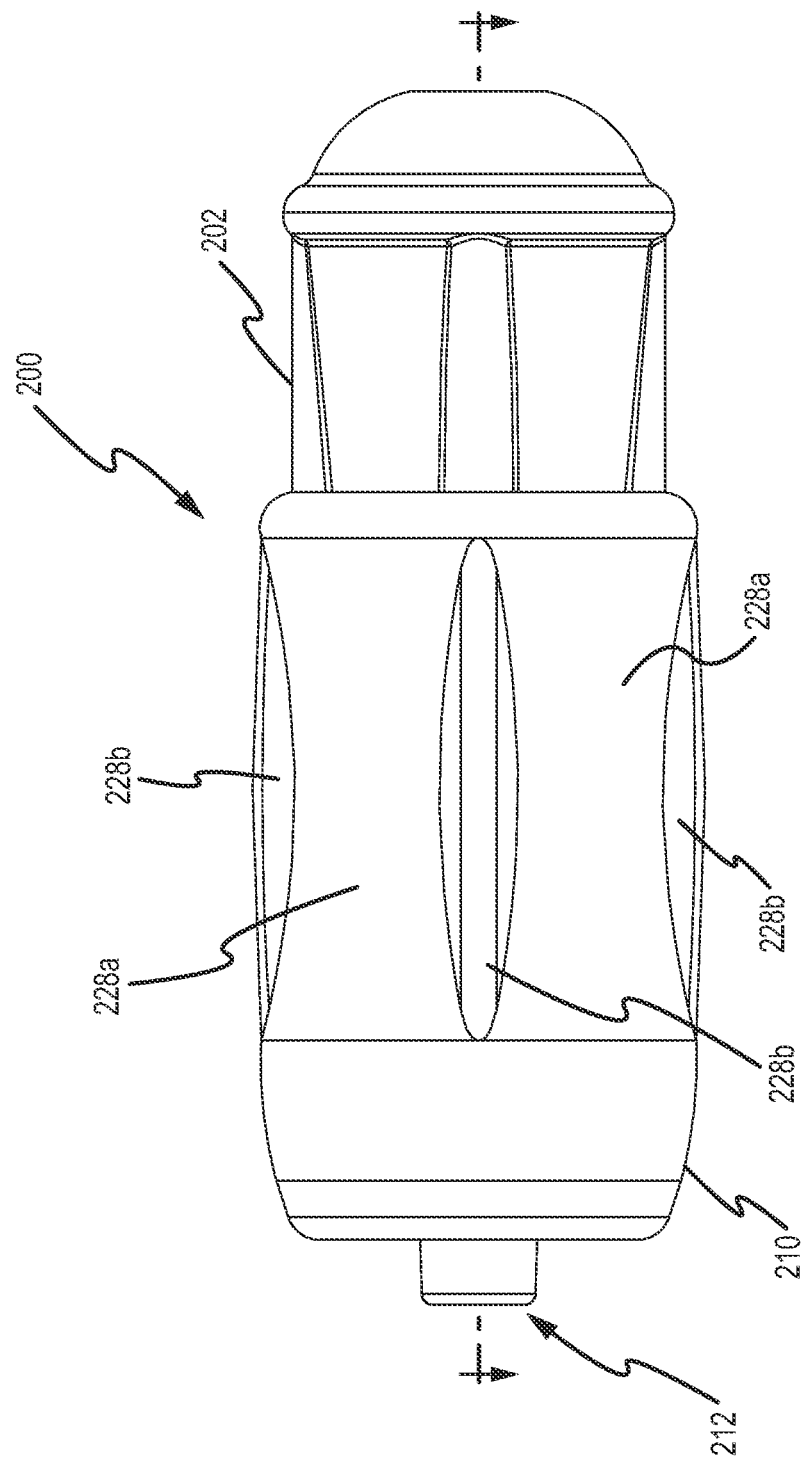
FIG. 3A is a side view of one embodiment of a patient connector embodiment comprising the present invention.
Figure 3B:
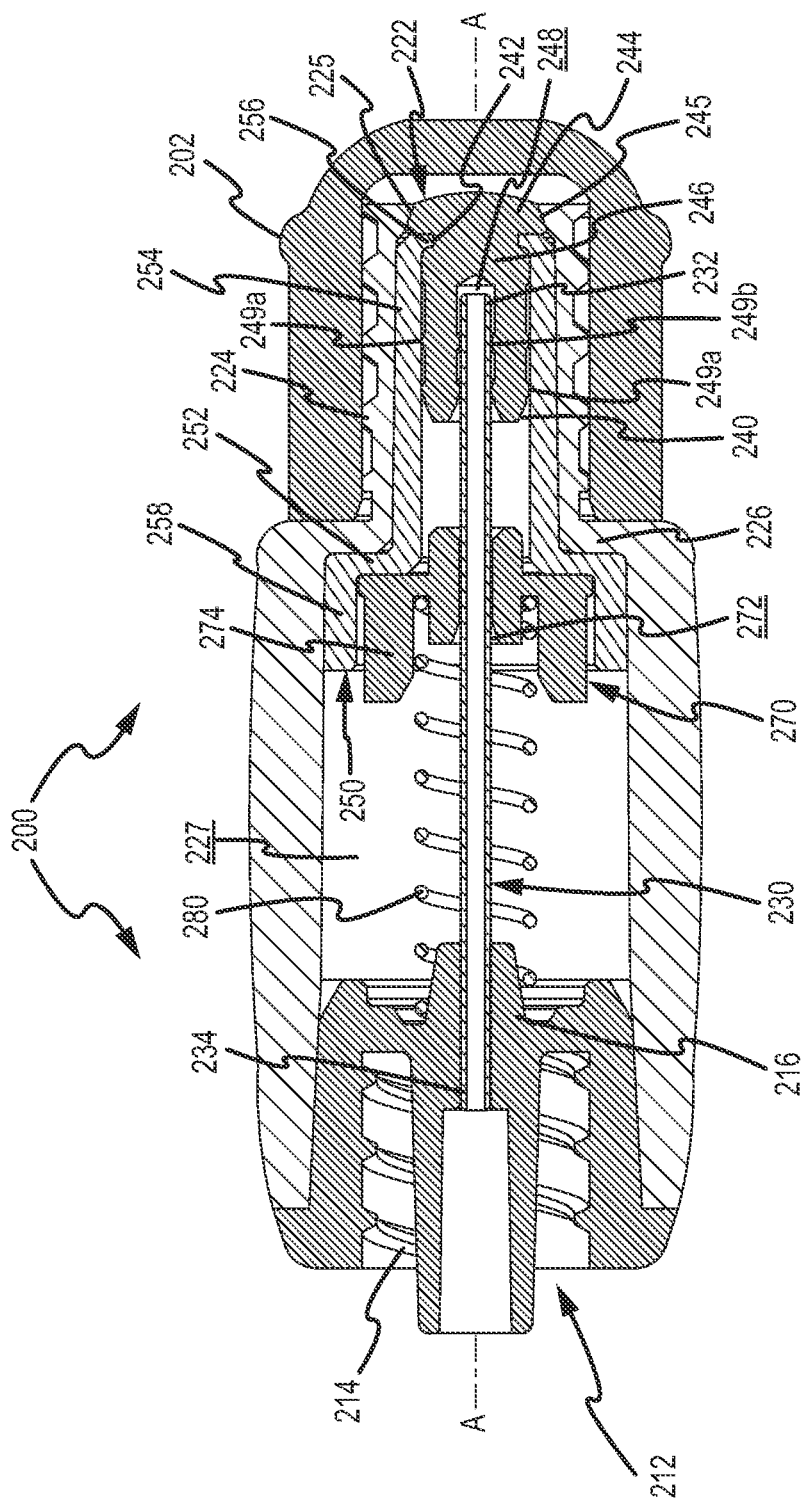
FIG. 3B is a cross sectional view of the patient connector embodiment of FIG. 3A taken along line AA thereof.
Figure 3C:
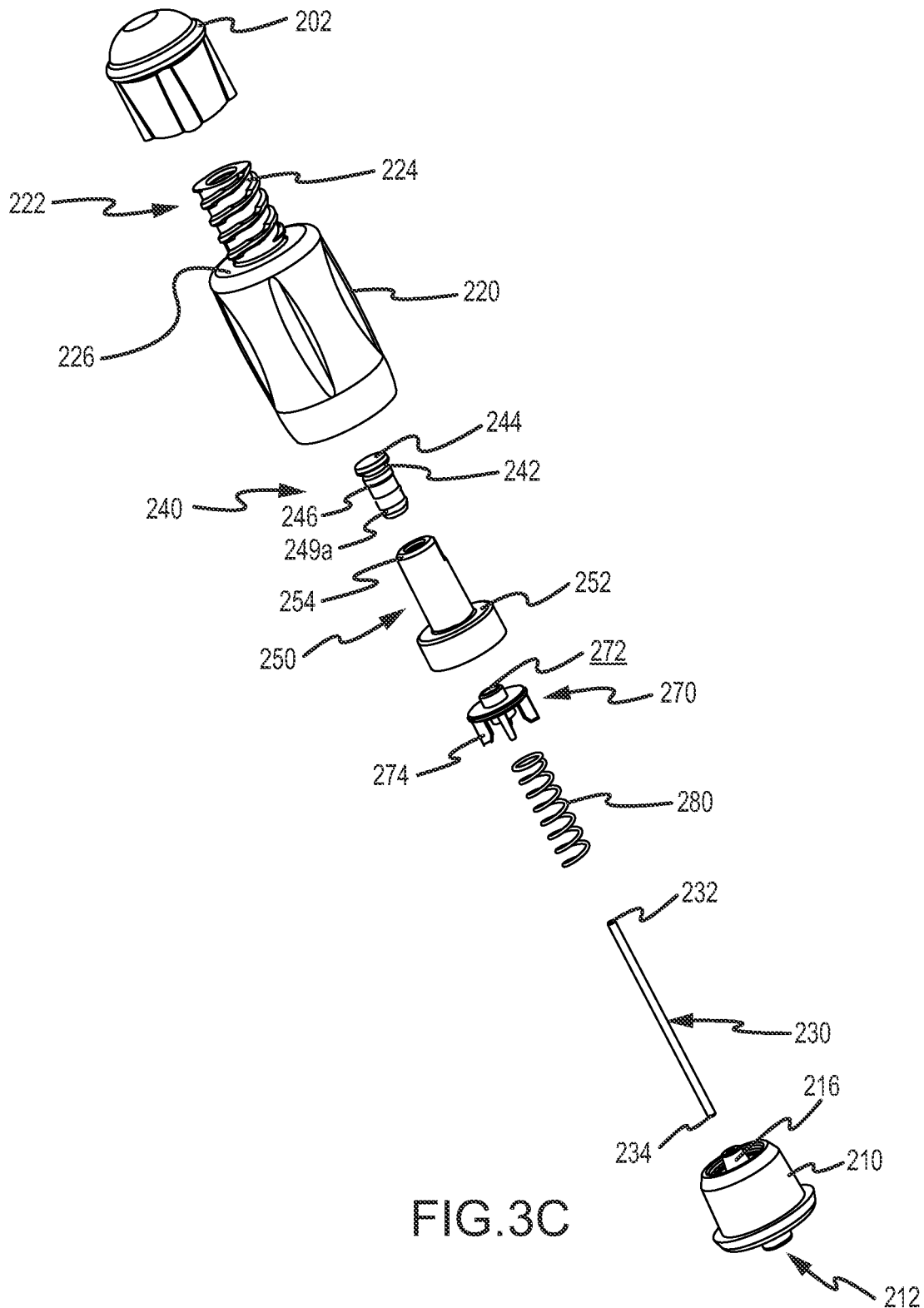
FIG. 3C is an exploded assembly view of the patient connector embodiment of FIGS. 3A and 3B.

Reference is now made to FIGS. 3A-3C, which illustrate an embodiment of a patient connector 200. Patient connector 200 may include a first housing 200 defining a first connection port 212, and a second housing 220 fixedly interconnected to the first housing 210 and defining a second connection port 222. A protective cap 202 may be initially provided with the patient connector 200 to cover and thereby shield the second connection port 222 (e.g. from contamination) and may be removed prior to use.

In this embodiment, the first connection port 212 may comprise internal threads 214 sized for rotatable interconnection of the port 212 with a female luer fitting, e.g. a female luer fitting utilized at an intravascular catheter access port. Further, the second connection port 222 may include external threads 224. The connection port 222 and external threads 224 thereof may be sized for selective interconnection with and disconnection from the second connection port 122 and internal threads 124 of the transfer adapter 100 described hereinabove.

The patient connector 200 may include a tubular member 230 that is fixedly interconnected at one end 234 to the first housing 210 and that extends along a longitudinal axis AA through a portion of the second housing 220. The tubular member 230 defines a fluid passageway that extends from the end 234 at connection port 212 to another end 232 of the tubular member 230. By way of example, the tubular member 230 may comprise a metal cannula fixedly received at a central bore 216 of the first housing 210.

To facilitate rotative manipulation of the second housing 220 by a user, the outside surface of the housing 220 may be contoured for finger engagement and corresponding rotative force application thereby. For example, a plurality of concave, or dished, surface portions 228a may be provided, with raised rib portions 228b interposed therebetween. Such raised rib portions 228b may extend in aligned relation to the axis longitudinal axis AA and may be peripherally disposed at a greater distance from the axis AA than the balance of the second housing 220, wherein such rib portions 228b restrict rolling of the patient connector 200 when placed on a support surface.

In relation to the patient connector 200 shown in FIGS. 3A-3C, a seal member comprising a resilient septum 240 and a carriage 250 may be provided to sealably enclose the end 232 of the tubular member 230 when the second connection port 222 is in a disconnected state. In this regard, and as best shown by FIG. 3B, the resilient septum 240 may be retainably and sealably interconnected at a tubular end 254 of the carriage 250. More particularly, the resilient septum 240 may include a peripheral, annular recess 242 for receiving an inwardly-extending annular end-flange 256 of the carriage 250, wherein a front face portion 244 of the resilient septum 240 may be disposed outside of the carriage 250 and a body portion 246 of the resilient septum may be disposed within the tubular end 254 of the carriage 250. In turn, the end 232 and an adjoining portion of the tubular member 230 may be sealably disposed within a receiving cavity 248 of the body portion 246 of the resilient septum 240.

In the later regard, the inside surface of the tubular end 254 of carriage 250 and the outside surface of the body portion 246 of the resilient septum 240 may be sized and/or otherwise contoured to facilitate a tight interface therebetween. Further, the outside surface of the end portion of the tubular member 230 that adjoins end 232, and the inside surface of the receiving cavity 248 of the body portion 246 of the resilient septum 240 may be sized and/or contoured to facilitate a tight interface therebetween. For example, the two components may have external and internal diameters established to yield mechanical interference therebetween. Further, the outside surface of body portion 246 and inside surface of cavity 248 of resilient septum 240 may be provided with outwardly-projecting rings 249a and inwardly-projecting rings 249b, respectively, sized to yield a mechanical interference with and otherwise compressively interface with the inside surface of the tubular end 254 of carriage 250 and outside surface of tubular member 230, respectively. In turn, sealable closure of the end 232 of tubular member 230 may be realized.

As will be further addressed hereinbelow, the second end 232 of the tubular member 230 may be provided to fluidly interface with the tubular member 130 of the transfer adapter 100 described hereinabove, wherein a closed fluid passageway may be established through the patient connector 200 and transfer adapter 100. In conjunction therewith, the resilient septum 240 may be pierceable and/or pre-pierced (e.g. pre-pierced during manufacturing utilizing a needle having a closed, pencil point, solid tip) or pre-cut (e.g. pre-cut via a laser during manufacturing) to facilitate the passage of the end 232 of the tubular member 230 therethrough, i.e. progressively from the cavity 248 through the body portion 246 and through the front face portion 244. Further in that regard, the resilient septum 240 and carriage 250 may be axially displaceable relative to the tubular member 230 and biased toward the second connection port 222.

More particularly, upon rotative interconnection of the second connection port 222 with the second connection port 122 of the transfer adapter 100, the front face 162 of the septum 160 of the transfer adapter 100 may engage the front face portion 244 of the septum 240 of the patient connector 200. In this regard, and as previously noted, the recessed biased-positioning of the septum 160 of the transfer adapter 100 facilitates initial rotative interconnection of the transfer adapter 100 and patient connector 200, since such initial interconnection may be achieved prior to engagement of the septum 160 with the septum 240. Upon further rotative interconnection, the front face 162 of septum 160 of the transfer adapter 100 may progressively advance in to the second port 222 so as to inwardly and forcibly displace the septum 240 and carriage 250 against a spring-loading force acting thereupon, thereby facilitating a sealed interface. In the later regard, carriage 250 may operatively interface with a hub-like guide 270, and a spiral spring 280 that biases the guide 270, carriage 250 and septum 240 toward the second connection port 220 of the patient connector 200.

As shown in FIG. 3B, the carriage 250 may include a shoulder portion 252 that may be biased towards and into abutting relation with a complimentarily shaped shoulder portion 226 of the second housing 220 when the second connection port 222 is in a disconnected state. In turn, the guide 270 may be sized to fit within an enlarged, cup-shaped end 258 of the carriage member 250 that slidably engages an internal surface of the second housing 220. A central bore 272 through the guide 270 may slidably receive the tubular member 230 therethrough. The guide 270 may further include a plurality of posts 274 for receiving and thereby locating an end of the spring 280 therebetween.

As may be appreciated, as the septum 240 and carriage 250 are inwardly displaced upon interconnection of the patient connector 200 with the transfer adapter 100, the end 232 of the tubular member 230 may forcibly pass, or penetrate, from the cavity 248 though the body 246 and front face portion 244 of the septum 240 of the patient connector 200, and then through the front face portion 164 and body 166 of the septum 160 of the transfer adapter 100 for receipt within the cavity 168 of the septum 160 in adjacent, face-to-face relation with the end 132 of the member 130 of the transfer adapter 100. In such position, a liquid drug may be passed between the tubular member 130 of transfer adapter 100 and tubular member 230 of patient connector 200. More particularly, a closed fluid passageway may be provided for liquid transfer between the first connection port 112 of transfer adapter 100 and the end 234 of the tubular member 230 at the first connector port 212 of the connector 200.

Upon rotative disconnection of the second connection port 220 of the patient connector 200 from the second connection port 120 of the transfer adapter 100, e.g. after transfer of a liquid drug between and through the transfer adapter 100 and patient connector 200, the end 232 of tubular member 230 may progressively pass back out of the septum 160 of the transfer adapter 100 and the septum 240 of the patient connector 200. In the later regard, the septum 240 may be sufficiently resilient so as to sealably close upon passage of the end 232 of tubular member 230 therefrom. By way of example, the septum 240 may be integrally defined by a resilient material such as polyisoprene.

As may be appreciated, upon disconnection of the patient connector 200 and transfer adapter 100, the end 232 of tubular member 230 passes out of septum 240 as the septum 240 and carriage 250 of the transfer adapter automatically advance relative to the tubular member 230 responsive to the spring-loading force provided by spring member 280. In conjunction with such movement, the septum 240 may automatically, sealably enclose the end 232 of the tubular member 230. Further, the front face portion 244 of the septum 240 may automatically close the second connection port 222. Additionally, a front surface of the front face portion 244 may be automatically disposed substantially flush with or outwardly beyond the end of the housing 220, thereby facilitating cleaning and/or disinfecting the front face portion 244.

In this regard, and in one approach, the front face portion 244 of the resilient septum 240 may comprise a tapered down, or beveled, peripheral end surface 245 sized to engage a complimentary tapered surface 225 provided at the end of the second connection port 222 of housing 220. Such engagement facilitates automatic closure of the second connection port 222 by the front face portion 244 of the septum 240 when the second connection port 222 is in a disconnected state.

Further in this regard, the front face portion 244 of the septum 240 may be provided to have a maximum cross-dimension (e.g. a maximum diameter) that is less than a minimum cross-dimension, (e.g. a minimum diameter) of an internal chamber 227 defined by the second housing 220 proximal to the tapered surface 225 thereof, wherein the septum 240 is spaced from and free from engagement with the second housing 220 when forcibly retracted during interconnection of the patient connector 200 with the transfer adapter 100 described hereinabove or when forcibly retracted upon engagement with a nozzle of a conventional male luer fitting during interconnection of the patient connector 200 with the male luer fitting. In the later regard, in certain implementations a nozzle in of a male luer fitting of a conventional needleless syringe or infusion tubing line port may sealably engage the front surface of the front face portion 244 of the spring-loaded septum 240, in a face-to-face manner upon interconnection of the patient connector 200 and needleless syringe or infusion tubing line port, and at the same time, the end 232 of the tubular member 230 may advance through the septum 240 to fluidly interface with the nozzle of the male luer fitting to facilitate liquid transfer therebetween.

Figure 4A:
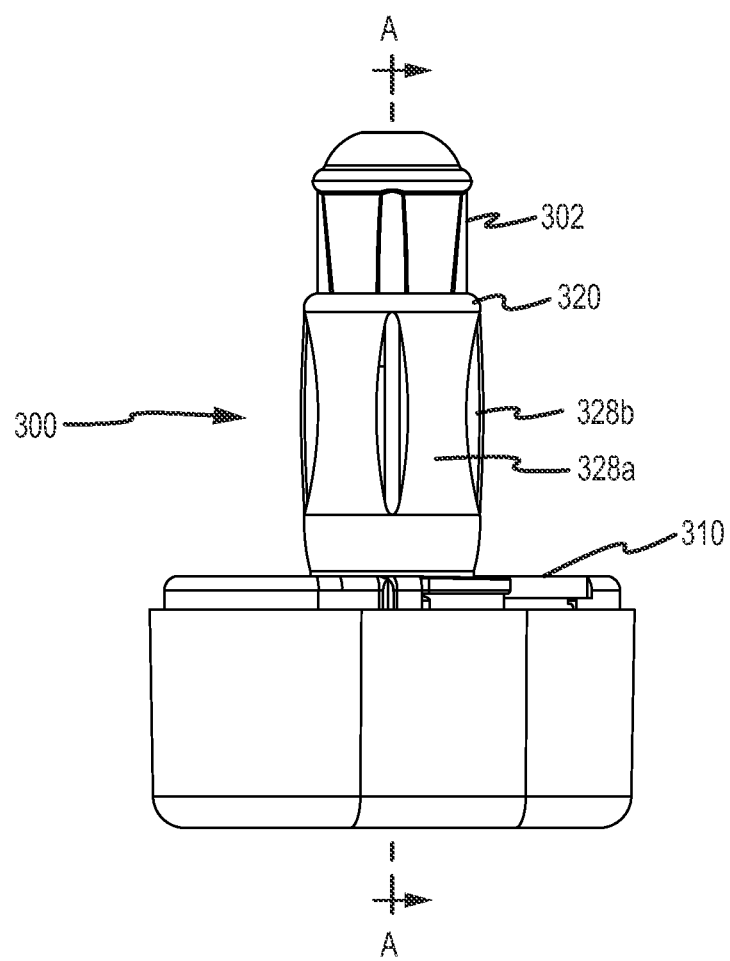
FIG. 4A is a side view of one embodiment of a fluid reservoir adapter.
Figure 4B:
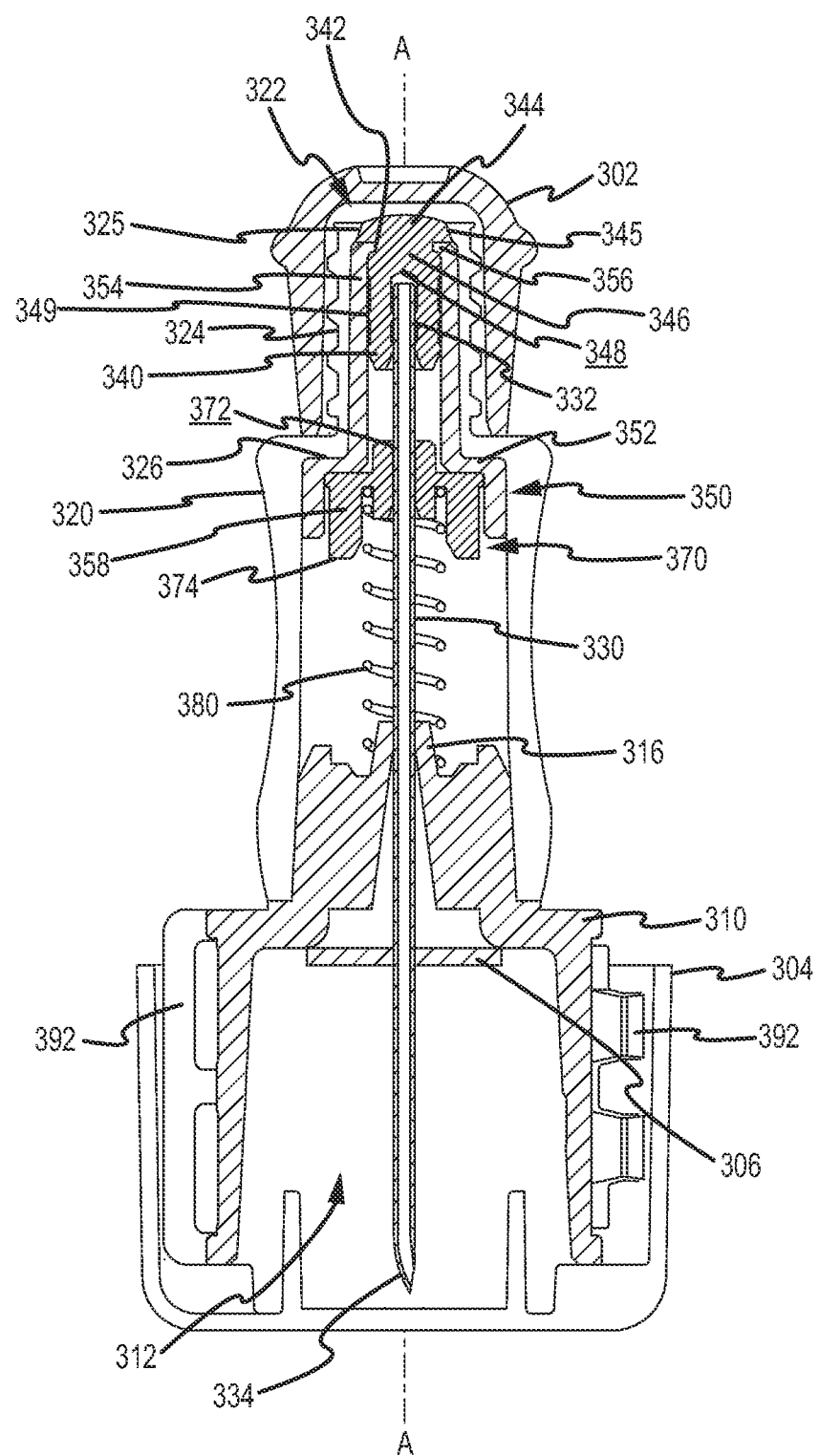
FIG. 4B is a cross sectional view of the fluid reservoir adapter embodiment of FIG. 4A taken along line AA thereof.
Figure 4C:
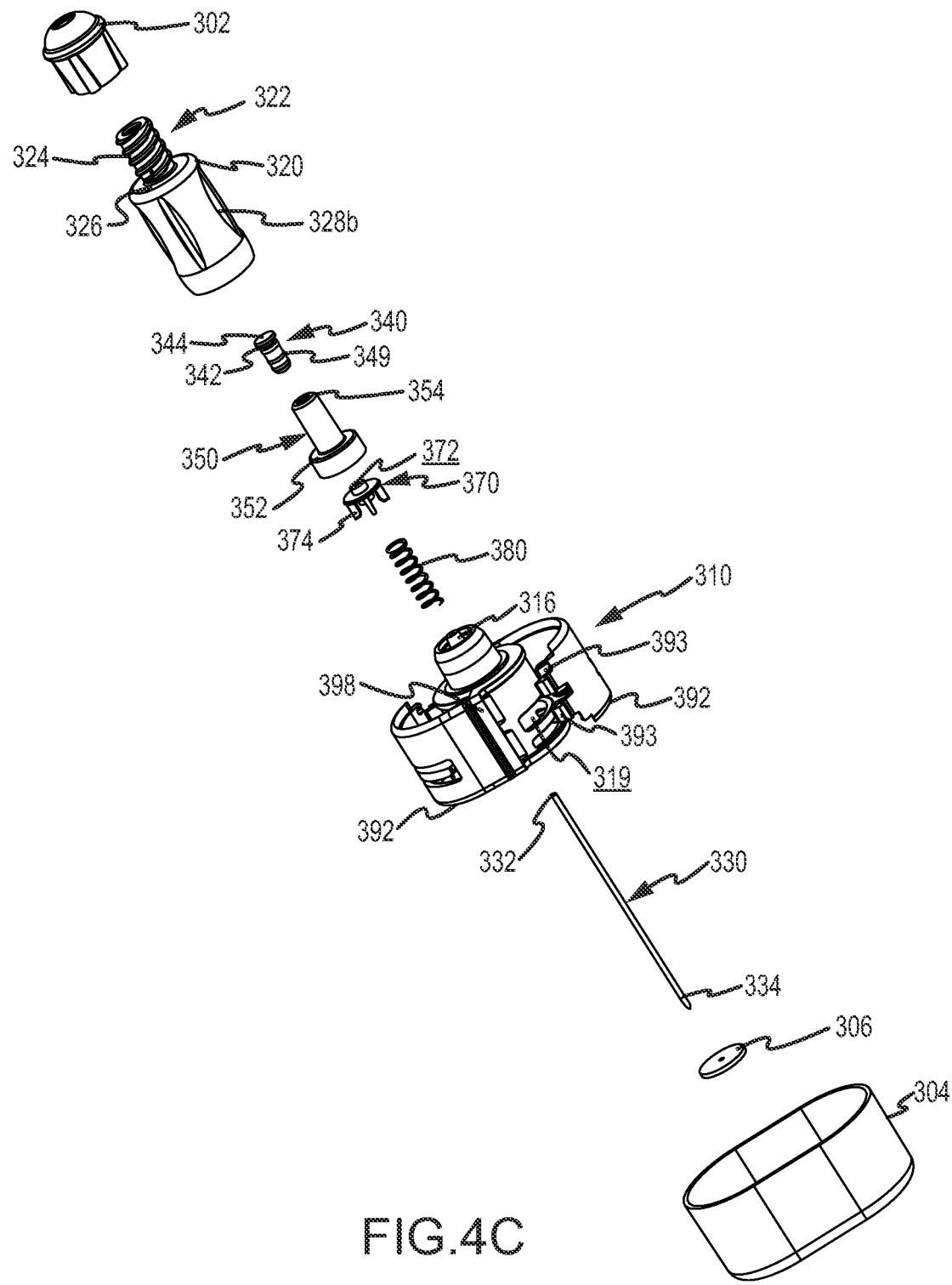
FIG. 4C is an exploded assembly view of the fluid reservoir adapter embodiment of FIGS. 4A and 4B.
Figure 4D:
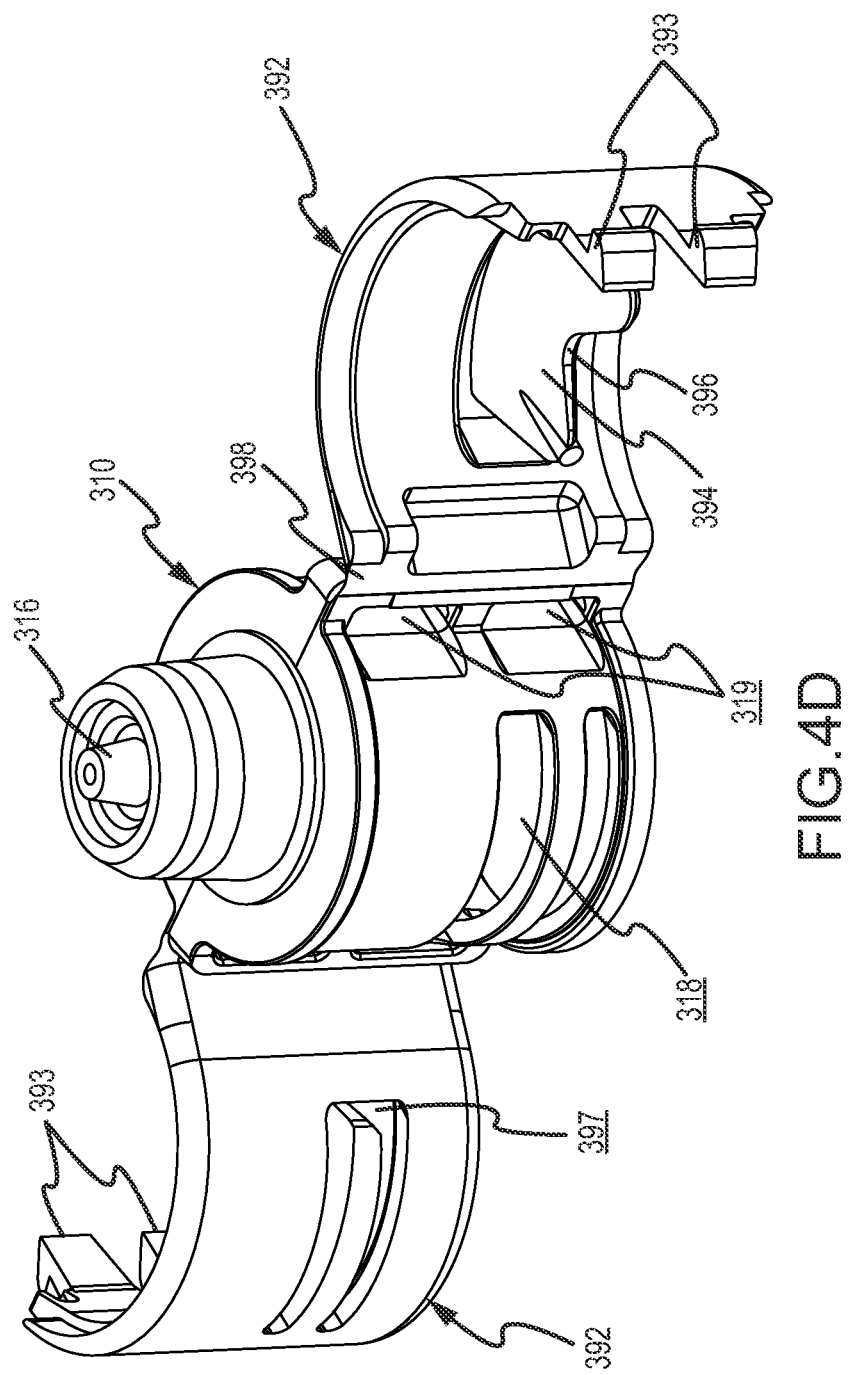
FIG. 4D is a perspective view of a first housing of the fluid reservoir adapter embodiment of FIGS. 4A-4C with interconnection members thereof shown in an open/unlocked state.

Reference is now made to FIGS. 4A-4D, which illustrate one embodiment of a fluid reservoir adapter 300. The reservoir adapter 300 may include a first housing 310 defining a first connection port 312, and a second housing 320 fixedly interconnected to the first housing 310 and defining a second connection port 322. In this embodiment, and as best shown in FIG. 4D, each of a pair of opposing interconnection members 392 may be hingedly interconnected to and closeable relative to the first housing 310 for retention of a fluid reservoir port that may be selectively positioned within the first connection port 312, as will be described further hereinbelow.

As shown, the second connection port 322 may include external threads 324. The second connection port 322 and external threads 324 thereof may be sized for selective interconnection to and disconnection from the second connection port 122 and internal threads 124 of the transfer adapter 100 discussed hereinabove.

The reservoir adapter 300 may include a tubular member 330 fixedly interconnected in an intermediate region thereof to the first housing 310, wherein one end 334 of the tubular member 330 projects into the first connection port 312. The tubular member 330 may be located to extend along a longitudinal axis AA through a portion of the second housing 320 and defines a fluid passageway from the end 332 to another end 334 thereof. By way of example, the tubular member 330 may comprise a metal cannula fixedly received within a central bore of a hub 316 of the first housing 310.

The end 334 of the tubular member 330 may be adapted for penetration through a seal membrane of a port of a fluid reservoir. For example, a bent and angularly cut end of a metal cannula may be utilized (e.g. a Huber tip cannula). Further, and as shown in FIG. 4C, the reservoir adapter may include disk-like seal member 306 for facilitating a seal interface between a cannula and a reservoir port.

A protective cup-shaped member 304 may be initially provided with the reservoir adapter 300 to cover the first connection port 312 and interconnection members 392 so as to shield the first connection port 312 and reduce the occurrence of unintended, premature closure of the interconnection members 392, wherein the protective member 304 may be removed prior to use. Further, a protective cap 302 may be initially provided to cover and thereby shield the second connection port 322, wherein the protective cap 302 may be removed prior to use.

To facilitate manipulation of the second housing 320 by a user, the outside surface of the housing 320 may be contoured for finger contact. For example, a plurality of concave, or dished, surface portions 328a may be provided, with raised rib portions 328b interposed therebetween. Such raised rib portions 328b may extend in aligned relation to the longitudinal axis AA and may be peripherally disposed at greater distance from the axis AA than the balance of the second housing 320.

In relation to the reservoir adapter 300 embodiment shown in FIGS. 4A-4D, a seal member comprising a resilient septum 340 and a carriage 350 may be provided to sealably enclose the end 332 of the tubular member 330 when the second connection port 322 is in a disconnected state. In this regard, and as best shown by FIG. 4B, the resilient septum 340 may be retainably and sealably interconnected to a tubular end 354 of the carriage 350. More particularly, the resilient septum 340 may include a peripheral, annular recess 342 for receiving an inwardly-extending annular end-flange 356 of the carriage 350, wherein a front face portion 344 of the resilient septum 340 may be disposed outside of the carriage 350 and a body portion 346 of the resilient septum may be disposed within the tubular end 354 of the carriage 350. In turn, the end 332 and an adjoining portion of the tubular member 330 may be sealably disposed within a receiving cavity 348 of the body portion 346 of the resilient septum 340.

In the later regard, the inside surface of the tubular end 354 of carriage 350 and the outside surface of the body portion 346 of the resilient septum 340 may be sized and/or otherwise contoured to facilitate a tight interface therebetween. Further, the outside surface of the end portion of the tubular member 330 that adjoins end 332, and the inside surface of the receiving cavity 348 of the body portion 346 of the resilient septum 340 may be sized and/or contoured to facilitate a tight interface therebetween. For example, the noted components may have external and internal diameters established to yield mechanical interference therebetween. Further, the outside surface of body portion 346 and inside surface of cavity 348 of resilient septum 340 may be provided with outwardly-projecting rings 349 (see FIG. 4C) and/or inwardly-projecting rings (not shown) to compressively interface with the inside surface of the tubular end 354 of carriage 350 and outside surface of tubular member 330, respectively. In turn, sealable closure of the end 332 of tubular member 330 may be realized.

As will be further addressed hereinbelow, the second end 332 of the tubular member 330 may be provided to fluidly interface with the tubular member 130 of the transfer adapter 100 described hereinabove, wherein a closed fluid passageway may be established through the reservoir adapter 300 and transfer adapter 100. In conjunction therewith, the resilient septum 340 may be pierceable or pre-pierced (e.g. pre-pierced during manufacturing utilizing a needle having a closed, pencil point, solid tip) and/or pre-cut (e.g. pre-cut via a laser during manufacturing) to facilitate the passage of the end 332 of the tubular member 330 therethrough, i.e. progressively from the cavity 348 through the body portion 346 and through the front face portion 344. Further in that regard, the resilient septum 340 and carriage 350 may be axially displaceable relative to the tubular member 330 and biased toward the second connection port 322.

More particularly, upon rotative interconnection of the second connection port 322 with the second connection port 122 of the transfer adapter 100, the front face 162 of the septum 160 of the transfer adapter 100 may engage the front face 342 of the septum 340 of the reservoir adapter 300. In this regard, and as previously noted, the recessed biased-positioning of the septum 160 of the transfer adapter 100 facilitates initial rotative interconnection of the transfer adapter 100 and reservoir adapter 300, since such initial interconnection may be achieved prior to engagement of the septum 160 with the septum 340. Upon further rotative interconnection, the front face 162 of septum 160 of the transfer adapter 100 may progressively advance in to the second port 322 so as to inwardly and forcibly displace the septum 340 and carriage 350 against a spring-loading force acting thereupon, thereby facilitating a sealed interface. In the later regard, carriage 350 may operatively interface with a guide 370 and a spiral spring 380 that biases the guide 370, carriage 350 and septum 340 toward from the second connection port 322 of the reservoir adapter 300.

As shown in FIG. 4B, the carriage 350 may include a shoulder portion 352 that may be biased towards and into a butting relation with a complimentarily shaped shoulder portion 326 of the second housing 320 when the second connection port 322 is in a disconnected state. In turn, the guide 370 may be sized to fit within an enlarged, cup-shaped end 358 of the carriage member 350 that slidably engages an internal surface of the second housing 320. A central bore 372 through the guide 370 may slidably receive the tubular member 330 therethrough. The guide 370 may further include a plurality of posts 374 for receiving and thereby locating an end of the spring 380 therebetween.

As may be appreciated, as the septum 340 and carriage 350 are inwardly displaced upon interconnection of the reservoir adapter 300 with the transfer adapter 100, the end 332 of the tubular member 330 may forcibly pass, or penetrate, from the cavity 348 though the body 346 and front face portion 344 of the septum 340 of the reservoir adapter 300, and then through the front face portion 164 and body 166 of the septum 160 of the transfer adapter 100 for receipt within the cavity 168 of the septum 160 adjacent to and in fluid communication with end 132 of the tubular member 130 of the transfer adapter 100. In such position, a medical liquid may be passed between the reservoir adapter 300 and transfer adapter 100. More particularly, a closed fluid passageway may be provided between the first connection port 112 of the transfer adapter 100 and the end 334 of the tubular member 330 of the reservoir adapter 300.

Upon disconnection of the second connection port 320 of the reservoir adapter 300 from the second connection port 120 of the transfer adapter 100, e.g. after transfer of a medical liquid between the transfer adapter 100 and reservoir adapter 300, the end 332 of tubular member 330 may progressively pass back out of the septum 160 of the transfer adapter 100 and the septum 340 of the patient connector 300. In the later regard, the septum 340 may be sufficiently resilient so as to sealably close upon passage of the end 332 of tubular member 330 therefrom. By way of example, the septum 340 may be integrally defined by a resilient material such as polyisoprene.

As may be appreciated, upon disconnection of the reservoir adapter 300 and transfer adapter 100 the end 332 of tubular member 330 passes out of septum 340 as the septum 340 and carriage 350 of the reservoir adapter 30 automatically advance relative to the tubular member 330 and responsive to the spring-loading force provided by spring member 380. In conjunction with such movement, the septum 340 may automatically, sealably enclose the end 332 of the tubular member 330. Further, the front face portion 344 of the septum 340 may automatically close the second connection port 322. Additionally, a front surface of the front face portion 344 may be disposed substantially flush with or outwardly beyond the end of the housing 320, thereby facilitating cleaning and/or disinfecting the front face portion 344.

In this regard, and in one approach, the front face portion 344 of the resilient septum 340 may comprise a tapered down, or beveled, peripheral end surface 345 sized to engage a complimentary tapered surface 325 provided at the end of the second connection port 322 of housing 320. Such engagement facilitates automatic closure of the second connection port 322 by the front face portion 344 of the septum 340 when the second connection port 322 is in a disconnected state.

Further in this regard, the front face portion 344 of the septum 340 may be provided to have a maximum cross-dimension (e.g. a maximum diameter) that is less than a minimum cross-dimension, (e.g. a minimum diameter) of an internal chamber 327 defined by the second housing 320 proximal to the tapered surface 325 thereof, wherein the septum 340 is spaced from and free from engagement with the second housing 320 when forcibly retracted during interconnection of the reservoir adapter 300 with the transfer adapter 100 described hereinabove or when forcibly retracted upon engagement with a nozzle of a conventional male luer fitting during interconnection of the reservoir adapter 300 with the male luer fitting. In the later regard, in certain implementations a nozzle of a male luer fitting of a conventional needleless syringe or infusion tubing line port may sealably engage the front surface of the front face portion 344 of the spring-loaded septum 340, in a face-to-face manner, upon interconnection of the reservoir adapter 300 and needleless syringe or infusion tubing line port, and at the same, the end 332 of the tubular member 330 may advance through the septum 340 to fluidly interface with the nozzle of the male luer fitting to facilitate liquid transfer therebetween.

Particular reference is now made to FIG. 4D which illustrates the opposing interconnection members 392 in an articulated, open position relative to the first connection port 312 prior to interconnection of the first connection port 312 to a fluid reservoir port. Each interconnection member 392 may be of an arcuate configuration and may include a laterally-oriented engagement flange 394 that may be optionally shaped to define a concave or v-shaped, lateral edge surface 396. Further, each engagement flange 394 may be supportably interconnected in a cantilevered manner along a single side edge to a side edge of a window 397 extending through the corresponding interconnection member 392, wherein each flange 394 may flex, or elastically deform, to a limited degree through the corresponding window 397. Correspondingly, the first housing 310 may include windows 318 sized and located to receive therethrough the contoured engagement flanges 394 of the interconnection members 392 upon interconnection of the reservoir adapter 300 to a fluid reservoir port.

In this regard, upon positioning of a fluid reservoir port within the first connection port 312, each of the interconnection members 392 may be pivoted about a corresponding hinge 398 so that the engagement flanges 394 extend through windows 318 and into the interconnection port 312 so as to capture a fluid reservoir port therewithin. For example, the lateral edges 396 of the engagement flanges 394 may engage and elastically flex into tight engagement with a fluid reservoir port. Additionally and/or alternatively, an outwardly extending flange, or enlarged annular lip, of a fluid reservoir port may be restricted from removal from the first connection port 312 via face-to-face engagement with, or blockage by, surfaces of the flanges 394 that extend internally across the first connection port 312 (e.g. bottom surfaces of flanges 394).

In either case, each of the interconnection members 392 may include a locking member or members for maintaining, or locking, the interconnection member 392 in a closed position relative to a fluid reservoir port. In one approach, each member 392 may include at least one snap-lock member 393 (e.g. two shown for each member 392 in FIG. 4D), and at least one receiving aperture 319 may be provided (e.g. two shown along each hinge 398 in FIG. 4D) to receive the snap-lock members 393 therethrough, wherein each interconnection member 392 may be locked in a closed position relative to a fluid reservoir port. Further in that regard, the snap-lock members 393 may be provided for one-way interconnection within apertures 319, wherein the reservoir adapter 300 is not disconnectable from a fluid reservoir port once connected thereto.

In this regard, the snap-lock members 393 may each comprise an enlarged head portion having a beveled surface and an adjoining lip, wherein each snap-lock member 393 progressively flexes (e.g. elastically deforms) as the corresponding beveled surface thereof engages an edge surface at an aperture 319, and wherein the snap-lock member 393 "snaps-back" and into a locked position when the enlarged head portion thereof has been advanced through the aperture 319.

In turn, the adjoining lip of each snap-lock member 393 may abuttingly engage an edge surface at an aperture 319, in opposing relation to a spring force resulting from the engagement of a flexed flange 394 and fluid reservoir port. Such an arrangement restricts or prevents disconnection of the reservoir adapter 300 after initial interconnection with a fluid reservoir port. Various other locking approaches may be alternatively utilized to yield such functionality Reference is now made to FIGS. 5A-5G and FIGS. 6A-6C, which illustrate two embodiments of a vial adapter 400. The vial adapter 400 may include a first housing 410 defining a first connection port 412, and a second housing 420 fixedly interconnected to first housing 410 and defining a second connection port 422. As illustrated, the second connection port 422 may include external threads 424. The second connection port 422 and external threads 424 may be sized for selective interconnection with the second connection port 120 and internal threads 122 of the transfer adapter 100 described hereinabove.

The vial adapter 400 may include a tubular member 430 that extends through and is fixedly interconnected in an intermediate region thereof to a central bore of a hub 416 that is connected to the first housing 410 via support legs 418. As best shown in FIGS. 5E and 5G, the hub 416 and support legs 428 may be integrally formed together with the first housing 420.

Figure 5A:
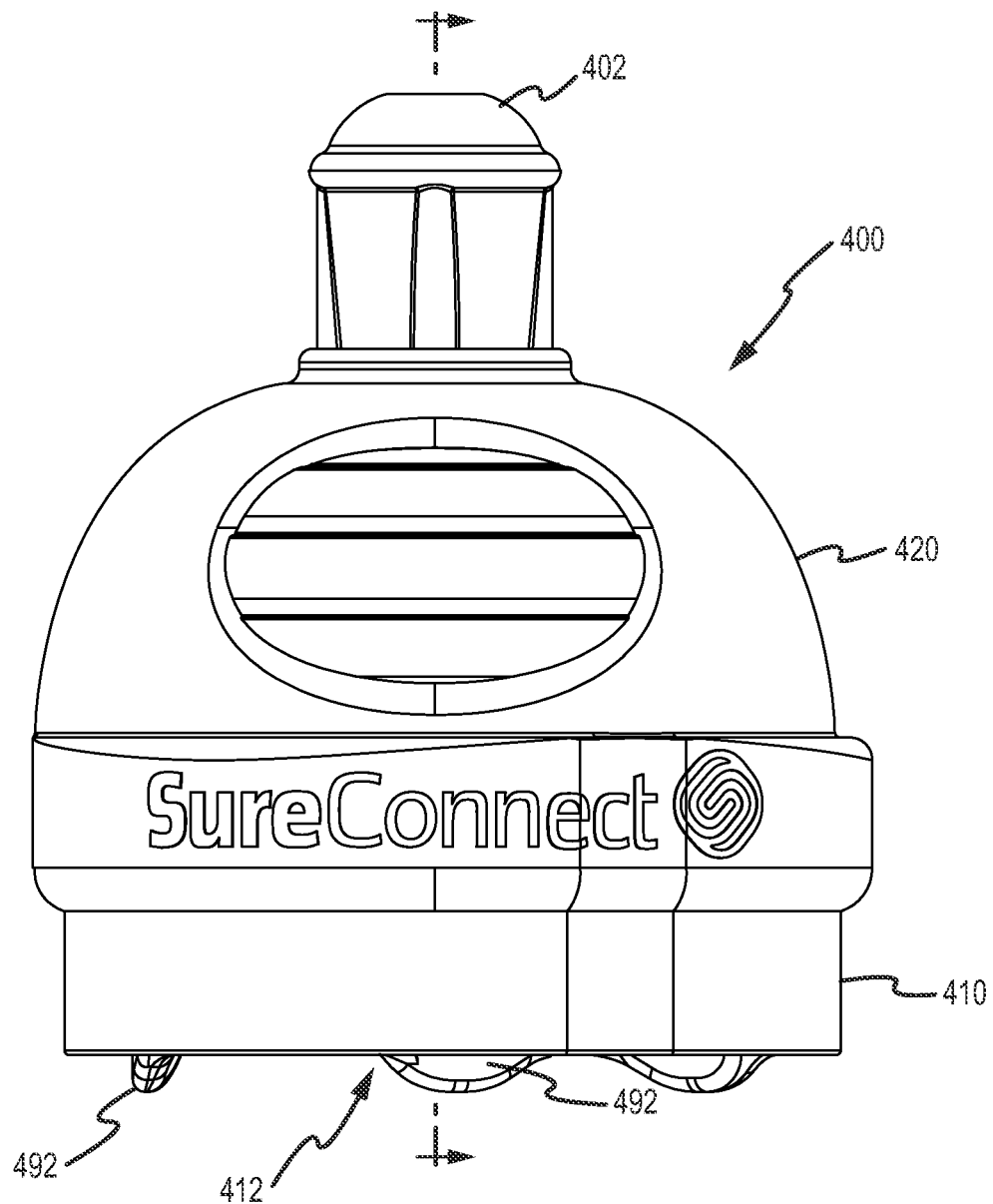
FIG. 5A is a side view of one embodiment of a vial adapter.

As illustrated in FIG. 5A, one end 434 of the tubular member 430 may project into the first connection port 412. The tubular member 430 may be located to extend along an axis AA and define a fluid passageway from the end 434 to another end 432 thereof. By way of example, the tubular member 430 may comprise a metal cannula.

The end 434 of the tubular member may be adapted for penetration through a seal member at the top of a drug-containing vial. For example, a bent and angularly cut end of a metal cannula may be utilized (e.g. a Huber tip cannula). In this regard, the vial adapter 400 may include a resilient seal cap 404 positioned over the end 434 to both shield the end 434 prior to use and to otherwise facilitate a sealed interface between the tubular member 430 and vial seal member during use, as will be further described. Further, a protective cap 402 may be initially provided to cover and thereby shield second connection port 422 and may be removed prior to use.

To facilitate manipulation of the second housing 420 by a user, the outside surface of the housing 420 may be contoured for finger contact. For example, in the embodiment of FIGS. 5A-5G a plurality of concave, or dished, surface portions 428a may be provided with raised rib portions 428b interposed therebetween. In the embodiment of FIGS. 6A-6E, a plurality of ridge, or stepped portions 428d may be provided for finger contact.

Figure 5B:
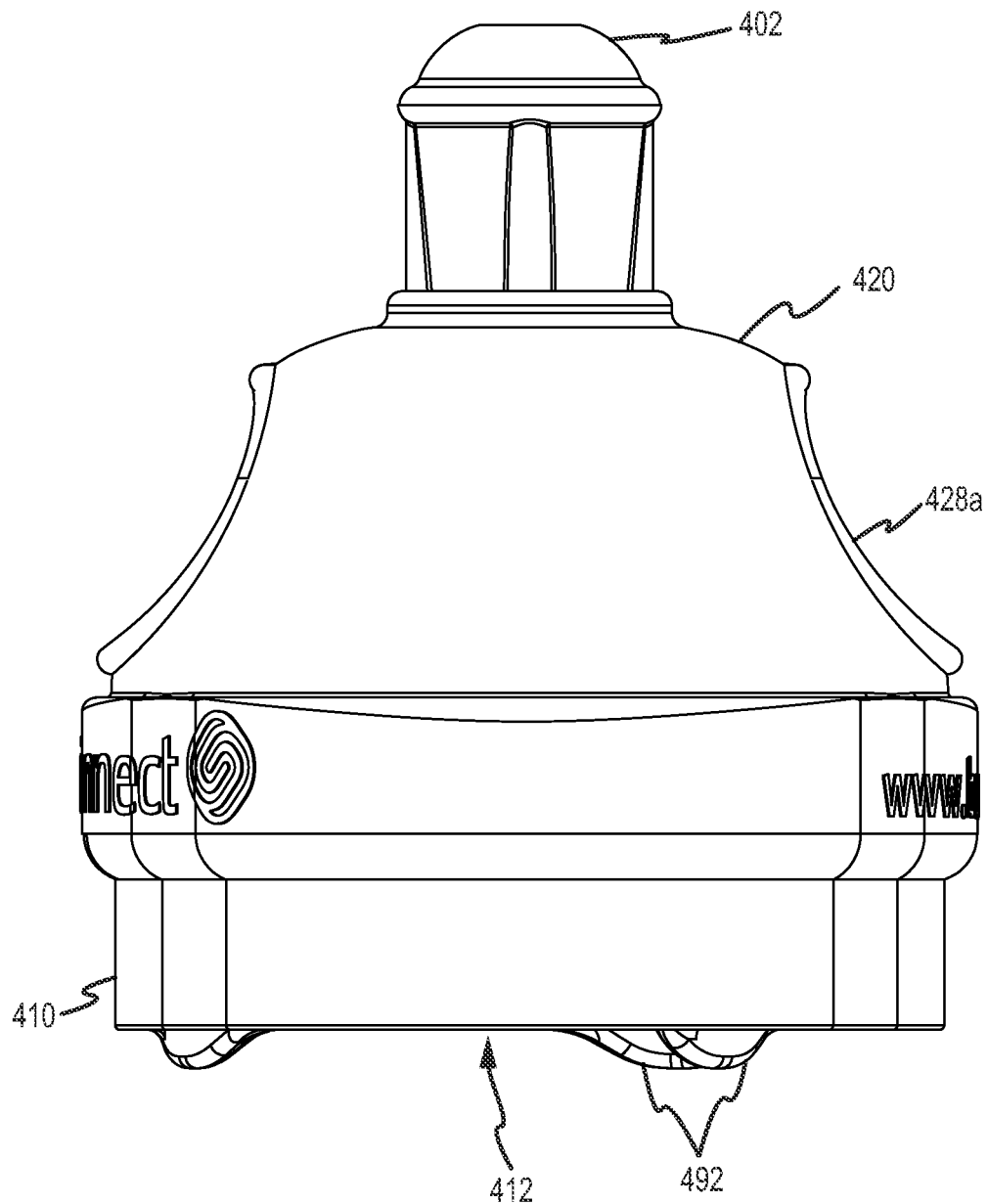
FIG. 5B is another side view of the vial adapter embodiment of FIG. 5A.
Figure 5C:
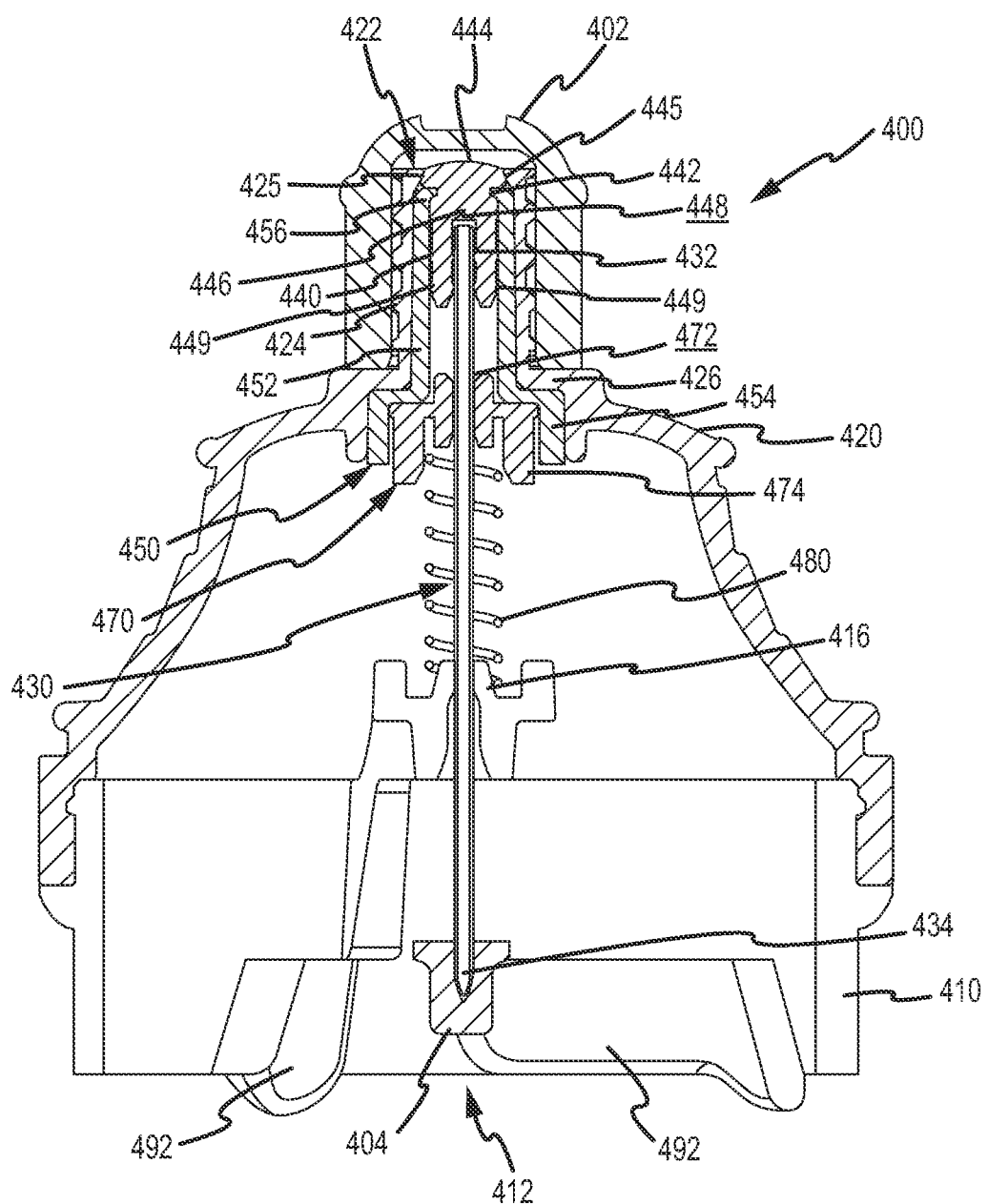
FIG. 5C is a cross sectional view of the vial adapter embodiment of FIGS. 5A and 5B taken along line AA of FIG. 5A.
Figure 5D:
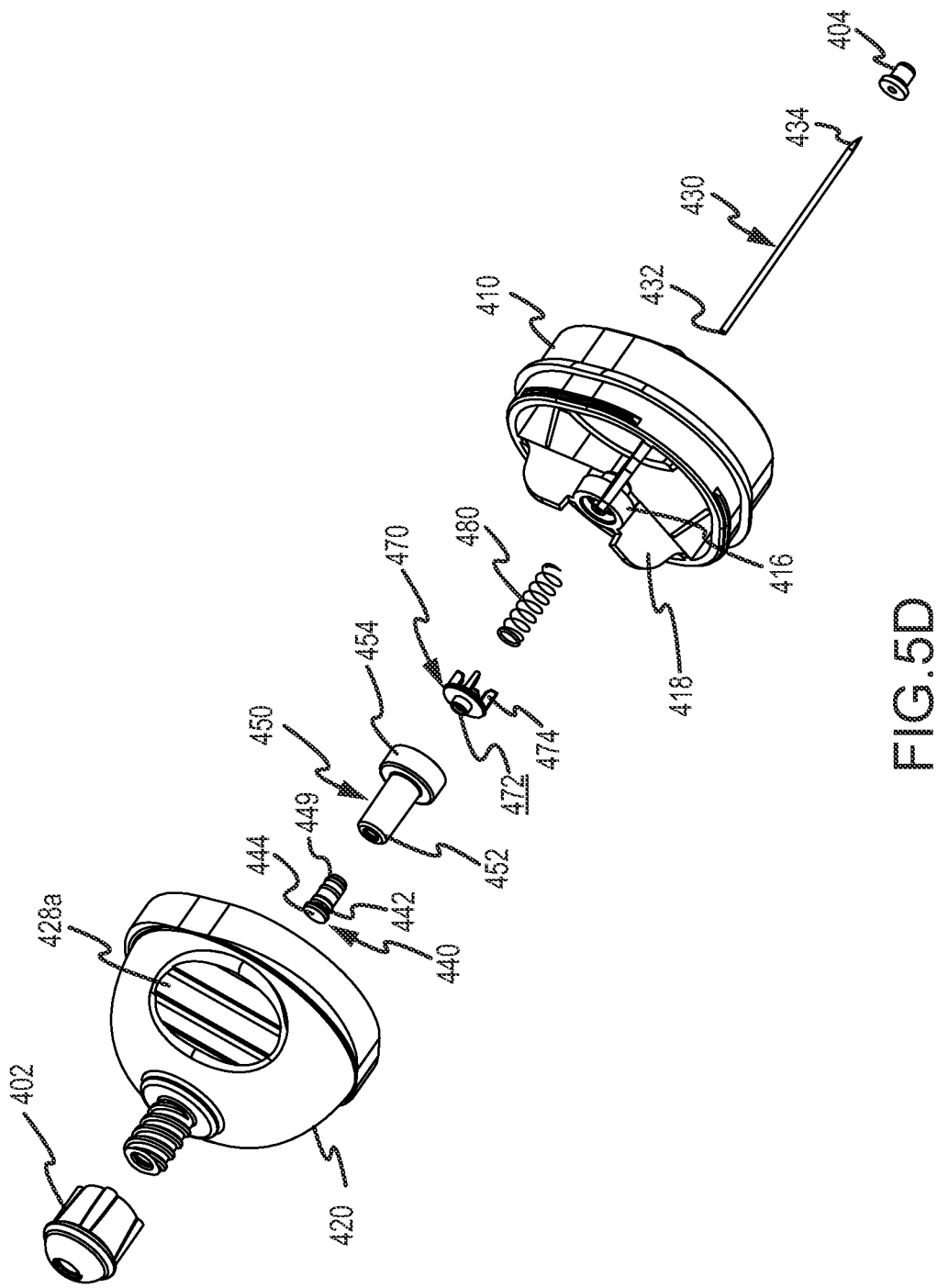
FIG. 5D is an exploded assembly view of the vial adapter embodiment of FIGS. 5A-5C.
Figure 5E:
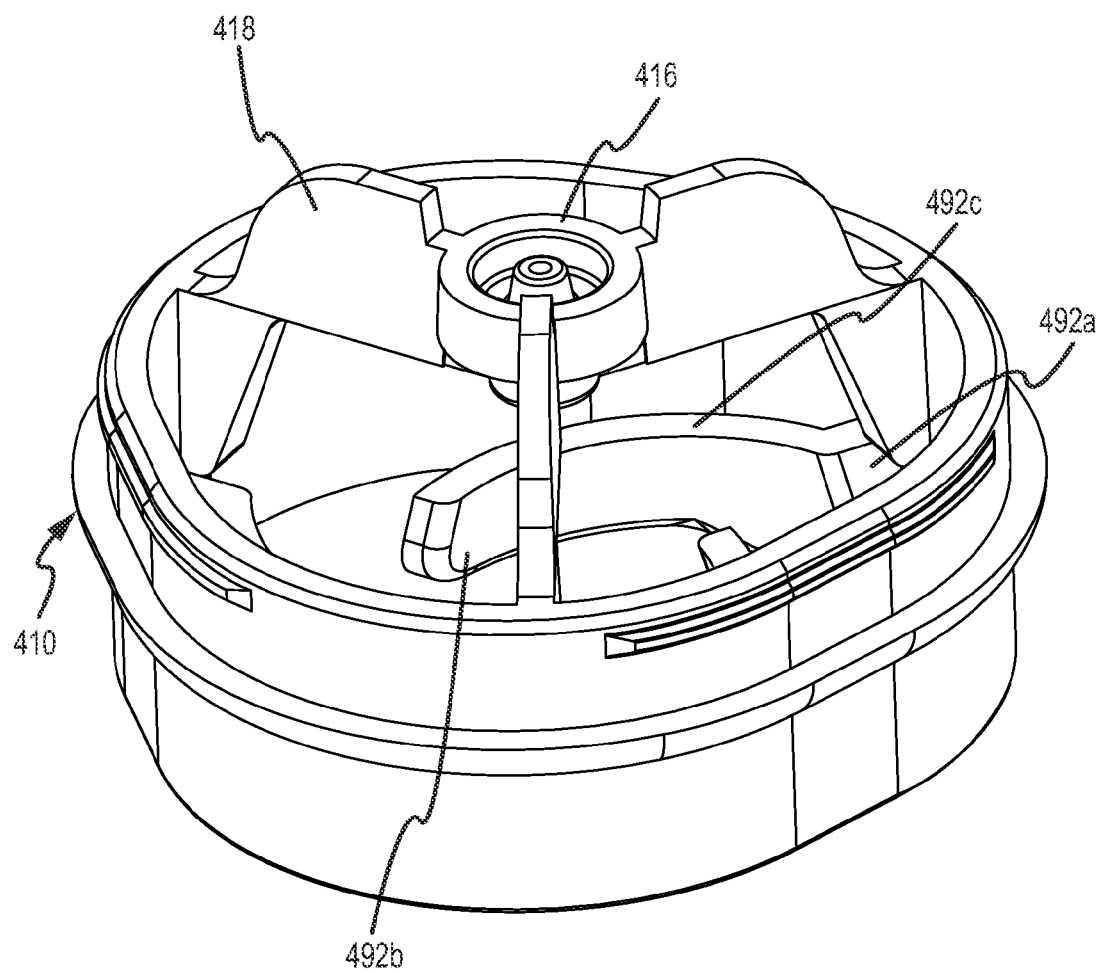
FIG. 5E is a top perspective view of a housing comprising the vial adapter embodiment of FIGS. 5A-5D.

As shown in FIG. 5B, the carriage 450 may include a shoulder portion 452 that may be biased towards and into a butting relation with a complimentarily shaped shoulder portion 426 of the second housing 420 when the second connection port 422 is in a disconnected state. In turn, the guide 470 may be sized to fit within an enlarged, cup-shaped end 454 of the carriage member 450 that slidably engages an internal surface of the second housing 420. A central bore 472 through the guide 470 may slidably receive the tubular member 430 therethrough. The guide 470 may further include a plurality of posts 474 for receiving and thereby locating an end of a spring 480 therebetween.

In relation to the vial adapter 400 embodiment shown in FIGS. 5A-5D, a seal member comprising a resilient septum 440 and a carriage 450 may be provided to sealably enclose the end 432 of the tubular member 430 when the second connection port 422 is in a disconnected state. In this regard, and as best shown by FIG. 5B, the resilient septum 440 may be retainably and sealably interconnected to a tubular end 454 of the carriage 450. More particularly, the resilient septum 440 may include a peripheral, annular recess 442 for receiving an inwardly-extending annular end-flange 456 of the carriage 450, wherein a front face portion 444 of the resilient septum 440 may be disposed outside of the carriage 450 and a body portion 446 of the resilient septum may be disposed within the tubular end 454 of the carriage 450. In turn, the end 432 and an adjoining portion of the tubular member 430 may be sealably disposed within a receiving cavity 448 of the body portion 446 of the resilient septum 440. In turn, the end 432 and an adjoining portion of the tubular member 430 may be sealably disposed within a receiving cavity 448 of the body portion 446 of the resilient septum 440.

In the later regard, the inside surface of the tubular end 454 of carriage 450 and the outside surface of the body portion 446 of the resilient septum 440 may be sized and/or otherwise contoured to facilitate a tight interface therebetween. Further, the outside surface of the end portion of the tubular member 430 that adjoins end 432, and the inside surface of the receiving cavity 448 of the body portion 446 of the resilient septum 440 may be sized and/or contoured to facilitate a tight interface therebetween. For example, the two components may have external and internal diameters established to yield mechanical interference therebetween. Further, the outside surface of body portion 446 and inside surface of cavity 448 of resilient septum 440 may be provided with outwardly-projecting rings 449 (see FIG. 5C) and inwardly-projecting rings (not shown), respectively, to compressively interface with the inside surface of the tubular end 454 of carriage 450 and outside surface of tubular member 430, respectively. In turn, sealable closure of the end 432 of tubular member 430 may be realized.

As will be further addressed hereinbelow, the second end 432 of the tubular member 430 may be provided to fluidly interface with the tubular member 130 of the transfer adapter 100 described hereinabove, wherein a closed fluid passageway may be established through the vial adapter 400 and the transfer adapter 100. In conjunction therewith, the resilient septum 440 may be pierceable or pre-pierced (e.g. pre-pierced during manufacturing utilizing a needle having a closed, pencil point, solid tip) and/or pre-cut (e.g. pre-cut via a laser during manufacturing) to facilitate the passage of the end 432 of the tubular member 430 therethrough, i.e. progressively from the cavity 448 through the body portion 446 and the front face portion 444. Further in that regard, the resilient septum 440 and carriage 450 may be axially displaceable relation to the tubular member and biased toward the second connection port 422.

More particularly, upon rotative interconnection of the second connection port 422 with the second connection port 122 of the transfer adapter 100, the front face 162 of the septum 160 of the transfer adapter 100 may advance to engage the front face 442 of the septum 440 of the vial adapter 400. In this regard, and as previously noted, the recessed biased-positioning of the septum 160 of the transfer adapter 100 facilitates initial rotative interconnection of the transfer adapter and vial adapter 400, since such initial interconnection may be achieved prior to engagement of the septum 160 with the septum 440. Upon further rotative interconnection, the front face 162 of septum 160 of the transfer adapter 100 may progressively advance in to the second port 422 so as to inwardly and forcibly displace the septum 440 and carriage 450 against a spring-loading force acting thereupon. In the later regard, carriage 450 may operatively interface with a guide 470, and the spring member 480 that biases the guide 470, carriage 450 and septum 440 toward from the second connection port 422 of the vial adapter 400.

As shown in FIG. 5B, the carriage 450 may include a shoulder portion 452 that may be biased towards and into abutting relation with a complimentarily shaped shoulder portion 426 of the second housing 420 when the second connection port 422 is in a disconnected state. In turn, the guide 470 may be sized to fit within an enlarged, cup-shaped end 454 of the carriage member 450 that slidably engages an internal surface of the second housing 420. A central bore 472 through the guide 470 may slidably receive the tubular member 430 therethrough. The guide 470 may further include a plurality of posts 474 for receiving and thereby locating an end of the spring 480 therebetween.

As may be appreciated, as the septum 440 and carriage 450 are inwardly displaced upon interconnection of the vial adapter 400 with the transfer adapter 100, the end 432 of the tubular member 430 may forcibly pass, or penetrate, from the cavity 448 though the body 446 and front face portion 444 of the septum 440 of the vial adapter 400, and then through the front face portion 164 and body 166 of the septum 160 of the transfer adapter 100 for receipt within the end 132 of the tubular member 130 of the transfer adapter 130. More particularly, a closed fluid passageway may be provided between the first connector port 112 of the transfer adapter 100 and the end of the tubular member 430 of the vial adapter 400.

Upon disconnection of the second connection port 420 of the vial adapter 400 from the second connection port 120 of the transfer adapter 100, e.g. after transfer of a medical liquid between the transfer adapter 100 and vial adapter 400, the end 432 of tubular member 430 may progressively pass back out of the septum 160 of the transfer adapter 100 and the septum 440 of the vial adapter 400. As may be appreciated, upon disconnection of the vial adapter 400 and the transfer adapter 100, the end 432 of tubular member 430 passes out of septum 440 as the septum 440 and carriage 450 of the transfer adapter automatically advance relative to the tubular member 430 and responsive to the spring-loading force provided by spring member 480. In conjunction with such movement, the septum 440 may automatically, sealably enclose the end 432 of the tubular member 430. Further, the front face portion 444 of the septum 440 may automatically close the second connection port 422. Additionally, a front surface of the front face portion 442 may be disposed substantially flush with or outwardly beyond the end of the housing 420, thereby facilitating cleaning and/or disinfecting the front face portion 444.

In this regard, and in one approach, the front face portion 444 of the resilient septum 440 may comprise a tapered down, or beveled, peripheral end surface 445 sized to engage a complimentary tapered surface 425 provided at the end of the second connection port 422 of housing 420. Such engagement facilitates automatic closure of the second connection port 422 by the front face portion 444 of the septum 440 when the second connection port 422 is in a disconnected state.

Further in this regard, the front face portion 444 of the septum 440 may be provided to have a maximum cross-dimension (e.g. a maximum diameter) that is less than a minimum cross-dimension, (e.g. a minimum diameter) of an internal chamber 427 defined by the second housing 420 proximal to the tapered surface 425 thereof, wherein the septum 440 is spaced from and free from engagement with the second housing 420 when forcibly retracted during interconnection of the vial adapter 400 with the transfer adapter 100 described hereinabove or when forcibly retracted upon engagement with a nozzle of a conventional male luer fitting during interconnection of the vial adapter 400 with the male luer fitting. In the later regard, in certain implementations a nozzle in of a male luer fitting of a conventional needleless syringe or infusion tubing line port may sealably engage the front surface of the front face portion 444 of the spring-loaded septum 440, in a face-to-face manner, upon interconnection of the vial adapter 400 and needleless syringe or infusion tubing line port, and at the same, the end 432 of the tubular member 430 may advance through the septum 440 to fluidly interface with the nozzle of the male luer fitting to facilitate liquid transfer therebetween.

Figure 5F:
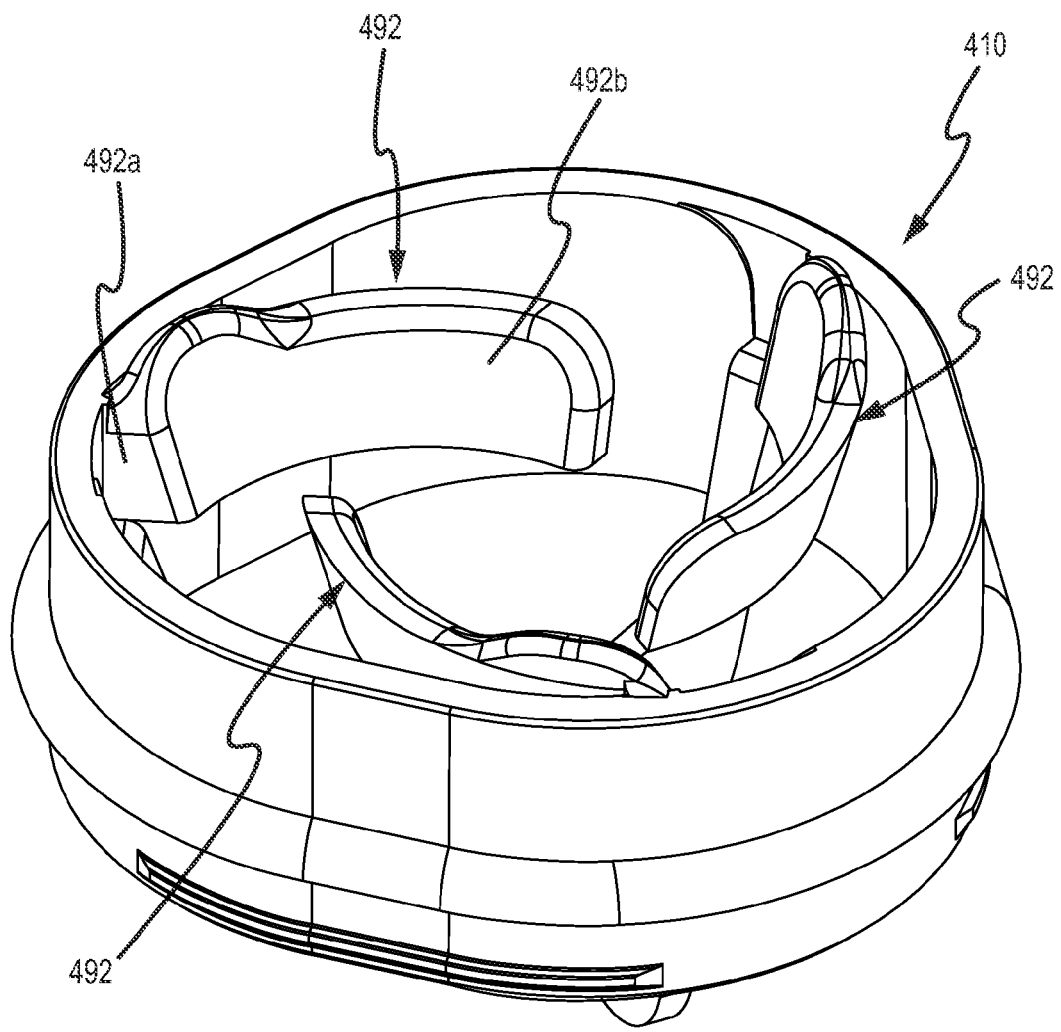
FIG. 5F is a bottom perspective view of the housing shown in FIG. 5E.
Figure 5G:
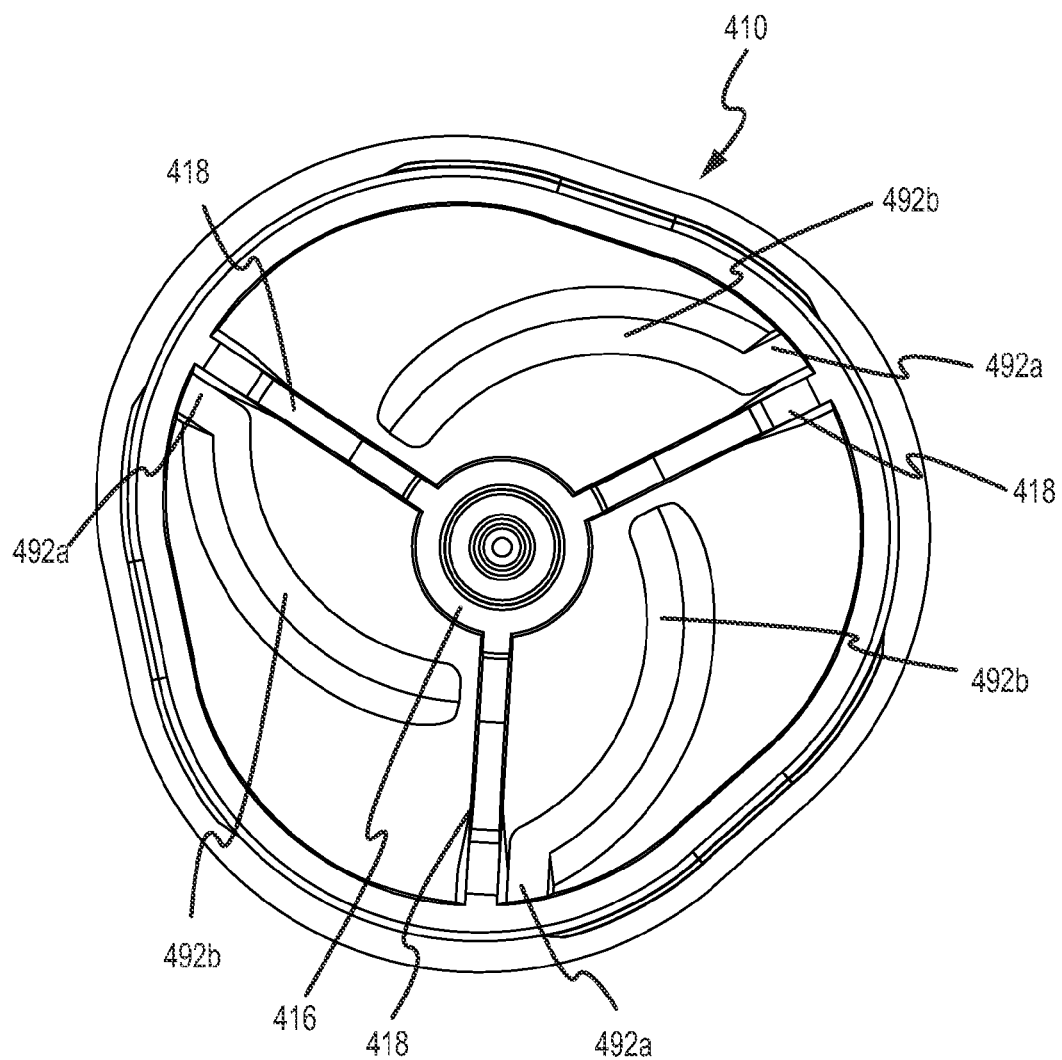
FIG. 5G is a top view of the housing shown in FIGS. 5E and 5F.

As best shown by FIGS. 5E-5G, the vial adapter 400 may include a plurality of interconnection members 492 for retainably engaging an enlarged, or lipped top end of a vial positioned within the first connection port 410. In the illustrated embodiment, three cantilevered interconnection members 492 may be employed, each of such members extending inward toward the axis AA. By way of example, and as shown in the illustrated embodiment, supported ends 492a of the interconnection members 492 may be interconnected to the second housing 420. In turn, a free end portion 492b of each of the cantilevered interconnection members 492 may be elastically deformable to deflect outward and then back inward relative to the axis AA upon receipt of the top end of a vial within the first connection port 412 (e.g. engagement with and advancement relative to a protruding annular lip of a top end port of a vial), wherein a snap-fit arrangement is provided.

Further in this regard, the free end portion 492b of each of the interconnection members 492 may be of a configuration that extends inward towards and laterally about the axis AA. More particularly, in the illustrated embodiments, each of the interconnection members 492 may be of an arcuate configuration and oriented to spiral outward relative to the axis AA from the respective free end portions 492b to the supported ends 492a thereof. Additionally, each of the free end portions 492b may comprise an angled, or beveled, side surface that faces and extends inward toward axis AA at an acute angle relative thereto, wherein such surfaces combinatively define an inverted, frusto-conical receiving aperture that functions to center the vial adapter 400 and tubular member 430 thereof in relation to and upon engagement with an enlarged, or lipped, top end of a vial.

By virtue of the above-noted features, a top end surface 492c may be defined on each of the three end portions 492b of interconnection members 492 to engage an enlarged, or lipped, top end of a vial in a secure manner. More particularly, the top end surfaces 492c may be disposed to apply a spring force (e.g. resulting from the elastic deformation of the interconnection members 492) that is directed substantially normal to an engaged surface of a protruding, annular lip at a top end port of a vial.

The vial adapter 400 embodiments described above may be optionally sized for use with a fluid reservoir. That is, a vial adapter 400 may be provided for selective fluid interconnection with a port of a fluid reservoir having a protruding, annular lip that projects laterally away from a longitudinal axis of the port. In such an application, the vial adapter 400 may be linearly advanced relative to a fluid reservoir port to cause cantilevered members 492 to flex outward as they engage and advance by the protruding lip of the reservoir port, then snap-back into locked engagement relative thereto.

Exemplary, method embodiments employing components of the system embodiments described hereinabove will now be presented. In particular, reference is first made to FIGS. 7A-7E which illustrate a method embodiment for administering a liquid drug utilizing the transfer adapter 100 and patient connector 200 described hereinabove.

Initially, the transfer adapter 100 and patient connector 200 may be removed from packaging in which such components have been maintained in a clean and sterile condition. By way of example, the components may be sterilized and packaged in a sterile environment. Alternatively, such components may be packaged and then sterilized, e.g. utilizing gamma radiation sterilization or utilizing gas sterilization, sterilization utilizing an ethylene oxide gas.

To prepare for liquid drug into administration, the patient connector 200 may be interconnected to an intravascular access port as shown in FIG. 7A. In particular, the patient connector 200 may be located with the first connection port 212 in aligned relation with a female luer fitting 90 of an intravascular access port 92. In turn, the patient connector 200 may be rotatably advanced (e.g. via clockwise twisting of first housing 210) to interconnect the first connection port 212 to the female luer connector 90.

Further, the transfer adapter 100 may be interconnected to a male luer fitting 50 of one of either a needleless syringe 52 (e.g. containing a liquid medication) as shown in FIG. 7B or at a port of an infusion tubing line set 54 fluidly interconnected to a liquid drug source as shown in FIG. 7C. For example, infusion tubing line set 54 may include a drip chamber and may be interconnected (e.g. via an end spike) to a fluid reservoir containing a liquid drug for administration to a patient.

As shown in the approach of FIG. 7B, the first connection port 112 of the transfer adapter 100 may be positioned in aligned relation with the male luer fitting 50 of the needleless syringe 52. Then, the first connection port 110 may be rotatably advanced (e.g. via clockwise twisting of second housing 120) relative to the male luer fitting 50 of the needleless syringe 52 to realize secure interconnection therebetween. Alternatively, and as shown in FIG. 7C, the first connection port 112 of the transfer adapter 100 may be positioned in aligned relation with the male luer fitting 50 of the port of an infusion tubing line set 54. Then, the first connection port 110 may be rotatably advanced (e.g. via clockwise twisting of second housing 120) relative to the male luer fitting 50 of the port of the tubing set 54 to realize secure interconnection therebetween. As may be appreciated, by virtue of the ratchet-like interconnection between the first housing 110 and second housing 120 of the transfer adapter 100, the second housing 120 is non-manipulable to disconnect the transfer adapter 100 from the needleless syringe 52 or port of the infusion tubing line set 54 after the above-noted initial interconnection therewith.

Further, each of the transfer adapter 100 and patient connector 200 may be cleaned and/or otherwise disinfected by retaining a given one of the components in one hand and utilizing the other hand to swab the septum thereof with an appropriate disinfectant (e.g. comprising 70% isopropyl alcohol). As may be appreciated, the septums of the transfer adapter 100 and patient connector 200 (e.g. at least the front face portions of the septums) may swabbed immediately prior to each interconnection of such devices with any other devices. Prior to drug administration, the patient connector 200 may also be primed and otherwise utilized to confirm patency of a vascular catheter interconnected to the access port 92 and previously inserted into a patient's vascular system. In the later regard, and by way of example, a conventional needleless syringe may be interconnected via a standard male luer fitting thereof to the second connection port 220 of the patient connector 200. Then, a plunger of the syringe may be slightly retracted to allow visual confirmation of bodily fluid withdrawal into the vascular catheter. The syringe may also contain a medical liquid for priming purposes.

To administer a liquid drug to a patient utilizing the needless syringe 52, the transfer adapter 100 may be interconnected to the patient connector 100, as shown in FIG. 7D. More particularly, the second connection port 122 of the transfer adapter 100 may be positioned in aligned relation with the second connection port 222 of the patient connector 200. Then, the second connection port 122 of the transfer adapter 100 may be rotatably advanced (e.g. via clockwise twisting of the second housing 120) to achieve interconnection of the second connection port 122 of the transfer adapter 100 with the second connection port 222 of the patient connector 200. After the noted connection has been made, the needleless syringe 52 may be manipulated so as to pass a liquid drug contained within the barrel of the needleless syringe 52 through an intravascular catheter to a patient (e.g. via advancement of the plunger of the needless syringe 52 into the barrel thereof).

Similarly, to pass a liquid drug from a fluid reservoir, e.g. reservoir 70 shown in FIG. 1, an infusion tubing line set 54 may be fluidly interconnected to the fluid reservoir 70, e.g. via interface between a spike end of the infusion tubing line set 54 and a complimentary port 78 of the fluid reservoir 70. Further, a transfer adapter 100 may be interconnected to a male luer fitting 50 at the port of the infusion tubing set 54. More particularly, the first connection port 112 and the transfer adapter 100 may be positioned in aligned arrangement with the male luer fitting 50 then rotatably advanced relative thereto (e.g. via clockwise rotation of the second housing 120) to achieve interconnection therewith. After the noted connection has been made, a liquid drug contained within the fluid reservoir 70 may be passed through the tubing set 54, e.g. via passage through a drip chamber fluidly interconnected therebetween.

After administration of a liquid drug from a syringe 52 or reservoir 70, the corresponding transfer adapter 100 may be disconnected from the patient connector 200 by rotating the second housing 120 of the transfer adapter 100 (e.g. via counter-clockwise twisting of second housing 120) while holding the patient connector 200. Then the patient connector 200 may be flushed utilizing a conventional syringe. By way of example, a conventional needleless syringe may be filled with a flush solution and rotatively interconnected via a standard male luer fitting thereof to the second connection port 220 of the patient connector 200. Optionally, and prior to such interconnection, the septum 240 of the patient connector 200 may again be disinfected via swabbing. After interconnection, the plunger of the needleless syringe may be advanced to pass a portion of the contained flush saline through the patient connector 200 and interconnected vascular catheter. Then, the needleless syringe may be rotatively disconnected from the patient connector 200. Various flush solutions may be employed, including without limitation, a saline solution, a heparin solution, an ethanol flush solution, and anti-microbial solution and/or anti-blocking solution. Following disconnection, the patient connector 200 may be later reconnected with the transfer adapter 100 for further drug administration.

In relation to the interconnection of the transfer adapter 100 and patient connector 200 described above in relation to FIGS. 7D and 7E, reference will now be made to FIGS. 8A-8C which illustrate the positioning and interface of components of the transfer adapter 100 and patient connector 200 as interconnections are made therebetween.

Figure 8A:
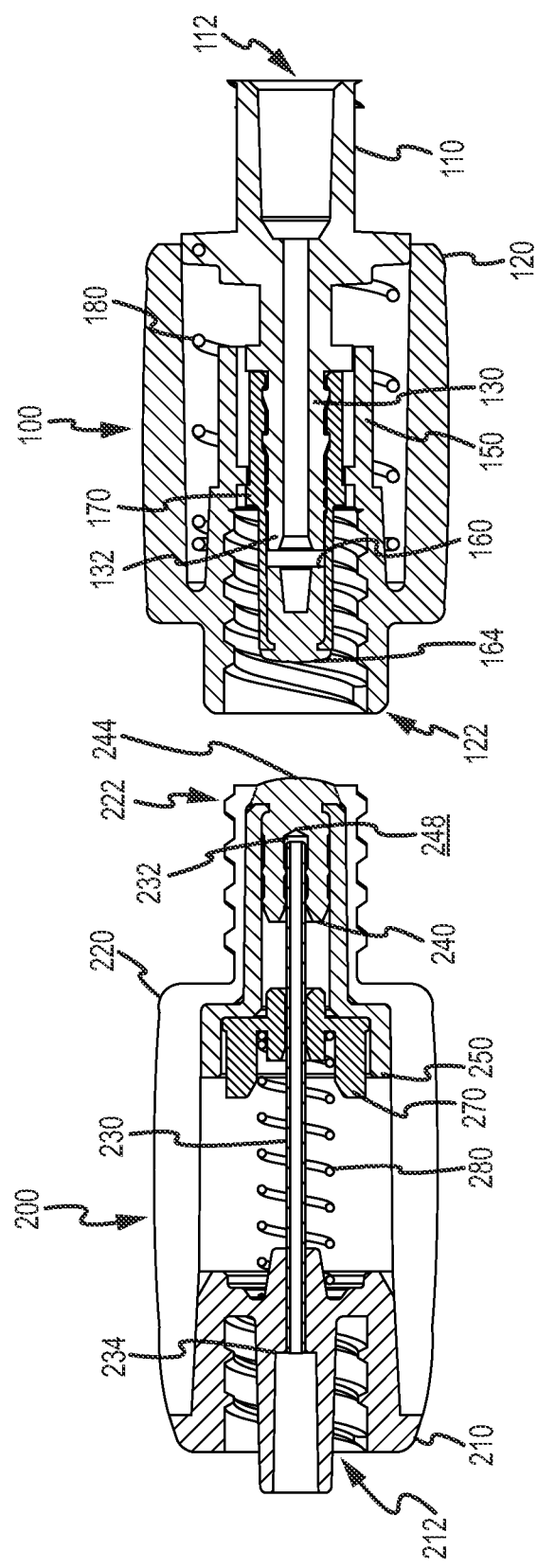
FIGS. 8A, 8B and 8C are cross sectional views of a transfer adapter embodiment and a patient connector embodiment in progressive stages of interconnection.

As shown in FIG. 8A, the second connection port 122 of the transfer adapter 100 may be initially positioned in aligned relation to the second connection port 222 of the patient connector 200. While not shown in FIG. 8A-8C, the first connection port 110 of the transfer adapter may have already been interconnected to a male luer fitting (e.g. a male luer fitting 50 of a needleless syringe 52 or port of an infusion tubing set 54) via rotation of the second housing 120 of the transfer adapter 100 in a first direction (e.g. in a clockwise direction) relative to a male luer fitting 50.

Figure 8B:
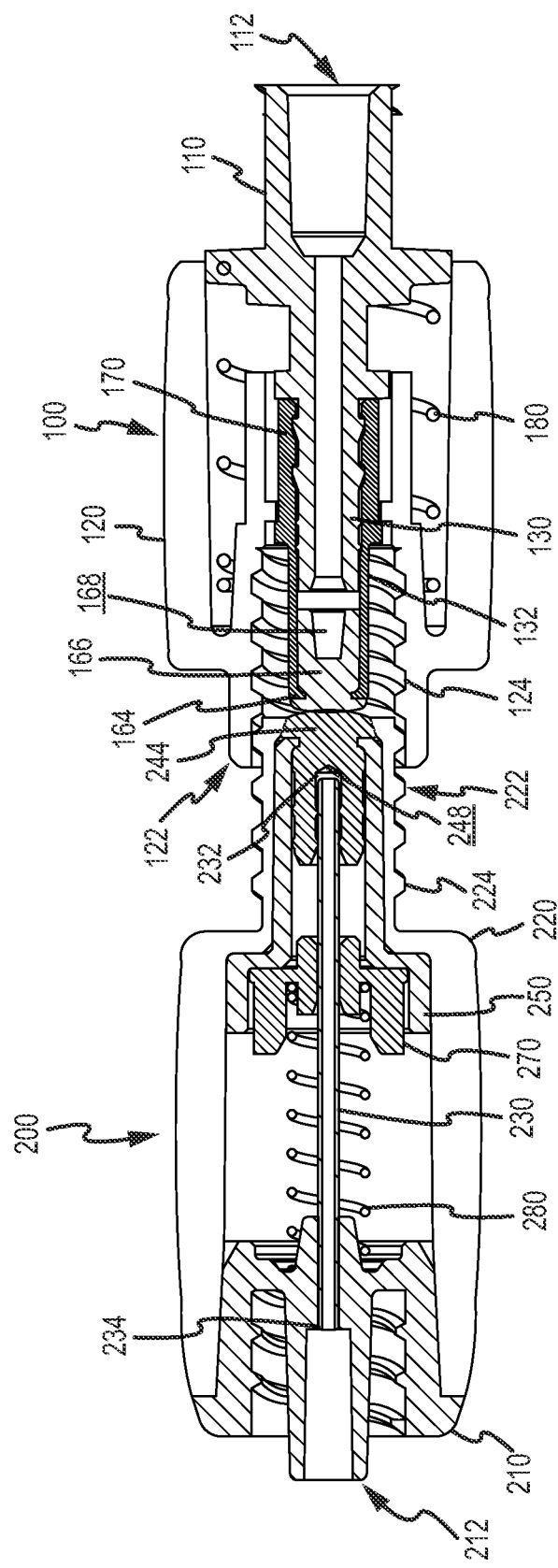

Then, as shown in FIG. 8B the second housing 120 of the transfer adapter 100 may be rotated in a second direction opposite to the first direction, e.g. in a clockwise direction, relative to the second housing 220 of the patient connector 200, wherein the internal threads 124 at second connection port 122 rotatably engage the external threads 224 at the second connection port 222 of the patient connector 200 to achieve an initial interconnection. As may be appreciated, such initial rotative interconnection of the transfer adapter 100 and patient connector 200 may be achieved prior to initial engagement between the front face portion 164 of the septum 160 of the transfer adapter 100 and the front face portion 244 of the septum 240 of the patient connector 200. Further, due to the ratchet-like arrangement between first housing 110 and second housing 120 of the transfer adapter 100, such rotative interconnection may be realized free from imparting rotative movement to the first connection port 112.

Figure 8C:
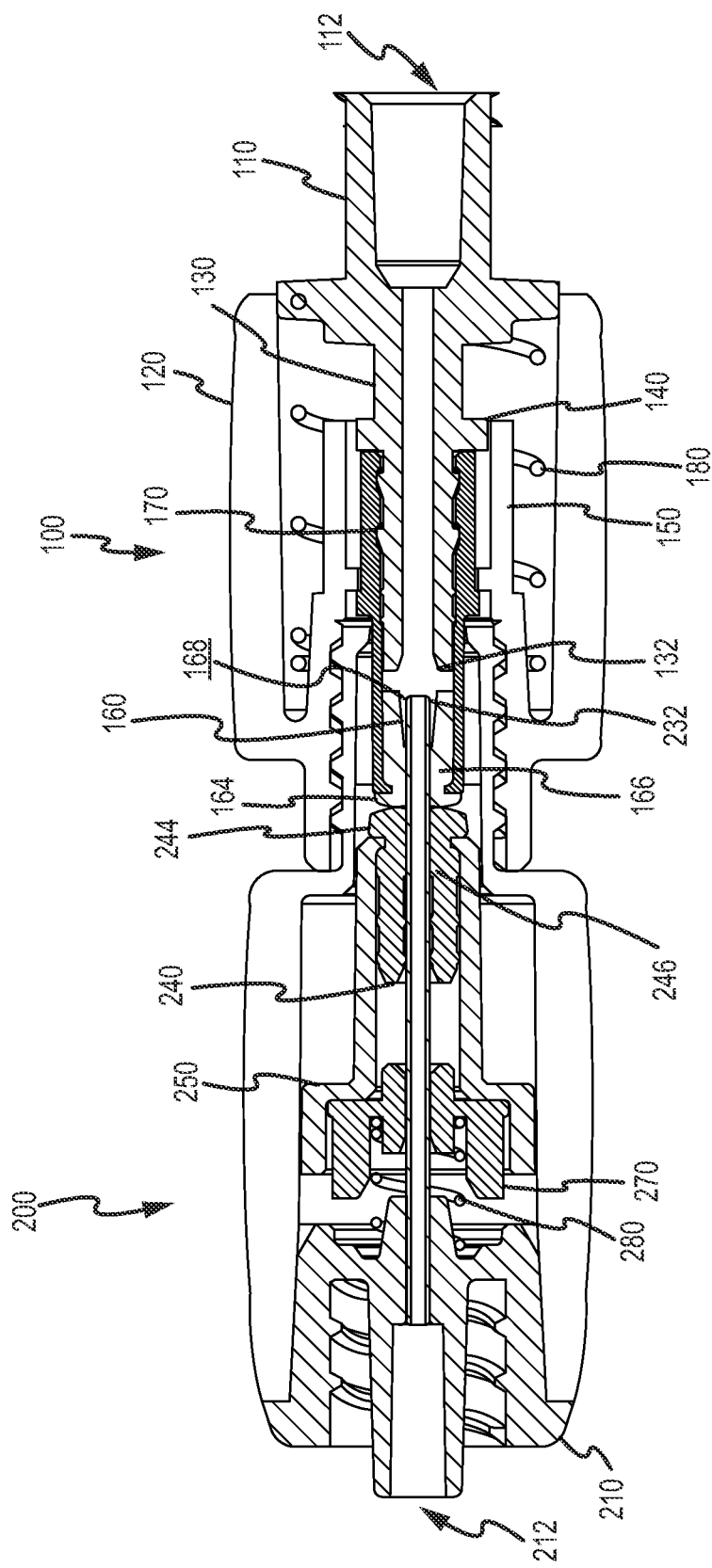

After the noted initial connection, and as shown in FIG. 8C, the second connection port 122 of the transfer adapter 100 may be further rotatively advanced in the second direction relative to the second connection port 222 of the patient connector 220 to realize a further degree of interconnection. In conjunction with such further interconnection of the transfer adapter 100 and patient connector 200, the end 232 of the tubular member 230 of the patient connector 200 may forcibly advance through the body portion 246 and front face portion 244 of the septum 240. Additionally, the end 232 of the tubular member 230 may forcibly penetrate the front face portion 164 and body portion 166 of the septum 160 of transfer adapter 100, whereupon the end 232 of the tubular member 230 may be disposed in the cavity 168 of septum 160 in juxtaposed position to the end 132 of the tubular member 130 of the transfer adapter 100. In such position, a closed fluid passageway is defined by tubular members 130, 230, septum 160 and sleeve 170. In turn, liquid transfer between the tubular members 130 and 230 may be completed. In conjunction with the described interconnection procedure, the front face portion 244 of septum 240 may engage the front face portion 164 of septum 160 and apply a spring-loading force thereagainst as the carriage 250 is forcibly retracted against and progressively compresses the spring 280 during the interconnection process.

Figures 9A, 9B:
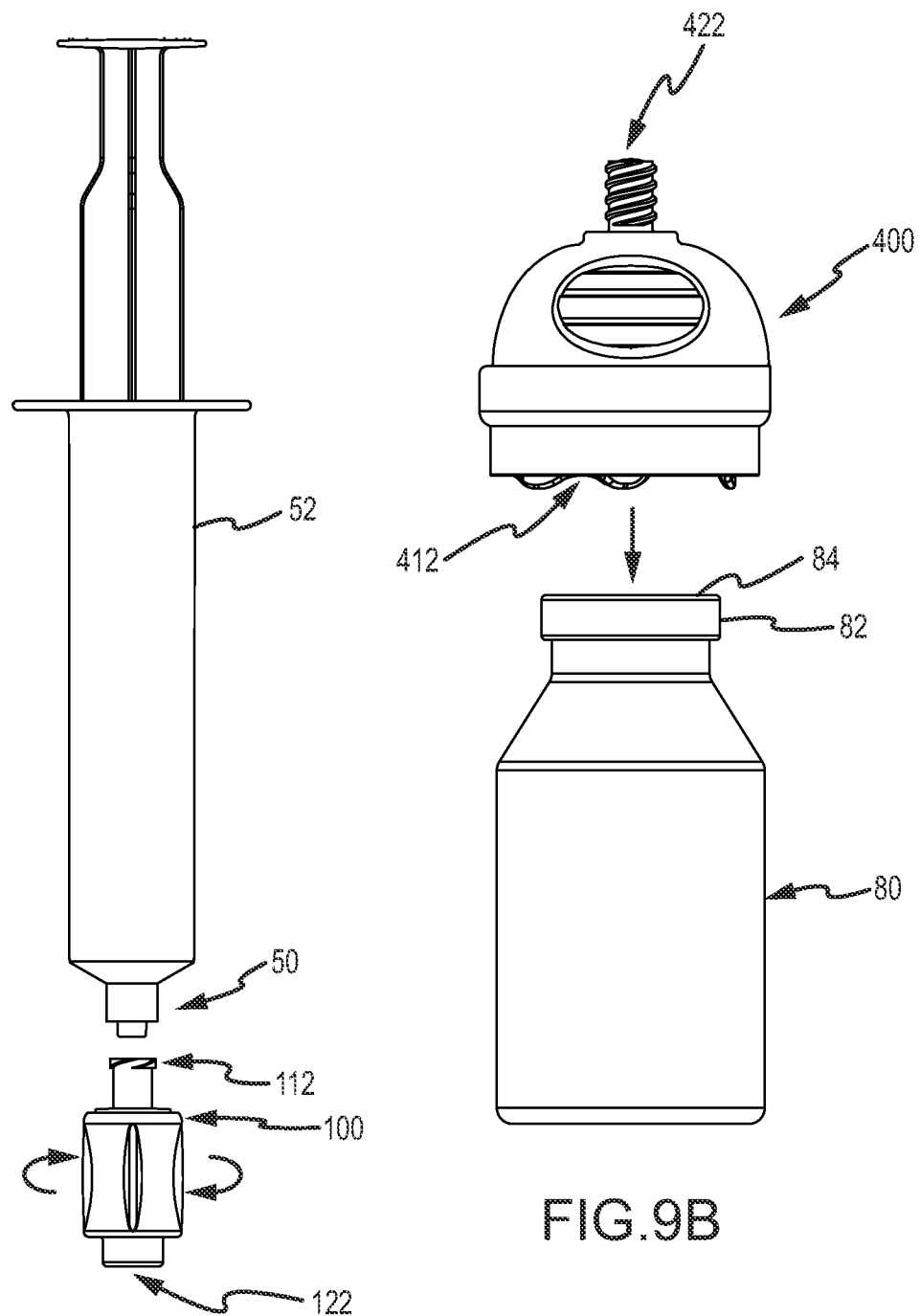
FIGS. 9A, 9B, 9C and 9D illustrate a transfer adapter embodiment and a vial adapter embodiment as employed in steps of a method embodiment for transferring a liquid drug between a needleless syringe and a vial.

Reference is now made to FIGS. 9A-9D which illustrate a method embodiment for passing a drug into a needless syringe 54 utilizing the transfer adapter 100 and the vial adapter 400 described hereinabove. Initially, the transfer adapter 100 and vial adapter 400 may be removed from separate or common packaging in which such components have been shipped and maintained in a clean and sterile condition. By way of example, the components may be sterilized and packaged in a sterile environment. Alternatively, such components may be packaged and then sterilized, e.g. utilizing gamma radiation sterilization or utilizing ethylene oxide gas sterilization. Further, the front face portion 164 of the septum 160 of the transfer adapter 100 and/or the front face portion 444 of the septum 440 of the vial adapter 400 may be cleaned and/or otherwise disinfected by retaining a given one of the components in one hand and utilizing the other hand to swab the septum thereof with an appropriate disinfectant (e.g. comprising 70% isopropyl alcohol). Then, the transfer adapter 100 may be interconnected to a male luer fitting 50 of a needleless syringe 52 as shown in FIG. 9A. By way of example, the syringe 54 may contain a medical liquid employable as a diluent for or reconstitution of a drug in concentrate form or in powder form, respectively. For connection purposes, the first connection port 110 of the transfer adapter 100 may be positioned in aligned relation with the male luer fitting 50 of the needless syringe 52. Then, the first connection port 110 may be rotatively advanced (e.g. via clockwise twisting of second housing 120) relative to the male luer fitting 50 of the needless syringe 52 to realize secure interconnection therebetween.

Next, and as shown in FIG. 9B, the vial adapter 400 may be sealably interconnected to a vial 80 containing a drug. More particularly, the first connection port 512 of the vial adapter 400 may be aligned with a vial port 82 and then linearly advanced to realize a snap-engagement therebetween. In conjunction with such snap-engagement step, the end 434 of the tubular member 430 of the vial adapter 400 may penetrate and pass through a seal member 84 disposed across an opening of the vial port 84 of vial 80, as will be further described in relation to FIGS. 10A-10C hereinbelow.

Figure 9C:
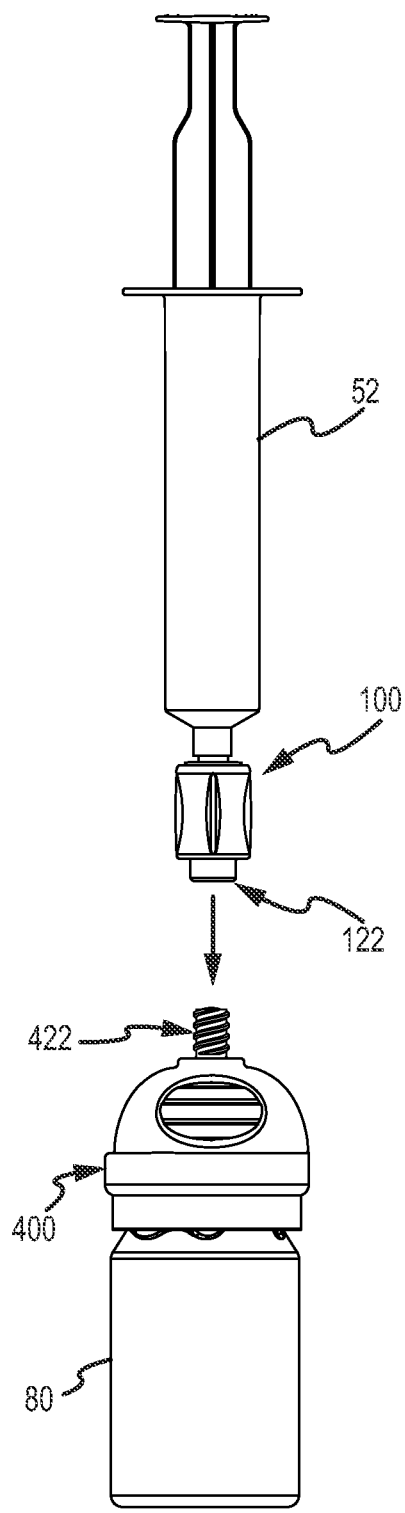
Figure 9D:
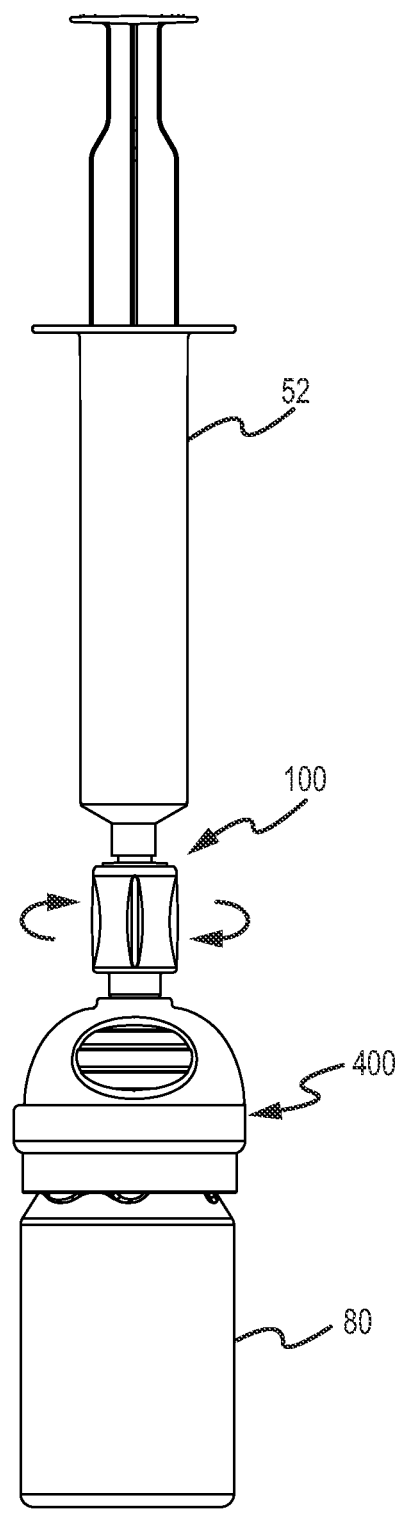

The transfer adapter 100 may then be interconnected to the vial adapter 400 as shown in FIGS. 9C and 9D. More particularly, the second connection port 122 of the transfer adapter 100 may be positioned in aligned relation with the second connection port 422 of the vial adapter 400 as shown in FIG. 9C. Then, the second connection port 122 of the transfer adapter 100 may be rotatively advanced (e.g. via clockwise twisting of the second housing 120 relative to the port 522) as shown in FIG. 9D, while retaining the vial 80 and interconnected vial adapter 400 to achieve interconnection between the second connection port 422 of the transfer adapter 100 and second connection port 422 of the vial adapter 400. After such connection has been made, the needleless syringe 52 may be manipulated so as to contain a liquid drug within the barrel of the needleless syringe 52.

By way of example, when the vial 80 contains a liquid drug to be directly drawn into the needleless syringe 52, the syringe 52 may be at least partially pre-filled with air. Then, following the interconnection shown in FIGS. 9C and 9D, a repetitive process of adding air to the vial 80 from the syringe 52 followed by withdrawal of a portion of the liquid drug from the vial 80 to the syringe 52 may be carried out until the desired quantity of the liquid drug has been passed into the syringe 52. In one approach, the vial 80 may be positioned in an upright orientation with the interconnected syringe 52 in a downward orientation, wherein a portion of the air within syringe 52 may be passed into the vial 80 by advancing the plunger of the syringe 52 relative to the barrel thereof. Then, the interconnected vial adapter 500, transfer adapter 100 and syringe 52 may be inverted, wherein a portion of the liquid drug contained within the vial 80 may be passed into the syringe 52 by retracting the plunger of the syringe relative to the barrel thereof. As noted, the described procedure of air passage from syringe 52 to vial 80, and liquid passage from vial 80 to syringe 52, may be repeated a plurality of times.

In another example, when the vial 80 contains a drug in a powder or concentrate form the syringe 52 may be partially pre-filled with a medical liquid. Then, following the interconnection shown in FIGS. 9C and 9D, a repetitive and process of additively removing air from the vial 80 into the syringe 52 and additively passing medical liquid from the syringe 52 into the vial 80 may be carried out until a desired quantity of medical liquid from the syringe 52 has been passed into the vial 80 to achieve the desired reconstitution or dilution quantity of liquid drug. In one approach, the vial 80 may be positioned in an upright orientation with the interconnected syringe 52 in a downward orientation, wherein a portion of the air within the vial 80 may be drawn into the syringe 52 by withdrawing the plunger of the syringe 52 relative to the barrel thereof. In turn, air bubbles will rise through the medical liquid within the syringe 52 to within a portion of the barrel adjacent to the plunger of the syringe 52. Then, the plunger of the syringe 52 may be advanced so as to introduce a portion of the medical liquid from the syringe 52 into the vial 80. Such a process may be repeated a number of times.

In conjunction with such procedure, the medical liquid may be mixed with the drug concentrate or powder via agitation of the mixture within the vial. After the liquid drug mixture has been formed, the desired amount thereof may be passed from the vial 80 into the syringe 52 by inverting the interconnected vial adapter 500, transfer adapter 100 and syringe 52, and retracting the plunger of the syringe 52 relative to the barrel thereof so as to withdraw the desired quantity of liquid drug into the barrel of the syringe 52.

After the syringe 52 has been filled with a desired quantity of liquid drug, the transfer adapter 100 may be disconnected from the vial connector 400 by rotating the second housing 120 of the transfer adapter 100 (e.g. via counter-clockwise twisting of the second housing 120) while holding the vial adapter 400. As may be appreciated, the liquid drug may then be administered from the syringe 54 to a patient via a patient connector 200 as described above in relation to FIGS. 7C-7E.

Alternatively, the liquid drug may be passed from the syringe 52 into a fluid reservoir, e.g. via interconnection of transfer adapter 100 to a reservoir adapter 300 interconnected to a fluid reservoir 70. In turn, the liquid drug may be diluted within the reservoir for subsequent administration to a patient via an infusion tubing line set 54, otherwise described herein.

In yet another approach, after a liquid drug mixture has been formed in a vial 80 a connection port 112 of another transfer adapter 100 may be interconnected to a standard male luer fitting of a syringe containing a medical liquid employable as a diluent. In turn, a second connection port 122 of the transfer adapter 100 may be connected to the vial adapter 500 and a desired amount of the liquid drug contained in the vial 80 may be mixed with the diluent in the syringe interconnected to port 112. In turn, the liquid drug in the syringe may be administered via the interconnected transfer adapter 100 as described herein.

In relation to the interconnection of the vial adapter 400 and a vial 80 described above in relation to FIG. 9B, reference will now be made to FIGS. 10A-10C which illustrate the positioning and interface of the components of the vial adapter 400 and vial 80 as interconnections are made therebetween. In particular, FIG. 10A illustrates the vial adapter 400 positioned and aligned contact with vial port 82 of vial 80. More particularly, the angled surfaces of interconnection members 492 of the vial adapter 400 are shown in self-centering contact with a vial port 82 having a seal member 84 positioned thereacross. Further, the cap seal member 404 of the vial adapter 400 is shown in contact with the outer surface of the seal member 84.

Upon linear advancement of the vial adapter 400 relative to the vial 80, the free ends 492*b* of the interconnection members 492 may engage a protruding annular lip at a top end of vial 80 and thereby deflect outward as the end 432 of the tubular member 430 of the vial adapter 400 penetrates through the cap seal cap 404 and through the seal member 84 at the vial port 82 of the vial 80, as illustrated in FIG. 10B. Then, upon further linear advancement of the vial adapter 400 relative to the vial 80, the free ends 492*b* of the interconnection members 492 may automatically at least partially return to their initial positions and into snap-fit engagement with the top end of vial 80. More particularly, and as shown in FIG. 10C the free ends 492b of the interconnection members 492 may partially snap-back to their initial position to facilitate secure interconnection with a protruding annular lip at a top end of the vial 80. In this regard, the top surfaces 492c of the interconnection members 492 may engage a downward facing surface portion of the protruding lip of vial 80. As further illustrated by FIG. 10C, the seal cap 404 may be provided so as to be at least partially compressed upon secure, snap-fit interconnection between the vial adapter 400 and the vial 80, thereby further enhancing a sealed interface therebetween.

Reference is now made to FIGS. 11A-11G which illustrate a method embodiment for passing a medical liquid between a needleless syringe 54 and a fluid reservoir 70 utilizing the transfer adapter 100 and the fluid reservoir adapter 300 described hereinabove. Initially the reservoir adapter 300 and transfer adapter 100 may be removed from separate or common packaging in which such components have been shipped and maintained in a clean and sterile condition. By way of example, the components may be sterilized and packaged in a sterile environment. Alternatively, such components may be packaged and then sterilized, e.g. utilizing gamma radiation sterilization or utilizing ethylene oxide gas sterilization.

Initially, the front face portion 164 of the septum 160 of the transfer adapter 100 and/or the front face portion 344 of the septum 340 of the reservoir adapter 300 may be cleaned and/or otherwise disinfected by retaining a given one of the components in one hand and utilizing the other hand to swab the septum thereof with an appropriate disinfectant (e.g. comprising 70% isopropyl alcohol). Then, the transfer adapter may be interconnected to a male luer fitting 50 of a needleless syringe 52 as shown and described above in relation to FIG. 9A.

Then, and as shown in FIG. 11A, the protective member 304 may be removed from the first connection port 312 of the reservoir adapter 300. In this regard, interconnection members 392 may be initially packaged in an "unlocked" position relative to the port 312 within the protective member 304, wherein the protective member 304 protects against unintended premature locking. After removal of the member 304 the interconnection members 392 may be articulated away from and the first connection port 312 may be aligned for interconnection with a fluid reservoir port 72 of a fluid reservoir 70.

In this regard the fluid reservoir port 72 may be generally adapted for interfacing with a cannula. More particularly, the reservoir port 72 may include at least one resilient septum therewithin that may be pierced by a cannula advanced relative thereto wherein a medical liquid may be passed through the cannula and into or out of the fluid reservoir 70. By way of example, the cannula of a syringe may be inserted through the septum(s) at port 72 and the plunger of the syringe may be advanced or retracted relative to the barrel thereof so as to pass a medical liquid from the syringe into the fluid reservoir 70 or from the reservoir 70 into the syringe. Thereafter, the cannula may be withdrawn from the septum(s) at port 72, wherein the septum(s) may be sealably re-closed. As may be appreciated, such utilization of port 72 prior to interconnection of reservoir adapter 300 represents an optional, but not required, step that may be advantageously employed in conjunction with the methodologies of the described embodiments.

In any case, when interconnection of reservoir adapter 300 to fluid reservoir 70 is desired, the first connection port 312 thereof may be linearly advanced as shown in FIG. 11B. In this regard, the reservoir adapter 300 may be advanced until the first connection port 312 has received therewithin the port 72 of the fluid reservoir 70, as shown in FIG. 11C. Upon receipt of the port 72 of the fluid reservoir 70 within the first connection port 312 of the vial adapter 300 the interconnection members 392 may be pivoted, or articulated, about the hinges 398, wherein the members 393 may pass through the apertures 319 and into snap-fit, locked engagement, and wherein flanges 394 pass through the windows 318 to capture and/or engage the port 72 of the fluid reservoir 70 within the first connection port 312 of the reservoir adapter 300.

The transfer adapter 100 with the interconnected syringe 52 may then be interconnected to the reservoir adapter 300 as shown in FIG. 11D. More particularly, the second connection port 122 of the transfer adapter 100 may be positioned in aligned relation with the second connection port 322 of the reservoir 300. Then, the second connection port 122 of the transfer adapter 100 may be rotatively advanced (e.g. via clockwise twisting of the second housing 120 relative to the port 322) to achieve interconnection between the second connection port 122 of the transfer adapter 100 and second connection port 322 of the reservoir adapter 322. After such connection has been made, the needleless syringe 52 may be manipulated so as to draw a medical liquid from the reservoir 70 into the barrel of the needleless syringe 52, as shown in FIG. 11E.

After the syringe 52 has been filled with a desired quantity of the medical liquid, the transfer adapter 100 may be disconnected from the reservoir adapter 300 by rotating the second housing 120 of the transfer adapter 100 (e.g. via counter-clockwise twisting of the second housing 120). As may be appreciated, the medical liquid may then be passed from the syringe 54 to a vial for drug dilution or reconstitution as described above in relation to FIG. 9C.

After drug reconstitution or dilution, a liquid drug may be either administered per patient from syringe 52 as described above in relation to FIGS. 7D and 7E above or passed back into a fluid reservoir 70 for administration to a patient via a tubing line of tubing set 54 as described above. In this regard, and as shown in FIGS. 11F and 11G, to pass a liquid drug from syringe 52 into a reservoir 70, the second connection port 122 of the transfer adapter 100 may be aligned with the second connection port 322 of the reservoir adapter 300. Then, the second connection port 122 of the transfer adapter 100 may be rotatively advanced to achieve interconnection between the second connection port 122 of the transfer adapter 100 and second connection port 322 of the reservoir adapter 300. After such connection has been made, the plunger of the needleless syringe 52 may be advanced so as to pass liquid from the syringe 52 into the reservoir 70.

In relation to the interconnection of the reservoir adapter 300 to the reservoir 70 described above in relation to FIGS. 11A-11C, reference will now be made to FIGS. 12A-12E which illustrate the positioning and interface of the components of the reservoir adapter 300 and a reservoir 70 as interconnections are made therebetween.

Figure 12A:
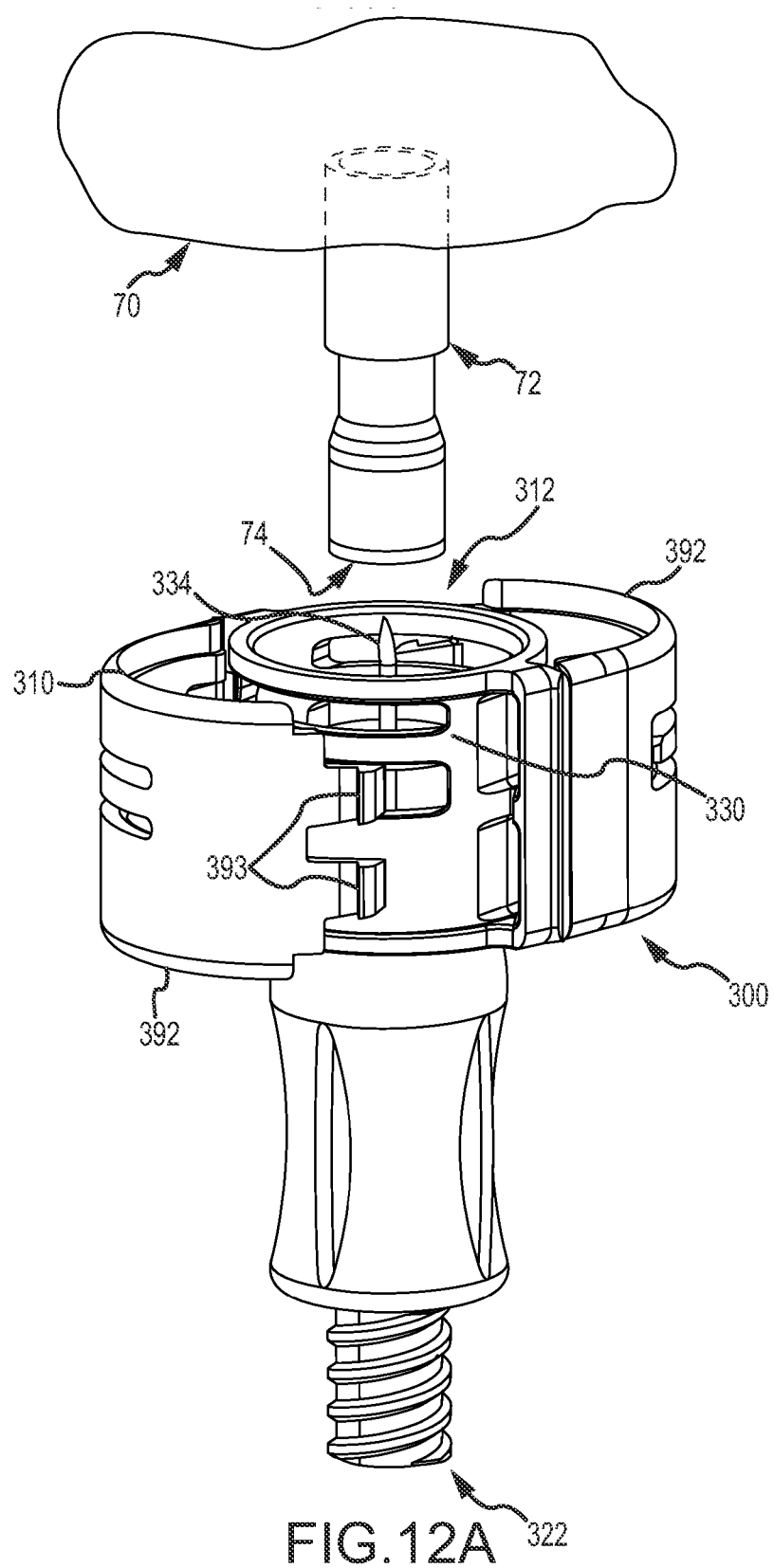
FIG. 12A illustrate a reservoir adapter embodiment and a fluid reservoir port in aligned relation.
Figure 12B:
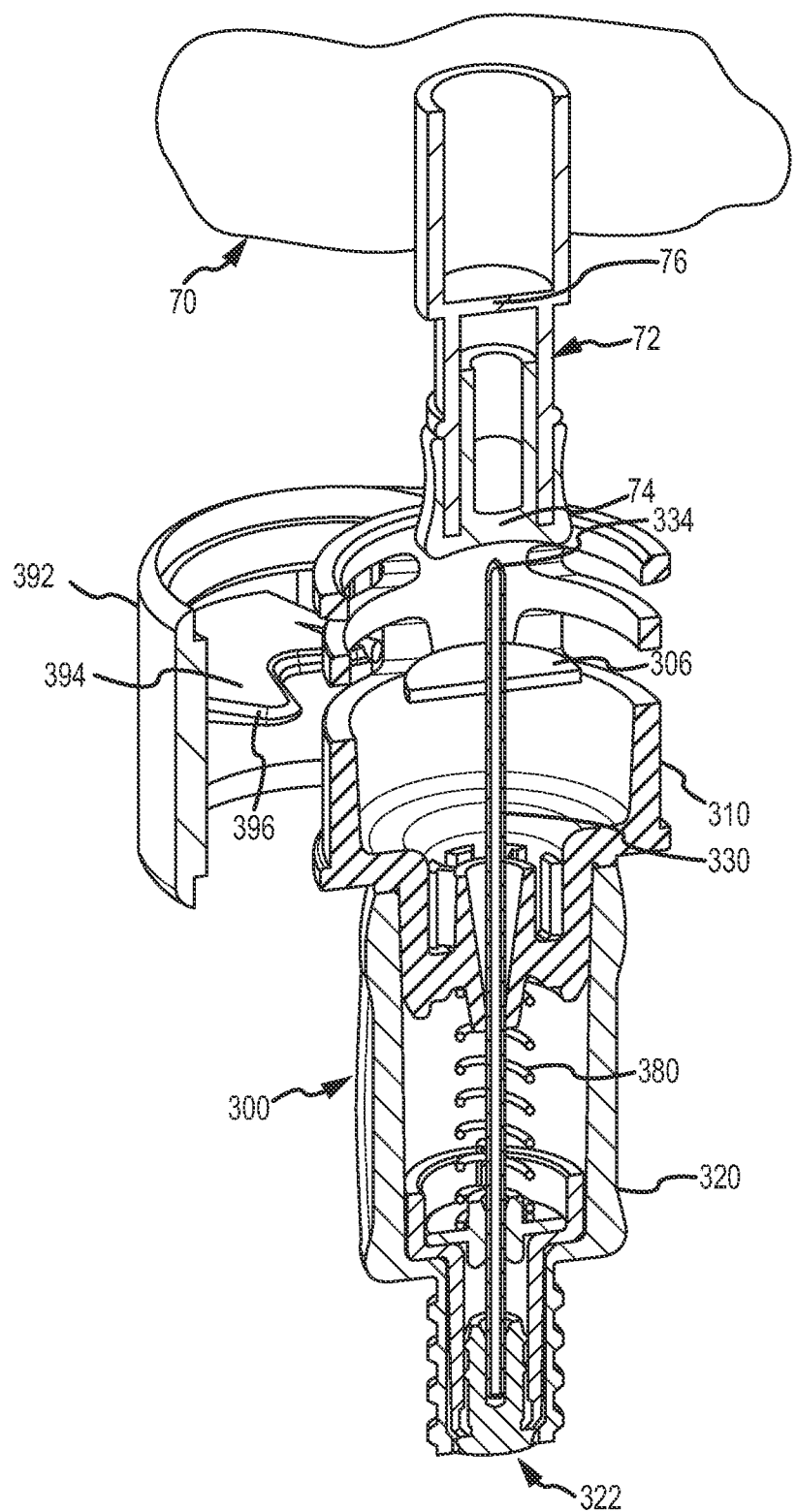
FIGS. 12B, 12C, 12D and 12E are cross sectional views of the fluid reservoir adapter embodiment and fluid reservoir port of FIG. 12A shown in progressive stages of interconnection for liquid transfer therebetween.
Figure 12C:
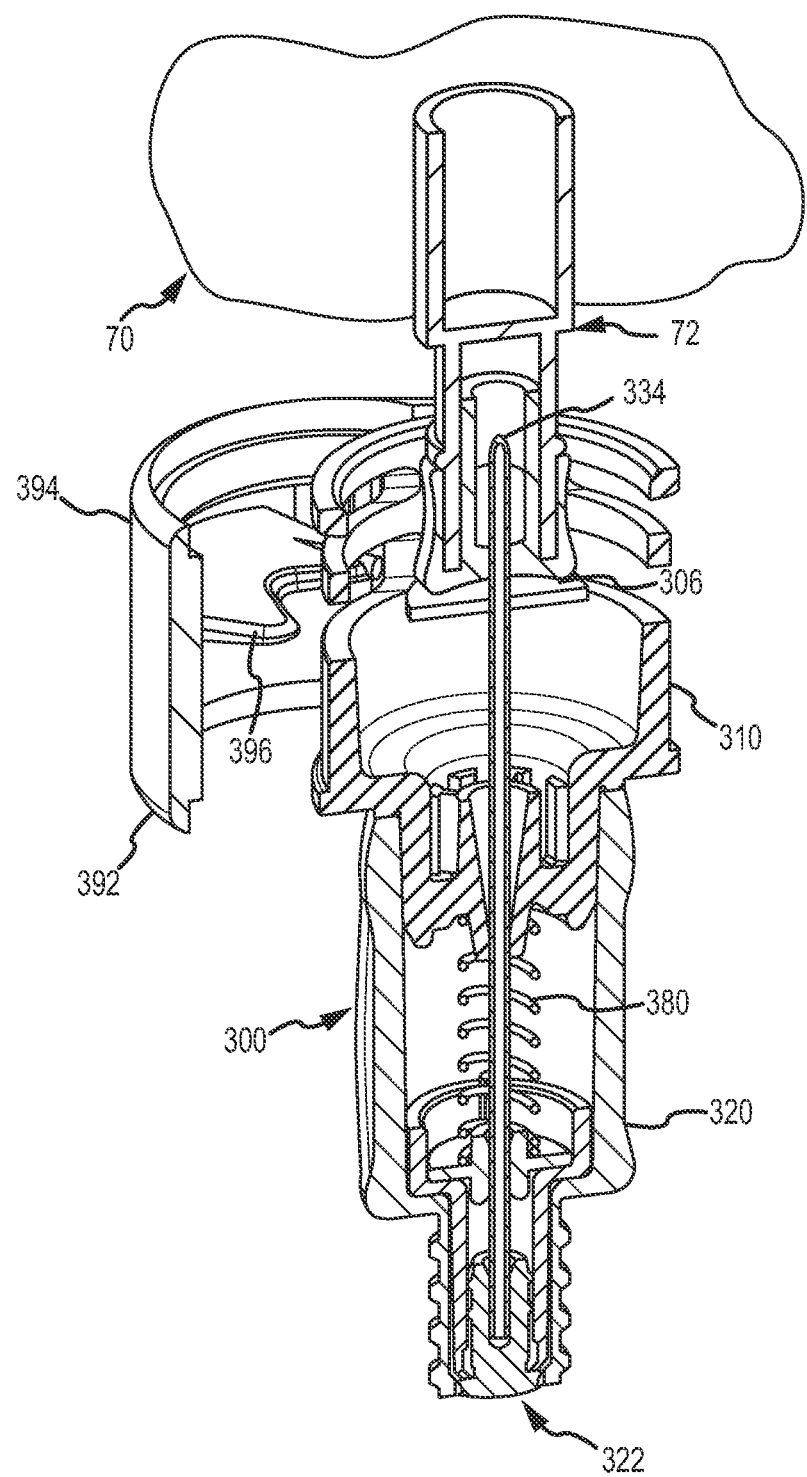
Figure 12D:
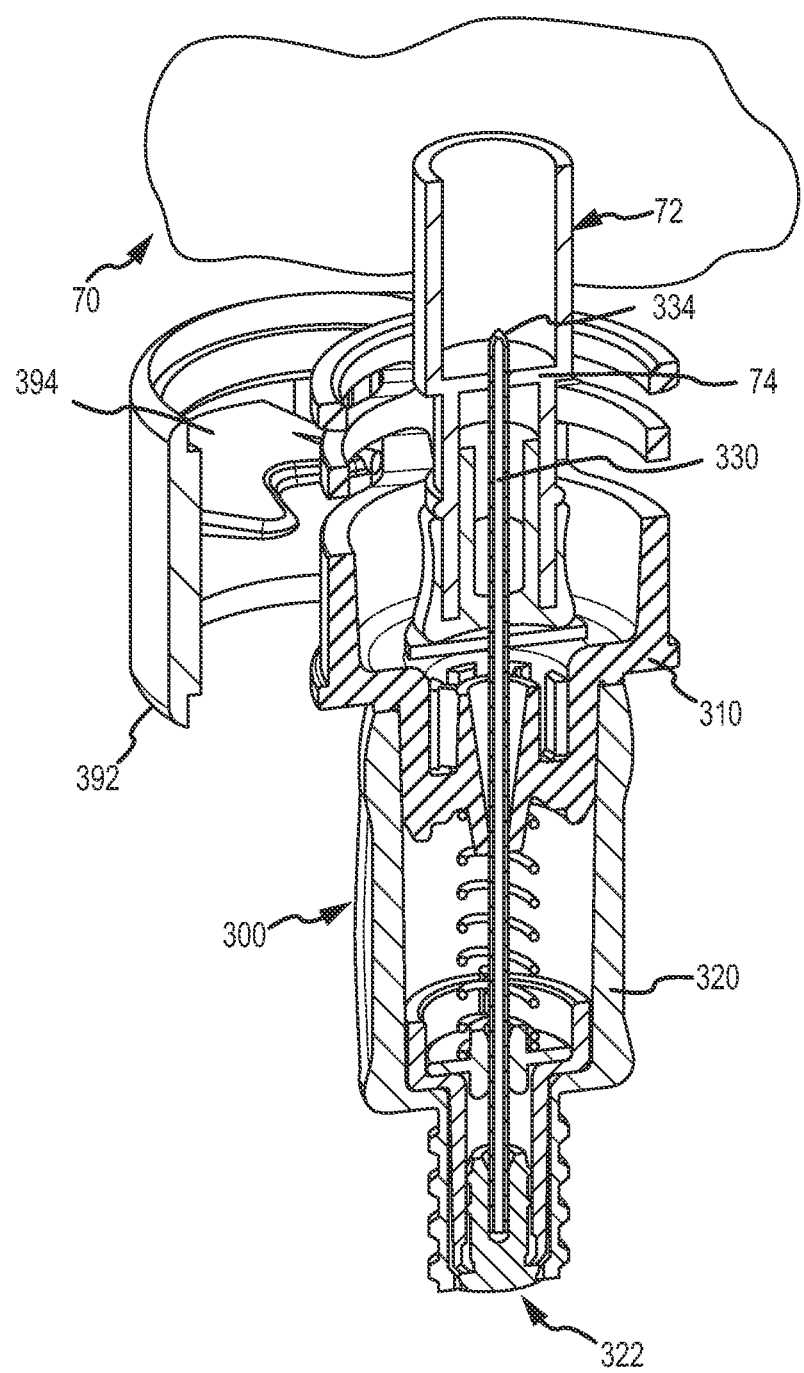
Figure 12E:
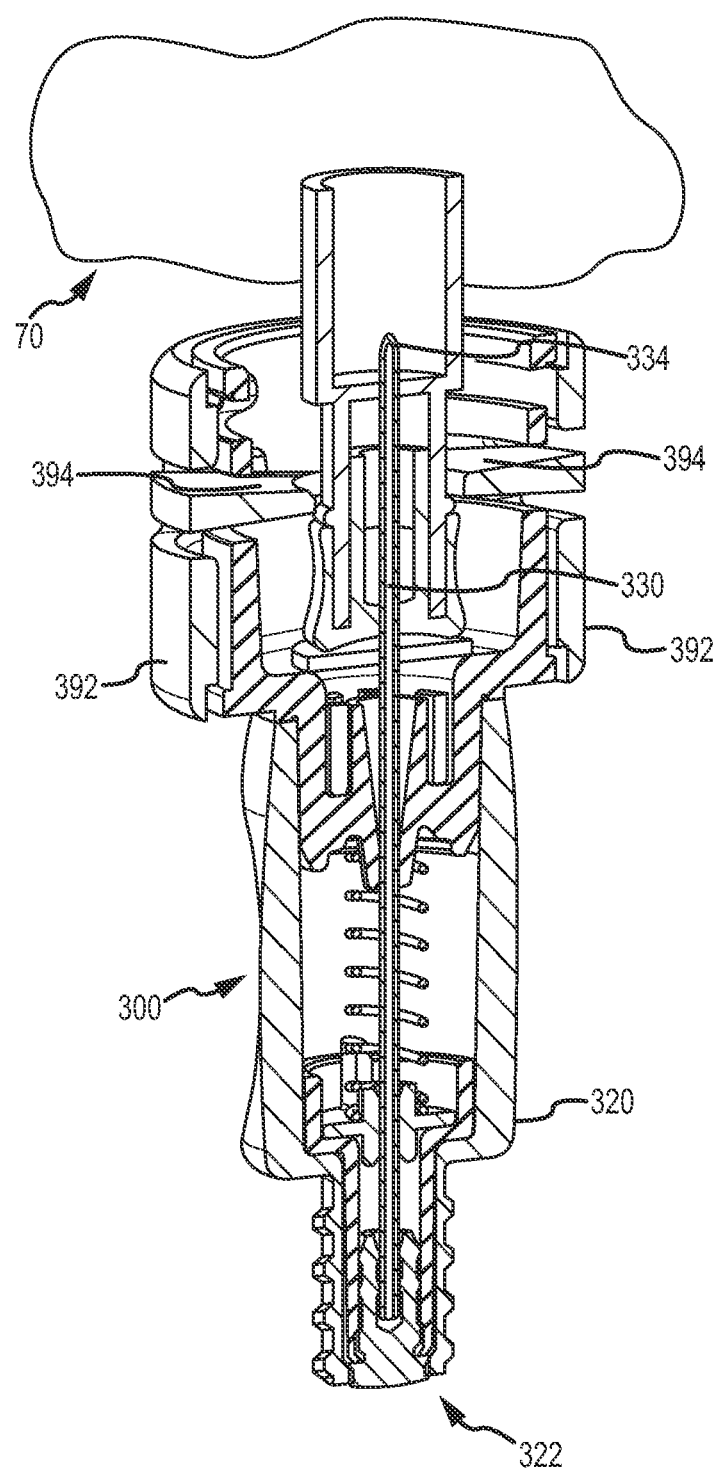

In particular, FIG. 12A illustrates the reservoir adapter 300 positioned in aligned relation with a reservoir port 72. Upon linear advancement of the reservoir adapter 300 relative to the reservoir port 72 the free end 332 of the tubular member 330 of the reservoir adapter 300 may engage and penetrate through a seal member 74 of the reservoir port 72, as shown in FIGS. 12B and 12C. As further shown by FIG. 12C a seal member 306 of the reservoir adapter 300 may engage the front surface of the seal member 74. In turn, as the reservoir adapter 300 is further advanced the seal member 306 may be pushed along the tubular member 340 until it engages a stop region by the first housing 310 of the reservoir adapter 300, as shown in FIG. 12D. In conjunction with such further advancement, the end 332 of the tubular member 330 may penetrate another internally-defined seal member 76 of the port 702. The interconnection members 392 of the reservoir adapter 300 may then be pivoted about hinges 398, wherein the engagement flanges 394 may pass through windows 318 and into the interconnection port 312 so as to capture the reservoir port 74 therewithin, as shown in FIG. 12E. At the same time, the snap-lock members 393 may pass through corresponding apertures 319 to realize a locked, snap-fit engagement. In this regard, such snap-fit engagement may be provided so that the interconnection members 392 are not manipulable once the locked-position is assumed. As shown in FIG. 12D, the reservoir port 72 is captured in/or otherwise restrainably engaged within the locked second connection port 312. In such position, a medical liquid may be passed to/from the reservoir 70 from/to a needleless syringe that is interconnected to a transfer adapter 100 that is interconnected to the reservoir adapter 300.

The various embodiments described above are provided for purposes of example only. Other embodiments incorporating one or more features of the present invention will be apparent to those skilled in the art and are intended to be encompassed by the claims which follow.

The invention claimed is:

1. A system for use in handling a medical liquid, comprising:
   a transfer adapter having a first transfer connection port rotatably interconnectable to a male luer fitting of at least one of a needleless syringe and an infusion tubing line port, and a second connection port;
   a patient connector having a first connection port rotatably interconnectable to a female luer fitting of an intravascular catheter access port, and a second connection port compatible with the second connection port of the transfer adapter, wherein the second connection port of the patient connector is interconnectable to the second connection port of the transfer adapter, wherein a first closed fluid passageway through the patient connector and the transfer adapter is automatically defined upon interconnection of the second connection port of the patient connector and the second connection port of the transfer adapter;
   a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway through the vial adapter and the transfer adapter is automatically defined upon interconnection of the second connection port of the vial adapter and the second connection port of the transfer adapter; and,
   a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway through the reservoir adapter and the transfer adapter is automatically defined upon interconnection of the second connection port of the reservoir adapter and the second connection port of the transfer adapter,
   wherein said second connection port of said transfer adapter is alternately interconnectable to and disconnectable from said second connection port of each of said patient connector, said vial adapter, and said reservoir adapter, wherein said second connection port of said transfer adapter comprises one of an internally-threaded surface and an externally-threaded surface, and wherein said second connection port of said patient connector, said second connection port of said vial adapter and said second connection port of said reservoir adapter each comprise the other of an internally-threaded surface and an externally-threaded surface, complimentary to said one of said internally-threaded surface and externally-threaded surface.

2. A system as recited in claim 1, wherein said second connection port of said transfer adapter comprises an internally-threaded surface, and wherein said second connection port of said patient connector, said second connection port of said vial adapter and said second connection port of said reservoir adapter each comprise an externally-threaded surface, complimentary to said internally-threaded surface.

3. A system as recited in claim 1, wherein said second connection port of said transfer adapter comprises an externally-threaded surface, and wherein said second connection port of said patient connector, said second connection port of said vial adapter and said second connection port of said reservoir adapter each comprise an internally-threaded surface, complimentary to said externally-threaded surface.

4. A system for use in handling a medical liquid, comprising:
   a transfer adapter having a first transfer connection port rotatably interconnectable to a male luer fitting of at least one of a needleless syringe and an infusion tubing line port, and a second connection port;
   a patient connector having a first connection port rotatably interconnectable to a female luer fitting of an intravascular catheter access port, and a second connection port compatible with the second connection ort of the transfer adapter, wherein the second connection port of the patient connector is interconnectable to the second connection port of the transfer adapter, wherein a first closed fluid passageway through the patient connector and the transfer adapter is automatically defined upon interconnection of the second connection port of the patient connector and the second connection port of the transfer adapter;
   a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway through the vial adapter and the transfer adapter is automatically defined upon interconnection of the second connection port of the vial adapter and the second connection port of the transfer adapter; and,
   a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway through the reservoir adapter and the transfer adapter is automatically defined upon interconnection of the second connection port of the reservoir adapter and the second connection port of the transfer adapter;

wherein said second connection port of said transfer adapter is alternately interconnectable to and disconnectable from said second connection port of each of said patient connector, said vial adapter, and said reservoir adapter;

wherein a tubular member of said transfer adapter and a tubular member of at least one of said patient connector, said vial adapter, or said reservoir adapter are automatically, fluidly interconnected to define at least a portion of said first, second or third closed fluid passageways through the tubular members upon interconnection of the transfer adapter and the at least one of said patient connector, said vial adapter, or said reservoir adapter;

wherein at least one of said patient connector, said vial adapter, or said reservoir adapter includes at least one seal member that sealably encloses an end of said tubular member of the at least one of said patient connector, said vial adapter, or said reservoir adapter when said second connection port thereof is in a disconnected state, and wherein said transfer adapter includes at least one seal member that sealably encloses an end of said tubular member of the transfer adapter when said second connection port thereof is in a disconnected state;

wherein the tubular member of the transfer adapter includes first and second opposite ends, wherein the second end of the tubular member is disposed closer to the second connection port of the transfer adapter than is the first end of the tubular member, and wherein the second end of said tubular member and said seal member of said transfer adapter are biased to a recessed position relative to said second connection port of said transfer adapter when said second connection port of said transfer adapter is in a disconnected state.

5. A system as recited in claim 4, wherein said second connection port of said patient connector, said second connection port of said vial adapter, and said second connection port of said reservoir adapter are commonly configured and are each interconnectable to and disconnectable from a male luer fitting of a clean needleless syringe.

6. A system as recited in claim 4, wherein said second connection port of said transfer adapter is rotatably interconnectable to and rotatably disconnectable from said second connection port of said patient connector, said second connection port of said vial adapter, and said second connection port of said reservoir adapter.

7. A system as recited in claim 6, wherein said second connection port of said transfer adapter comprises one of an internally-threaded surface and an externally-threaded surface, and wherein said second connection port of said patient connector, said second connection port of said vial adapter and said second connection port of said reservoir adapter each comprise the other of an internally-threaded surface and an externally-threaded surface, complimentary to said one of said internally-threaded surface and externally-threaded surface.

8. A system as recited in claim 7, wherein said second connection port of said transfer adapter comprises an internally-threaded surface, and wherein said second connection port of said patient connector, said second connection port of said vial adapter and said second connection port of said reservoir adapter each comprise an externally-threaded surface, complimentary to said internally-threaded surface.

9. A system as recited in claim 7, wherein said second connection port of said transfer adapter comprises an externally-threaded surface, and wherein said second connection port of said patient connector, said second connection port of said vial adapter and said second connection port of said reservoir adapter each comprise an internally-threaded surface, complimentary to said externally-threaded surface.

10. A system as recited in claim 4, wherein upon interconnection of the transfer adapter and the at least one of said patient connector, said vial adapter, or said reservoir adapter, said first, second or third closed fluid passageway extends from said first connection port of said the at least one of said patient connector, said vial adapter, or said reservoir adapter and to said first connection port of said transfer adapter.

11. A system as recited in claim 4, wherein said seal member of the at least one of said patient connector, said vial adapter, or said reservoir adapter is biased to close said second connection port of said at least one of said patient connector, said vial adapter, or said reservoir adapter, and wherein a front face of said seal member of said at least one of said patient connector, said vial adapter, or said reservoir adapter is one of disposed substantially flush with and disposed outwardly beyond said second connection port of said at least one of said patient connector, said vial adapter, or said reservoir adapter, when said second connection port of said at least one of said patient connector, said vial adapter, or said reservoir adapter is in a disconnected state.

12. A system as recited in claim 4, wherein the tubular member of the transfer adapter and a tubular member of each of said patient connector, said vial adapter, and said reservoir adapter are automatically, fluidly interconnected to define at least a portion of said first, second and third closed fluid passageways through the tubular members upon interconnection of the transfer adapter and each of the patient connector, said vial adapter, and said reservoir adapter.

13. A system as recited in claim 12, wherein each of said patient connector, said vial adapter, and said reservoir adapter includes at least one seal member that sealably encloses an end of said tubular member of said patient connector, said vial adapter, and said reservoir adapter when said second connection port thereof is in a disconnected state.

14. A system as recited in claim 4, wherein the second connection port includes internal threads having a distal end portion, and wherein said second end of said tubular member and said seal member of said transfer adapter are offset inwardly in relation to the distal end portion of the internal threads.

15. A system for use in handling a medical liquid, comprising:

a transfer adapter having a first transfer connection port rotatably interconnectable to a male luer fitting of at least one of a needleless syringe and an infusion tubing line port, and a second connection port;

a patient connector having a first connection port rotatably interconnectable to a female luer fitting of an intravascular catheter access ort and a second connection port compatible with the second connection port of the transfer adapter, wherein the second connection port of the patient connector is interconnectable to the second connection port of the transfer adapter, wherein a first closed fluid passageway though the patient connector and the transfer adapter is automatically defined upon interconnection of the second connection port of the patient connector and the second connection port of the transfer adapter, wherein a tubular member of said patient connector and a tubular member of said transfer adapter are automatically, fluidly interconnected to define at least a portion of said first closed fluid passageway upon interconnection of the patient connector and the transfer adapter, wherein said patient connector includes at least one seal member that sealably encloses an end of said tubular member of the patient connector when said second connection port thereof is in a disconnected state, and wherein said transfer adapter includes at least one seal member that sealably encloses an end of said tubular member of the transfer adapter when said second connection port thereof is in a disconnected state;

a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway though the vial adapter and the transfer adapter is automatically defined upon interconnection of the second connection port of the vial adapter and the second connection port of the transfer adapter, wherein a tubular member of said vial adapter and said tubular member of said transfer adapter are automatically, fluidly interconnected to define at least portion of said second closed fluid passageway upon interconnection of the vial adapter and the transfer adapter, and wherein said vial adapter includes at least one seal member that sealably encloses an end of said tubular member of the vial adapter when said second connection port thereof is in a disconnected state; and, a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway though the reservoir adapter and the transfer adapter is automatically defined upon interconnection of the second connection port of the reservoir adapter and the second connection port of the transfer adapter, wherein a tubular member of said reservoir adapter and said tubular member of said transfer adapter are automatically, fluidly interconnected to define at least a portion of said third closed fluid passageway upon interconnection of the reservoir adapter and the transfer adapter, and wherein said reservoir adapter includes at least one seal member that sealably encloses an end of said tubular member of the reservoir adapter when said second connection ort thereof is in a disconnected state, wherein said tubular member and said seal member of said transfer adapter are biased to a recessed position relative to said second connection port of said transfer adapter when said second connection port of said transfer adapter is in a disconnected state.

16. A system as recited in claim 15, wherein said seal member of said patient connector is biased to close said second connection port of said patient connector, wherein a front face of said seal member of said patient connector is one of disposed substantially flush with and disposed outwardly beyond said second connection port of said patient connector, when said second connection port of said patient connector is in a disconnected state, wherein said seal member of said vial adapter is biased to close said second connection port of said vial adapter, wherein a front face of said seal member of said vial adapter is one of disposed substantially flush with and disposed outwardly beyond said second connection port of said vial adapter, when said second connection port of said vial adapter is in a disconnected state, wherein said seal member of said reservoir adapter is biased to close said second connection port of said reservoir adapter, and wherein a front face of said seal member of said reservoir adapter is one of disposed substantially flush with and disposed outwardly beyond said second connection port of said reservoir adapter, when said second connection port of said reservoir adapter is in a disconnected state.

17. A system for use in handling a medical liquid, comprising: a transfer adapter having a first transfer connection port rotatably interconnectable to a male luer fitting of at least one of a needleless syringe and an infusion tubing line port, and a second connection port; a patient connector having a first connection port rotatably interconnectable to a female luer fitting of an intravascular catheter access port, and a second connection port compatible with the second connection port of the transfer adapter, wherein the second connection port of the patient connector is interconnectable to the second connection port of the transfer adapter, wherein a first closed fluid passageway through the patient connector and the transfer adapter is automatically defined upon interconnection of the second connection port of the patient connector and the second connection port of the transfer adapter; a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway through the vial adapter and the transfer adapter is automatically defined upon interconnection of the second connection port of the vial adapter and the second connection port of the transfer adapter; and, a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway through the reservoir adapter and the transfer adapter is automatically defined upon interconnection of the second connection port of the reservoir adapter and the second connection port of the transfer adapter;

wherein said second connection port of said transfer adapter is alternately interconnectable to and disconnectable from said second connection port of each of said patient connector, said vial adapter, and said reservoir adapter;

wherein a tubular member of said transfer adapter and a tubular member of at least one of said patient connector, said vial adapter, or said reservoir adapter are automatically, fluidly interconnected to define at least a portion of said first, second or third closed fluid passageways through the tubular members upon interconnection of the transfer adapter and the at least one of said patient connector, said vial adapter, or said reservoir adapter; wherein at least one of said patient connector, said vial adapter, or said reservoir adapter includes at least one seal member that sealably encloses an end of said tubular member of the at least one of said patient connector, said vial adapter, or said reservoir adapter when said second connection port thereof is in a disconnected state, and wherein said transfer adapter includes at least one seal member that sealably encloses an end of said tubular member of the transfer adapter when said second connection port thereof is in a disconnected state; wherein the seal member of the at least one of said patient connector, said vial adapter, or said reservoir adapter includes a resilient septum and a carriage member, wherein the carriage member includes an annular end flange, wherein the resilient septum and carriage member interface to sealably enclose the end of the tubular member of the at least one of said patient connector, said vial adapter, or said reservoir adapter when the second connector port thereof is in the disconnected and wherein the resilient septum includes an annular recess that receives the annular end-flange of the carriage member.

18. A system as recited in claim 17, wherein the tubular member of the transfer adapter and a tubular member of each of said patient connector, said vial adapter, and said reservoir adapter are automatically, fluidly interconnected to define at least a portion of said first, second and third closed fluid passageways through the tubular members upon interconnection of the transfer adapter and each of the patient connector, said vial adapter, and said reservoir adapter.

19. A system as recited in claim 18, wherein each of said patient connector, said vial adapter, and said reservoir adapter includes at least one seal member that sealably encloses an end of said tubular member of said patient connector, said vial adapter, and said reservoir adapter when said second connection port thereof is in a disconnected state, and wherein said transfer adapter includes at least one seal member that sealably encloses an end of said tubular member of the transfer adapter when said second connection port thereof is in a disconnected state.

20. A system as recited in claim 19, wherein the seal member of each of said patient connector, said vial adapter, and said reservoir adapter includes a resilient septum and a carriage member, wherein the resilient septum and carriage member interface to sealably enclose the end of the tubular member of said patient connector, said vial adapter, and said reservoir adapter when the second connector port thereof is in the disconnected state, and wherein the resilient septum includes an annular recess that receives an annular end-flange of the carriage member.

21. A system as recited in claim 17, wherein said second connection port of said patient connector, said second connection port of said vial adapter, and said second connection port of said reservoir adapter are commonly configured and are each interconnectable to and disconnectable from a male Luer fitting of a clean needleless syringe.

22. A system as recited in claim 17, wherein said second connection port of said transfer adapter is rotatably interconnectable to and rotatably disconnectable from said second connection port of said patient connector, said second connection port of said vial adapter, and said second connection port of said reservoir adapter.

23. A system as recited in claim 22, wherein said second connection port of said transfer adapter comprises one of an internally-threaded surface and an externally-threaded surface, and wherein said second connection port of said patient connector, said second connection port of said vial adapter and said second connection port of said reservoir adapter each comprise the other of an internally-threaded surface and an externally-threaded surface, complimentary to said one of said internally-threaded surface and externally-threaded surface.

24. A system as recited in claim 17, wherein upon interconnection of the transfer adapter and the at least one of said patient connector, said vial adapter, or said reservoir adapter, said first, second or third closed fluid passageway extends from said first connection port of said the at least one of said patient connector, said vial adapter, or said reservoir adapter and to said first connection port of said transfer adapter.

25. A system for use in handling a medical liquid, comprising: a transfer adapter having a first transfer connection port rotatably interconnectable to a male luer fitting of at least one of a needleless syringe and an infusion tubing line port, and a second connection port; a patient connector having a first connection port rotatably interconnectable to a female luer fitting of an intravascular catheter access port, and a second connection port compatible with the second connection port of the transfer adapter, wherein the second connection port of the patient connector is interconnectable to the second connection port of the transfer adapter, wherein a first closed fluid passageway through the patient connector and the transfer adapter is automatically defined upon interconnection of the second connection port of the patient connector and the second connection port of the transfer adapter; a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway through the vial adapter and the transfer adapter is automatically defined upon interconnection of the second connection port of the vial adapter and the second connection port of the transfer adapter; and, a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway through the reservoir adapter and the transfer adapter is automatically defined upon interconnection of the second connection port of the reservoir adapter and the second connection port of the transfer adapter;

wherein said second connection port of said transfer adapter is alternately interconnectable to and disconnectable from said second connection port of each of said patient connector, said vial adapter, and said reservoir adapter;

wherein a tubular member of said transfer adapter and a tubular member of at least one of said patient connector, said vial adapter, or said reservoir adapter are automatically, fluidly interconnected to define at least a portion of said first, second or third closed fluid passageways through the tubular members upon interconnection of the transfer adapter and the at least one of said patient connector, said vial adapter, or said reservoir adapter; wherein at least one of said patient connector, said vial adapter, or said reservoir adapter includes at least one seal member that sealably encloses an end of said tubular member of the at least one of said patient connector, said vial adapter, or said reservoir adapter when said second connection port thereof is in a disconnected state, and wherein said transfer adapter includes at least one seal member that sealably encloses an end of said tubular member of the transfer adapter when said second connection port thereof is in a disconnected state; wherein the seal member of the at least one of said patient connector, said vial adapter, or said reservoir adapter includes a resilient septum and a carriage member, wherein the carriage member includes an annular end flange, wherein the resilient septum and the carriage member interface to sealably enclose the end of the tubular member of the at least one of said patient connector, said vial adapter, or said reservoir adapter when the second connector port thereof is in the disconnected, wherein the resilient septum includes a front face portion that is disposed outside of the carriage member, and wherein the resilient septum includes a body portion that is disposed within a tubular portion of the carriage member.

26. A system as recited in claim 25, wherein the body portion of the resilient septum includes a receiving cavity that receives an end of the tubular member of the at least one of said patient connector, said vial adapter, or said reservoir adapter.

27. A system as recited in claim 25, wherein the tubular member of the transfer adapter and a tubular member of each of said patient connector, said vial adapter, and said reservoir adapter are automatically, fluidly interconnected to define at least a portion of said first, second and third closed fluid passageways through the tubular members upon interconnection of the transfer adapter and each of the patient connector, said vial adapter, and said reservoir adapter.

28. A system as recited in claim 27, wherein each of said patient connector, said vial adapter, and said reservoir adapter includes at least one seal member that sealably encloses an end of said tubular member of said patient connector, said vial adapter, and said reservoir adapter when said second connection port thereof is in a disconnected state, and wherein said transfer adapter includes at least one seal member that sealably encloses an end of said tubular member of the transfer adapter when said second connection port thereof is in a disconnected state.

29. A system as recited in claim 28, wherein the seal member of each of said patient connector, said vial adapter, and said reservoir adapter includes a resilient septum and a carriage member, wherein the resilient septum and carriage member interface to sealably enclose the end of the tubular member of said patient connector, said vial adapter, and said reservoir adapter when the second connector port thereof is in the disconnected state, wherein the resilient septum includes a front face portion that is disposed outside of the carriage member, and wherein the resilient septum includes a body portion that is disposed within a tubular portion of the carriage member.

30. A system as recited in claim 25, wherein said second connection port of said patient connector, said second connection port of said vial adapter, and said second connection port of said reservoir adapter are commonly configured and are each interconnectable to and disconnectable from a male luer fitting of a clean needleless syringe.

31. A system as recited in claim 25, wherein said second connection port of said transfer adapter is rotatably interconnectable to and rotatably disconnectable from said second connection port of said patient connector, said second connection port of said vial adapter, and said second connection port of said reservoir adapter.

32. A system as recited in claim 31, wherein said second connection port of said transfer adapter comprises one of an internally-threaded surface and an externally-threaded surface, and wherein said second connection port of said patient connector, said second connection port of said vial adapter and said second connection port of said reservoir adapter each comprise the other of an internally-threaded surface and an externally-threaded surface, complimentary to said one of said internally-threaded surface and externally-threaded surface.

33. A system as recited in claim 25, wherein upon interconnection of the transfer adapter and the at least one of said patient connector, said vial adapter, or said reservoir adapter, said first, second or third closed fluid passageway extends from said first connection port of said the at least one of said patient connector, said vial adapter, or said reservoir adapter and to said first connection port of said transfer adapter.

34. A system for use in handling a medical liquid, comprising:
- a transfer adapter having a first transfer connection port rotatably interconnectable to a male luer fitting of at least one of a needleless syringe and an infusion tubing line port, and a second connection port;
- a patient connector having a first connection port rotatably interconnectable to a female luer fitting of an intravascular catheter access port, and a second connection port compatible with the second connection ort of the transfer adapter, wherein the second connection port of the patient connector is interconnectable to the second connection port of the transfer adapter, wherein a first closed fluid passageway through the patient connector and the transfer adapter is automatically defined upon interconnection of the second connection port of the patient connector and the second connection port of the transfer adapter;
- a vial adapter having a first connection port selectively interconnectable to a vial containing a drug and a second connection port compatible with the second connection port of the transfer adapter, wherein the second connection port of the vial connector is interconnectable to the second connection port of the transfer adapter, wherein a second closed fluid passageway through the vial adapter and the transfer adapter is automatically defined upon interconnection of the second connection port of the vial adapter and the second connection port of the transfer adapter; and,
- a reservoir adapter having a first connection port selectively interconnectable to a fluid reservoir containing a medical liquid, and a second connection port compatible with the second connection port of the transfer adapter, wherein the second connection port of the reservoir connector is interconnectable to the second connection port of the transfer adapter, wherein a third closed fluid passageway through the reservoir adapter and the transfer adapter is automatically defined upon interconnection of the second connection port of the reservoir adapter and the second connection port of the transfer adapter;
- wherein said second connection port of said transfer adapter is alternately interconnectable to and disconnectable from said second connection port of each of said patient connector, said vial adapter, and said reservoir adapter;
- wherein a tubular member of said transfer adapter and a tubular member of at least one of said patient connector, said vial adapter, or said reservoir adapter are automatically, fluidly interconnected to define at least a portion of said first, second or third closed fluid passageways through the tubular members upon interconnection of the transfer adapter and the at least one of said patient connector, said vial adapter, or said reservoir adapter;
- wherein at least one of said patient connector said vial adapter, or said reservoir adapter includes at least one seal member that sealably encloses an end of said tubular member of the at least one of said patient connector, said vial adapter, or said reservoir adapter when said second connection port thereof is in a disconnected state, and wherein said transfer adapter includes at least one seal member that sealably encloses an end of said tubular member of the transfer adapter when said second connection port thereof is in a disconnected state;
- wherein the seal member of the at least one of said patient connector, said vial adapter, or said reservoir adapter includes a resilient septum and a carriage member, wherein the resilient septum and carriage member interface to sealably enclose the end of the tubular member of the at least one of said patient connector, said vial adapter, or said reservoir adapter when the second connector port thereof is in the disconnected state, and wherein the resilient septum and carriage member are axially displaceable relative to the tubular member of the at least one of said patient connector, said vial adapter, or said reservoir adapter.

35. A system as recited in claim 34, wherein the resilient septum and carriage member are biased towards the second connection port of the at least one of said patient connector, said vial adapter, or said reservoir adapter.

36. A system as recited in claim 34, wherein the tubular member of the transfer adapter and a tubular member of each of said patient connector, said vial adapter, and said reservoir adapter are automatically, fluidly interconnected to define at least a portion of said first, second and third closed fluid passageways through the tubular members upon interconnection of the transfer adapter and each of the patient connector, said vial adapter, and said reservoir adapter.

37. A system as recited in claim 36, wherein each of said patient connector, said vial adapter, and said reservoir adapter includes at least one seal member that sealably encloses an end of said tubular member of said patient connector, said vial adapter, and said reservoir adapter when said second connection port thereof is in a disconnected state, and wherein said transfer adapter includes at least one seal member that sealably encloses an end of said tubular member of the transfer adapter when said second connection port thereof is in a disconnected state.

38. A system as recited in claim 37, wherein the seal member of each of said patient connector, said vial adapter, and said reservoir adapter includes a resilient septum and a carriage member, wherein the resilient septum and carriage member interface to sealably enclose the end of the tubular member of said patient connector, said vial adapter, and said reservoir adapter when the second connector port thereof is in the disconnected state, and wherein the resilient septum and carriage member are axially displaceable relative to the tubular member of said patient connector, said vial adapter, and said reservoir adapter.

39. A system as recited in claim 34, wherein said second connection port of said patient connector, said second connection port of said vial adapter, and said second connection port of said reservoir adapter are commonly configured and are each interconnectable to and disconnectable from a male luer fitting of a clean needleless syringe.

40. A system as recited in claim 34, wherein said second connection port of said transfer adapter is rotatably interconnectable to and rotatably disconnectable from said second connection port of said patient connector, said second connection port of said vial adapter, and said second connection port of said reservoir adapter.

41. A system as recited in claim 40, wherein said second connection port of said transfer adapter comprises one of an internally-threaded surface and an externally-threaded surface, and wherein said second connection port of said patient connector, said second connection port of said vial adapter and said second connection port of said reservoir adapter each comprise the other of an internally-threaded surface and an externally-threaded surface, complimentary to said one of said internally-threaded surface and externally-threaded surface.

42. A system as recited in claim 34, wherein upon interconnection of the transfer adapter and the at least one of said patient connector, said vial adapter, or said reservoir adapter, said first, second or third closed fluid passageway extends from said first connection port of said the at least one of said patient connector, said vial adapter, or said reservoir adapter and to said first connection port of said transfer adapter.

* * * * *